United States Patent
Rayabarapu et al.

(10) Patent No.: US 9,359,549 B2
(45) Date of Patent: *Jun. 7, 2016

(54) ORGANIC ELECTROLUMINESCENT MATERIALS AND DEVICES

(75) Inventors: Dinesh Rayabarapu, Waldwick, NJ (US); Chuanjun Xia, Lawrenceville, NJ (US); Raymond C. Kwong, Fo Tan (HK); Bin Ma, West Windsor, NJ (US); Walter Yeager, Yardley, PA (US); Bert Alleyne, Ewing, NJ (US)

(73) Assignee: Universal Display Corporation, Ewing, NJ (US)

( * ) Notice: Subject to any disclaimer, the term of this patent is extended or adjusted under 35 U.S.C. 154(b) by 1237 days.

This patent is subject to a terminal disclaimer.

(21) Appl. No.: 13/263,294

(22) PCT Filed: Apr. 6, 2010

(86) PCT No.: PCT/US2010/030098
§ 371 (c)(1),
(2), (4) Date: Oct. 28, 2011

(87) PCT Pub. No.: WO2010/118029
PCT Pub. Date: Oct. 14, 2010

(65) Prior Publication Data
US 2012/0061654 A1    Mar. 15, 2012

Related U.S. Application Data

(60) Provisional application No. 61/167,014, filed on Apr. 6, 2009.

(51) Int. Cl.
*H01L 51/54*    (2006.01)
*C09K 11/06*    (2006.01)
(Continued)

(52) U.S. Cl.
CPC ............. *C09K 11/06* (2013.01); *C07F 15/0033* (2013.01); *H01L 51/0085* (2013.01);
(Continued)

(58) Field of Classification Search
CPC .................................................. C09K 2211/104
See application file for complete search history.

(56) References Cited

U.S. PATENT DOCUMENTS 4,769,292 A    9/1988    Tang et al.
5,061,569 A    10/1991    VanSlyke et al.
(Continued)

FOREIGN PATENT DOCUMENTS

CN    101076902 A    11/2007
EP    0650955    5/1995
(Continued)

OTHER PUBLICATIONS

Kuwabara, Yoshiyuki et al., "Thermally Stable Multilayered Organic Electroluminescent Devices Using Novel Starburst Molecules. 4,4',4"-Tri(N-carbazolyl)triphenylamine (TCTA) and 4,4',4"-Tris(3-methylphenylphenyl-amino)triphenylamine (m-MTDATA), as Hole-Transport Materials," *Adv. Mater.*, 6(9):677-679 (1994).
(Continued)

*Primary Examiner* — Marie R. Yamnitzky
(74) *Attorney, Agent, or Firm* — Duane Morris LLP

(57) ABSTRACT

Compounds comprising a metal complex having novel ligands are provided. In particular, the compound is an iridium complex comprising novel aza DBX ligands. The compounds may be used in organic light emitting devices, particularly as emitting dopants, providing improved efficiency, low operating voltage, and long lifetime.

17 Claims, 4 Drawing Sheets

(51) Int. Cl.
*C07F 15/00* (2006.01)
*H01L 51/00* (2006.01)
*H05B 33/14* (2006.01)
*H01L 51/50* (2006.01)

(52) U.S. Cl.
CPC ........ *H05B33/14* (2013.01); *C09K 2211/1029* (2013.01); *C09K 2211/1033* (2013.01); *C09K 2211/1037* (2013.01); *C09K 2211/185* (2013.01); *H01L 51/5016* (2013.01)

(56) References Cited

U.S. PATENT DOCUMENTS

| | | | |
|---|---|---|---|
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,279,704 | B2 | 10/2007 | Walters et al. |
| 7,431,968 | B1 | 10/2008 | Shtein et al. |
| 7,445,857 | B2 | 11/2008 | Shen et al. |
| 8,136,974 | B2 | 3/2012 | Konno |
| 8,722,205 | B2* | 5/2014 | Xia et al. ............... 428/690 |
| 2002/0034656 | A1 | 3/2002 | Thompson et al. |
| 2002/0134984 | A1 | 9/2002 | Igarashi |
| 2003/0068535 | A1 | 4/2003 | Takiguchi et al. |
| 2003/0175553 | A1 | 9/2003 | Thompson et al. |
| 2003/0230980 | A1 | 12/2003 | Forrest et al. |
| 2004/0174116 | A1 | 9/2004 | Lu et al. |
| 2004/0253478 | A1* | 12/2004 | Thompson et al. ........... 428/690 |
| 2005/0025993 | A1 | 2/2005 | Thompson et al. |
| 2005/0119485 | A1 | 6/2005 | Brown et al. |
| 2005/0191519 | A1 | 9/2005 | Mishima et al. |
| 2005/0260441 | A1 | 11/2005 | Thompson et al. |
| 2005/0260449 | A1 | 11/2005 | Walters et al. |
| 2006/0008670 | A1 | 1/2006 | Lin et al. |
| 2006/0008671 | A1 | 1/2006 | Kwong et al. |
| 2006/0202194 | A1 | 9/2006 | Jeong et al. |
| 2006/0251923 | A1 | 11/2006 | Lin et al. |
| 2006/0280965 | A1 | 12/2006 | Kwong et al. |
| 2007/0128466 | A1* | 6/2007 | Nomura et al. ............... 428/690 |
| 2007/0190359 | A1 | 8/2007 | Knowles et al. |
| 2007/0237981 | A1* | 10/2007 | Shen et al. ............... 428/690 |
| 2008/0261076 | A1 | 10/2008 | Kwong et al. |

FOREIGN PATENT DOCUMENTS

| | | |
|---|---|---|
| JP | 2004319438 | 11/2004 |
| JP | 200511610 | 1/2005 |
| JP | 2005276799 A | 10/2005 |
| JP | 2006008927 | 1/2006 |
| JP | 2007123392 | 5/2007 |
| JP | 2007254297 | 10/2007 |
| WO | WO 0139234 | 5/2001 |
| WO | WO 0202714 | 1/2002 |
| WO | WO 03040257 | 5/2003 |
| WO | WO 03060956 | 7/2003 |
| WO | 2004044089 A1 | 5/2004 |
| WO | WO 2004093207 | 10/2004 |
| WO | 2004111066 | 12/2004 |
| WO | WO 2004107822 | 12/2004 |
| WO | WO 2005014551 | 2/2005 |
| WO | WO 2005030900 | 4/2005 |
| WO | WO 2005089025 | 9/2005 |
| WO | 2005101912 | 10/2005 |
| WO | WO 2005123873 | 12/2005 |
| WO | WO 2006009024 | 1/2006 |
| WO | 2006014599 | 2/2006 |
| WO | WO 2006056418 | 6/2006 |
| WO | WO 2006082742 | 8/2006 |
| WO | WO 2006098120 | 9/2006 |
| WO | WO 2006103874 | 10/2006 |
| WO | WO 2006114966 | 11/2006 |
| WO | WO 2006132173 | 12/2006 |
| WO | WO 2007004380 | 1/2007 |
| WO | WO 2007063754 | 6/2007 |
| WO | WO 2007063796 | 6/2007 |
| WO | 2008044723 | 4/2008 |
| WO | 2008109824 | 9/2008 |

OTHER PUBLICATIONS

Paulose, Betty Marie Jennifer S. et al., "First Examples of Alkenyl Pyridines as Organic Ligands for Phosphorescent Iridium Complexes," *Adv. Mater.*, 16(22):2003-2007 (2004).

Tung, Yung-Liang et al., "Organic Light-Emitting Diodes Based on Charge-Neutral Ru$^{II}$ PHosphorescent Emitters," Adv. Mater., 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," *Adv. Mater.*, 19:739-743 (2007).

Wong, Wai-Yeung, "Multifunctional Iridium Complexes Based on Carbazole Modules as Highly Efficient Electrophosphors," *Angew. Chem. Int. Ed.*, 45:7800-7803 (2006).

Tang, C.W. and VanSlyke, S.A., "Organic Electroluminecent Diodes," *Appl. Phys. Lett.*, 51(12):913-915 (1987).

Adachi, Chihaya et al., "Organic Electroluminescent Device Having a Hole Conductor as an Emitting Layer," *Appl. Phys. Lett.*, 55(15):1489-1491 (1989).

Ma, Yuguang et al., "Triplet Luminescent Dinuclear-Gold(I) Complex-Based Light-Emitting Diodes with Low Turn-On voltage," *Appl. Phys. Lett.*, 74(10):1361-1363 (1999).

Gao, Zhiqiang et al., "Bright-Blue Electroluminescence From a Silyl-Substituted ter-(phenylen-vinylene) derivative," *Appl. Phys. Lett.*, 74(6):865-867 (1999).

Baldo, M.A. et al., "Very High-Efficiency Green Organic Light-Emitting Devices Based on Electrophosphorescence," *Appl. Phys. Lett.*, 75(1):4-6 (1999).

Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).

Hung, L.S. et al., "Anode Modification in Organic Light-Emitting Diodes by Low-Frequency Plasma Polymerization of CHF$_3$,"*Appl. Phys. Lett.*, 78(5):673-675 (2001).

Ikai, Masamichi et al., "Highly Efficient Phosphorescence From Organic Light-Emitting Devices with an Exciton-Block Layer," *Appl. Phys. Lett.*, 79(2):156-158 (2001).

Wang, Y. et al., "Highly Efficient Electroluminescent Materials Based on Fluorinated Organometallic Iridium Compounds," *Appl. Phys. Lett.*, 79(4):449-451 (2001).

Kwong, Raymond C. et al., "High Operational Stability of Electrophosphorescent Devices," *Appl. Phys. Lett.*, 81(1):162-164 (2002).

Holmes, R.J. et al., "Blue Organic Electrophosphorescence Using Exothermic Host-Guest Energy Transfer," *Appl. Phys. Lett.*, 82(15):2422-2424 (2003).

Sotoyama, Wataru et al., "Efficient Organic Light-Emitting Diodes with Phosphorescent Platinum Complexes Containing NCN-Coordinating Tridentate Ligand," *Appl. Phys. Lett.*, 86:153505-1-153505-3 (2005).

Okumoto, Kenji et al., "Green Fluorescent Organic Light-Emitting Device with External Quantum Efficiency of Nearly 10%," *Appl. Phys. Lett.*, 89:063504-1-063504-3 (2006).

(56) References Cited

OTHER PUBLICATIONS

Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).

Aonuma, Masaki et al., "Material Design of Hole Transport Materials Capable of Thick-Film Formation in Organic Light Emitting Diodes," *Appl. Phys. Lett.*, 90:183503-1-183503-3 (2007).

Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).

Adachi, Chihaya et al., "Highl-Efficiency Red Electrophosphorescence Devices," *Appl. Phys. Lett.*, 78(11):1622-1624 (2001).

Wong, Keith Man-Chung et al., "A Novel Class of Phosphorescent Gold(III) Alkynyl-Based Organic Light-Emitting Devices with Tunalbe Colour," *Chem. Commun.*, 2906-2908 (2005).

Hamada, Yuji et al., "High Luminance in Organic Electroluminescent Devices with Bis(10-hydroxybenzo[h]quinolinato)beryllium as an Emitter," *Chem. Lett.*, 905-906 (1993).

Nishida, Jun-ichi et al., "Preparation, Characterization, and Electroluminescence Characteristics of αDiimine-type Platinum(II) Complexes with Perfluorinated Phenyl Groups as Ligands," *Chem. Lett.*, 34(4):592-592 (2005).

Mi, Bao-Xiu et al., "Thermally Stable Hole-Transporting Material for Organic Light-Emitting Diode: an Isoindole Derivative," *Chem. Mater.*, 15(16):3148-3151 (2003).

Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).

Niu, Yu-Hua et al., "Highly Efficient Electrophosphorescent Devices with Saturated Red Emission from a Neutral Osmium Complex," *Chem. Mater.*, 17(13):3532-3536 (2005).

Lo, Shih-Chun et al., "Blue Phosphorescence from Iridium(III) Complexes at Room Temperature," *Chem. Mater.*, 18(21):5119-5129 (2006).

Takizawa, Shin-ya et al., "Phosphorescent Iridium Complexes Based on 2- Phenylimidazo[1,2- α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cyclometalated Iridium Complexes," *Inorg. Chem.*, 40(7):1704-1711 (2001).

Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).

Noda, Tetsuya and Shirota, Yasuhiko, "5,5'-Bis(dimesityloryl)-2,2'-bithiophene and 5,5''-Bis(dimesityboryl)-2,2':5',2''-terthiophene as a Novel Family of Electron-Transporting Amorphous Molecular Materials," *J. Am. Chem. Soc.*, 120 (37):9714-9715 (1998).

Sakamoto, Youichi et al., "Synthesis, Characterization, and Electron-Transport Property of Perfluorinated Phenylene Dendrimers," *J. Am. Chem. Soc.*, 122(8):1832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yasuhiko et al., "Starburst Molecules Based on πElectron Systems as Materials for Organic Electroluminescent Devices," *Journal of Luminescence*, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al.,"1,2,4-Triazole Derivative as an Electron Transport Layer in Organic Electroluminescent Devices," *Jpn. J. Appl. Phys.*, 32:L917-L920 (1993).

Van Slyke, S. A. et al., "Organic Electroluminescent Devices with Improved Stability," *Appl. Phys. Lett.*, 69(15 ):2160-2162 (1996).

Baldo, M. A. et al., "Highly Efficient Phosphorescent Emission From Organic Electroluminescent Devices," *Nature*, 395:151-154 (1998).

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based On Silole Derivatives And Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes Of Poly(3-Hexylthiophene): Electro-Optical Characteristics Related to Structure," *Synthetic Metals*, 88:171-177 (1997).

Hu, Nan-Xiang et al., "Novel High $T_g$ Hole-Transport Molecules Based on Indolo[3,2-b]carbazoles for Organic Light-Emitting Devices," *Synthetic Materials*, 111-112:421-424 (2000).

Salbeck, J. et al., "Low Molecular Organic Glasses for Blue Electroluminescence," *Synthetic Metals*, 91:209-215 (1997).

U.S. Appl. No. 61/167,014, filed Apr. 6, 2009.

The International Search Report corresponding to the PCT/US2010/030098 application, dated Jun. 2010.

Notice of Reasons for Rejection issued Mar. 10, 2014 for corresponding Japanese Application No. 2012-504780.

ROC (Taiwan) Patent Office, Notification of Office Action regarding corresponding ROC (Taiwan) Application No. 099110623 issued Mar. 26, 2015, pp. 1-6, (translation provided for p. 6 only).

ROC (Taiwan) Patent Office, English Translation of International Search Report regarding corresponding ROC (Taiwan) Application No. 099110623 issued Mar. 26, 2015, p. 1.

\* cited by examiner

ORGANIC ELECTROLUMINESCENT MATERIALS AND DEVICES

This application claims priority to and benefit under 35 U.S.C. §119(e) to International Application No. PCT/US2010/030098 filed Apr. 6, 2010 and to U.S. Provisional Application No. 61/167,014, filed Apr. 6, 2009, the disclosures of which are herein expressly incorporated by reference in their entirety.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic materials that may be advantageously used in organic light emitting devices. More particularly, the present invention relates to compounds comprising a metal complex having a novel ligand structure and devices incorporating such compounds.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine)iridium, denoted Ir(ppy)$_3$, which has the structure:

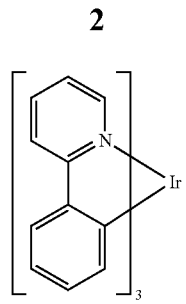

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Compounds comprising a metal complex with novel ligand structures are provided. The compounds may be advantageously used in organic light emitting devices. In particular, the compounds may be useful as phosphorescent emitting dopants in such devices. The novel compounds comprise a ligand having the structure:

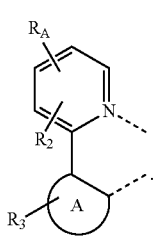

FORMULA I

A is a 5-membered or 6-membered aromatic or heteroaromatic ring. In one aspect, preferably, A is benzene. In another aspect, preferably A is selected from the group consisting of furan, thiophene, and pyrrole. $R_A$ is a substituent having the structure

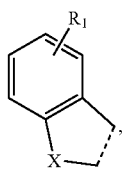

wherein the substituent is fused to the pyridine ring of FORMULA I. The dashed line present in the structure indicates where the substituent is fused to the pyridine ring of FORMULA I. X is selected from the group consisting of CRR', C=O, BR, O, S, and Se. R and R' are independently selected from hydrogen and alkyl. $R_1$, $R_2$, and $R_3$ may represent mono, di, tri, or tetra substitutions; each of $R_1$, $R_2$, and $R_3$ are independently selected from the group consisting of hydrogen, alkyl, alkoxy, amino, alkenyl, alkynyl, arylkyl, aryl, and heteroaryl. The ligand is coordinated to a metal having an atomic weight greater than 40. Preferably, the metal is Ir.

In one aspect, compounds are provided which comprise an aza dibenzo-substituted (aza-DBX) ligand having the structure:

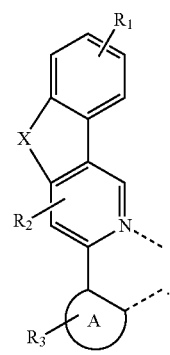

II

In another aspect, compounds are provided wherein the ligand has the structure:

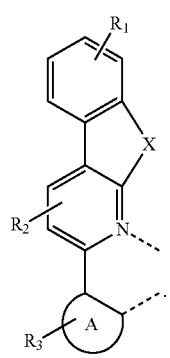

III

In yet another aspect, compounds are provided wherein the ligands has the structure:

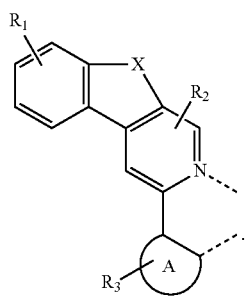

IV

In yet another aspect, compounds are provided wherein the ligands has the structure:

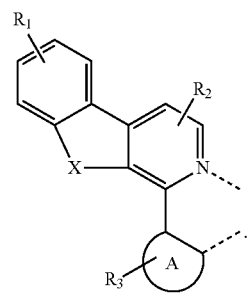

V

In yet another aspect, compounds are provided wherein the ligands has the structure:
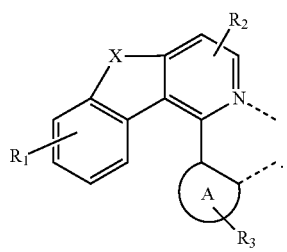
VI
In a further aspect, compounds are provided wherein the ligands has the structure:
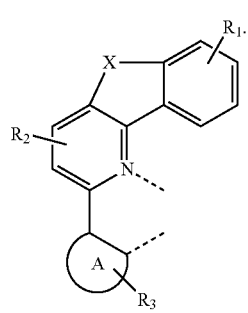
VII
Preferably, the compound has the formula $(L)_n(L')_{3-n}Ir$. L is selected from the group consisting of:
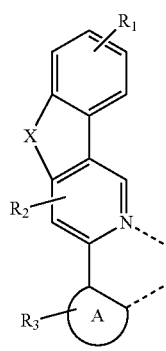
II
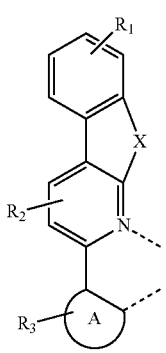
III
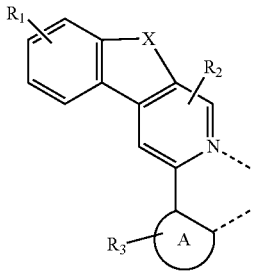
IV
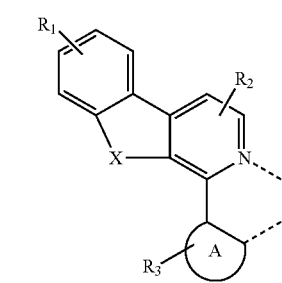
V
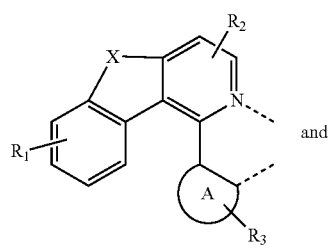
VI
and
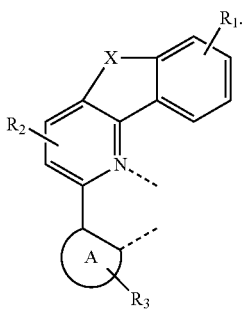
VII
L' is selected from the group consisting of:
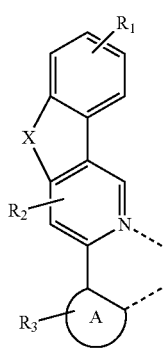
II

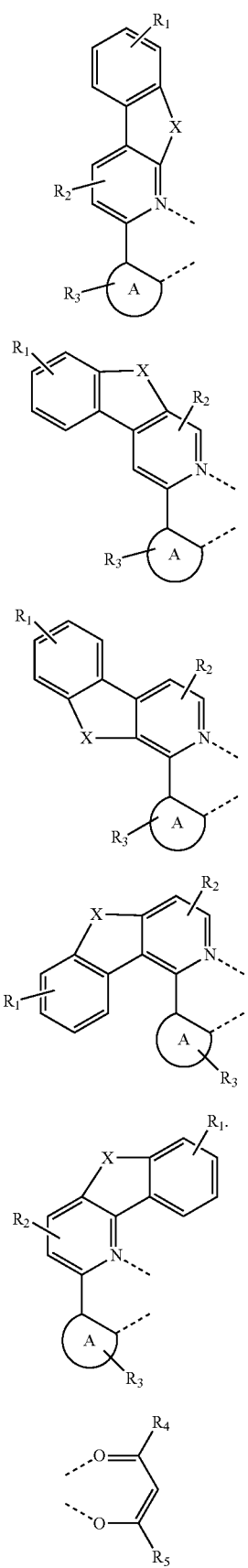

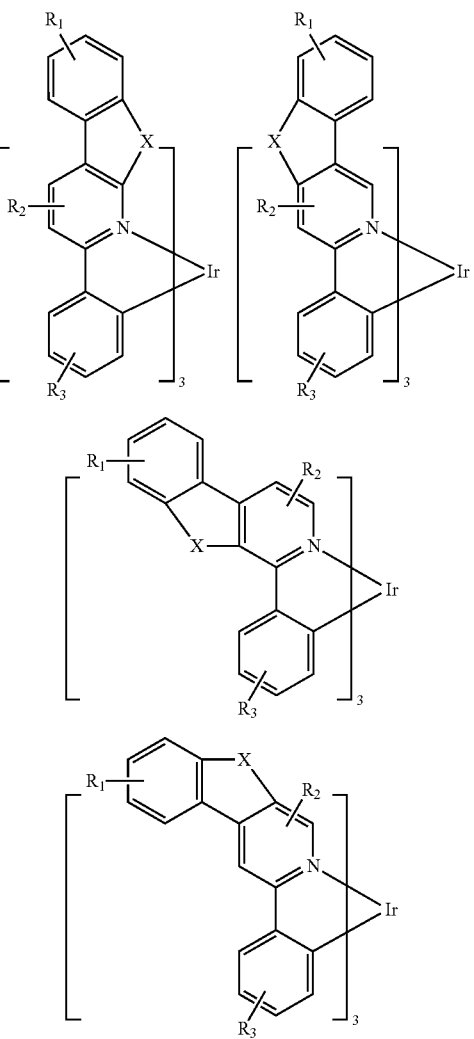

n is 1, 2, or 3. In one aspect, n is 1. In another aspect, n is 2. In yet another aspect, n is 3. $R_4$ and $R_5$ may represent mono, di, tri, or tetra substitutions; and $R_4$ and $R_5$ are independently selected from the group consisting of hydrogen, alkyl, alkoxy, amino, alkenyl, alkynyl, arylkyl, aryl, and heteroaryl. Preferably, $R_4$ and $R_5$ are independently selected from hydrogen and alkyl. In one aspect, each of $R_1$, $R_2$, $R_3$, $R_4$, and $R_5$ are independently selected from hydrogen and alkyl.

In another aspect, the compound is selected from the group consisting of:

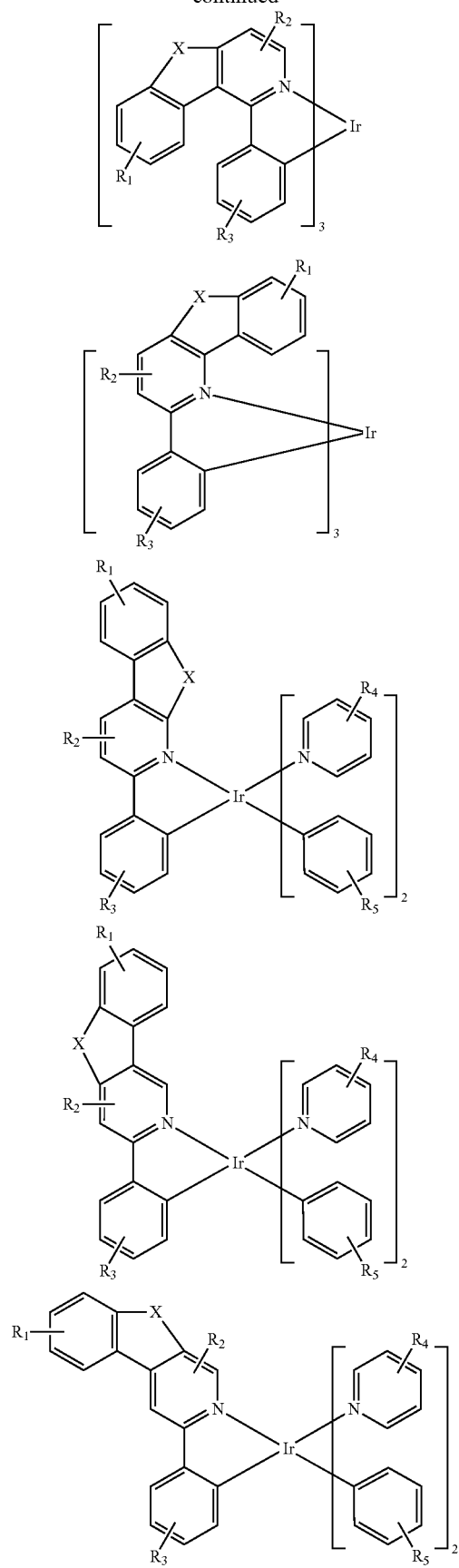
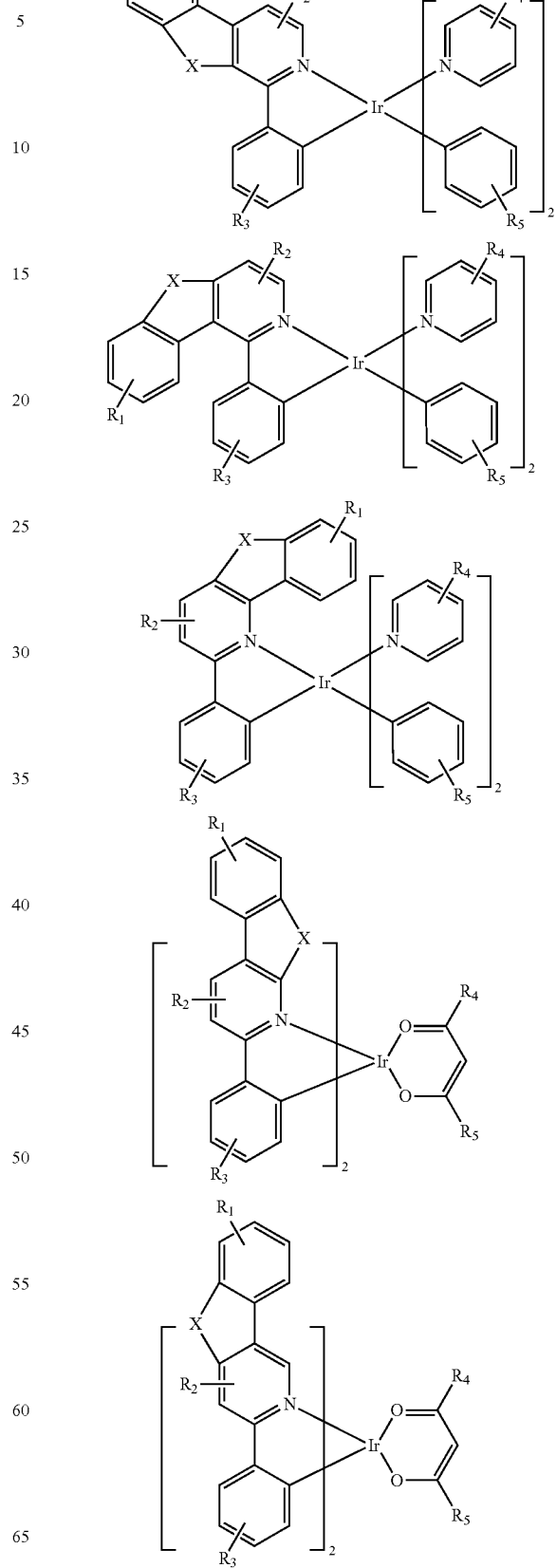

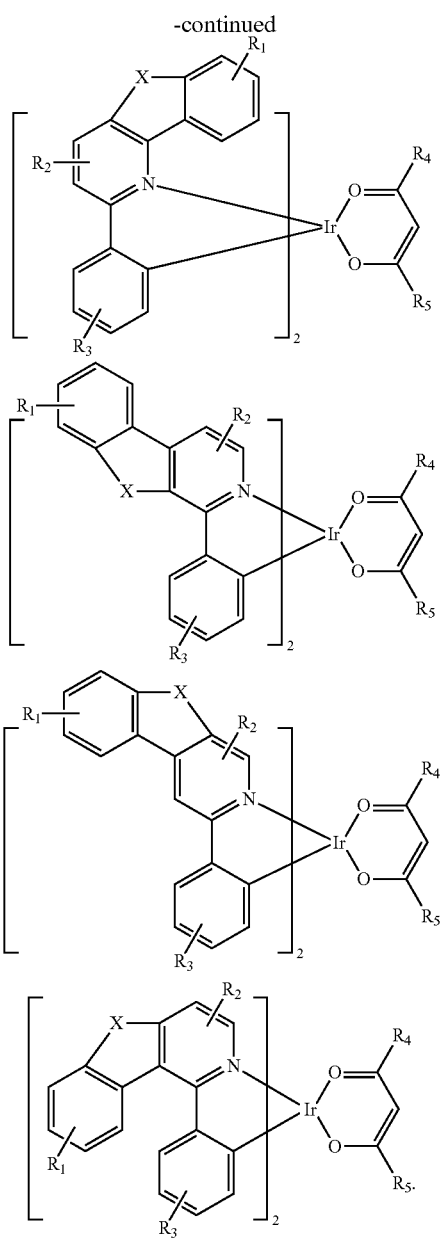

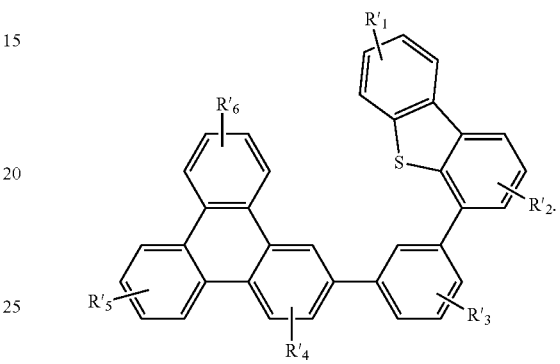

In a particular aspect, compounds comprising a aza DBX ligand and/or a phenylpyridine ligand are preferred. In another aspect, compounds comprising an aza DBX and an ancillary ligand, such as acac, are preferred.

Specific examples of the compounds comprising a ligand having FORMULA I are provided, and include Compounds 1-24, 37-96, and 115-150. In one aspect, compounds are provided wherein X is O (i.e., aza dibenzofuran) including Compounds 1-12 and/or Compounds 61-78. In another aspect, compounds are provided wherein X is S (i.e., aza dibenzothiophene) including Compounds 13-24 and/or pr Compounds 79-96. In yet another aspect, compounds are provided wherein X is CRR' (i.e., aza fluorene) including Compounds 37-48 and/or Compounds 155-132. In yet another aspect, compounds are provided wherein X is C=O (i.e., aza fluorenone) including Compounds 49-60 and/or Compounds 133-150.

Additionally, an organic light emitting device is provided. The device comprises an anode, a cathode, and an organic layer disposed between the anode and the cathode. The organic layer further comprises a compound comprising a ligand having FORMULA I, as described above. In particular, the organic layer comprises a compound containing a ligand having the structure II, III, IV, V, VI or VII, as shown above. Specifically, the organic layer comprises a compound selected from the group consisting of Compounds 1-24, 37-96, and 115-150. Preferably, the organic layer is an emissive layer and the compound is an emitting dopant. The emissive layer may further comprise a host. Preferably, the host has the formula:

$R'_1$, $R'_2$, $R'_4$, $R'_5$, and $R'_6$ may represent mono, di, tri, or tetra substitutions, and each of $R'_1$, $R'_2$, $R'_4$, $R'_5$, and $R'_6$ are independently selected from the group consisting of hydrogen, alkyl, and aryl. Selections for the heteroatoms and substituents described as preferred for compounds having FORMULA I are also preferred for use in a device that includes a compound having FORMULA I. These selections include those described for X, A, $R_1$, $R_2$, $R_3$, $R_4$, and $R_5$.

A consumer product is also provided. The product contains a device that has an anode, a cathode, and an organic layer disposed between the anode and the cathode. The organic layer further comprises a compound comprising a ligand having the structure FORMULA I, as discussed above. Selections for the heteroatoms and substituents described as preferred for compounds having FORMULA I are also preferred for use in a device that includes a compound having FORMULA I. These selections include those described for X, A, $R_1$, $R_2$, $R_3$, $R_4$, and $R_5$.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
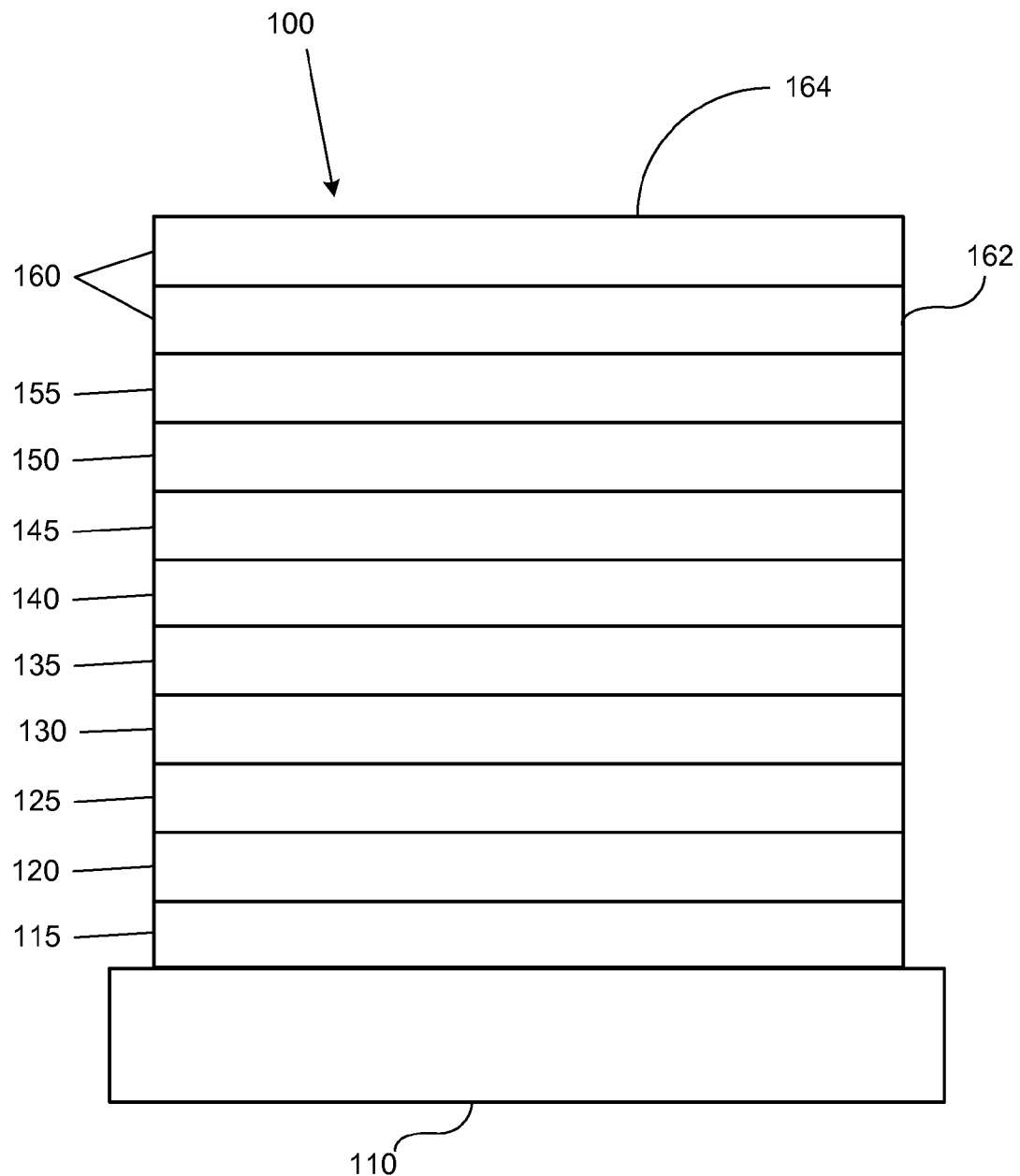
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
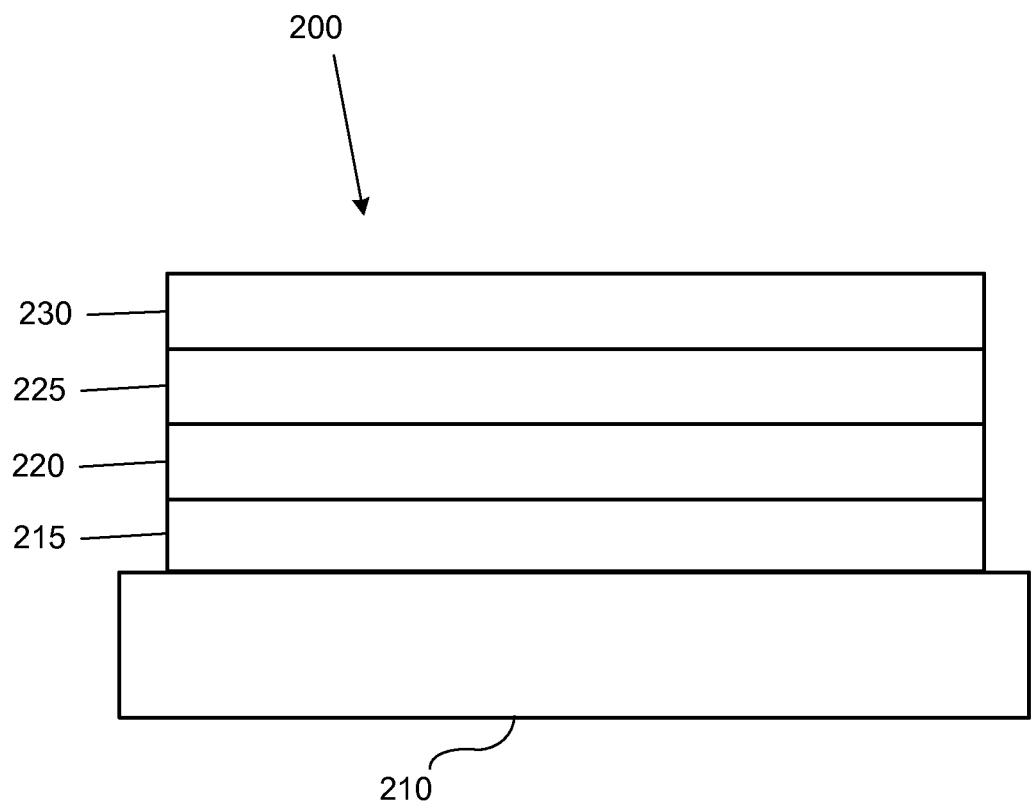
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Figure 3:
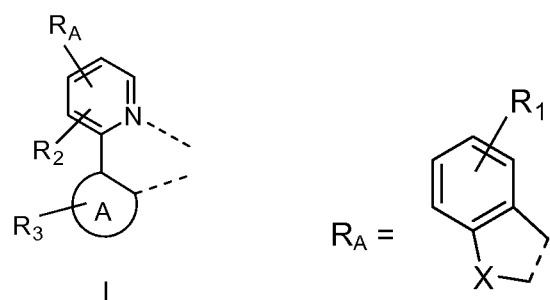
FIG. 3 shows a ligand.
Figure 4:
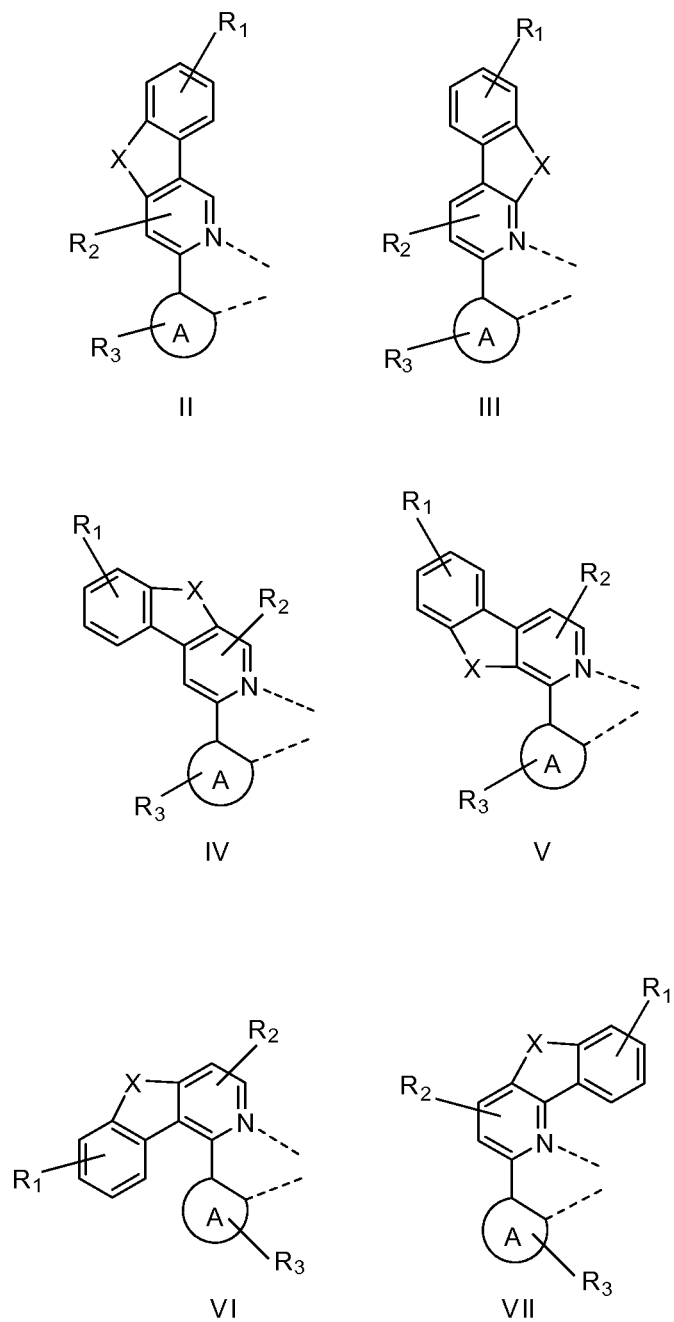
FIG. 4 shows exemplary aza DBX ligands.

A new class of compounds are provided herein, the compounds comprising a ligand having a novel structure (illustrated in FIG. 3). These compounds may be advantageously used in phosphorescent organic light emitting devices. Preferably, these compounds may be used as an emitting dopant in the emissive layer. In particular, the novel ligands having FORMULA 1 consist of a phenylpyridine ligand wherein the pyridine ring has been replaced with an aromatic aza group to generate a novel structure (herein referred to as an "aza DBX" or an "aza dibenzo-substituted" ligand). Aza dibenzo-substituted ligands include aza dibenzofuran, aza dibenzothiophene, aza fluorene, aza fluorenone, aza carbazole, and aza dibenzoselenophene. The compounds provided herein contain an aza DBX ligand where the X represents a chemical group substituent within the aza structure. The substituent can be used to tune the properties of the compound to provide more desirable properties (e.g., color or stability). For example, substituting the aza DBX ligand with a heteroatom, such as O, S or N, may alter the electrochemical and photophysical properties of the compound.

Additionally, the compounds provided herein may have various properties based on the particular ligand structure. In particular, "flipping" the ligand so that the ligand has the same atomic make-up but a different orientation may influence the overall properties of the compound comprising the ligand (i.e., II compared to III, IV compared to V, and VI compared to VII). For example, Compound 1 and Compound 8 both contain an aza DBX ligand wherein X is O (i.e. aza dibenzofuran), but the ligands have a different orientation in Compound 1 compared to Compound 2 and consequently, there is a red-shift between these compounds.

Iridium complexes containing aza dibenzo-substituted ligands may demonstrate many desirable characteristics. Without being bound by theory, it is thought that the novel compounds provided herein may be more stable emitters in PHOLEDs. The LUMO of phenylpyridine iridium complexes is normally localized on the ligand, whereas the compounds provided herein provide better electron destabilization via the aza dibenzo-substituted ligand. Therefore, these compounds may be considered more stable to electrons resulting in a more stable emitters. In addition, these compounds may also provide devices having improved lifetime and lower operating voltage.

The compounds provided herein comprise a ligand having the structure:

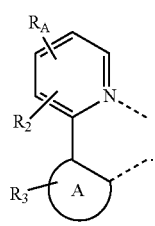

FORMULA I

A is a 5-membered or 6-membered aromatic or heteroaromatic ring. In one aspect, A is a 6 membered ring wherein, preferably, A is benzene. In another aspect, A is a 5 membered ring wherein, preferably, A is selected from the group consisting of furan, thiophene, and pyrrole. Examples of 5-membered ring which may be used as the A ring include, for example, furan, thiophene, pyrrole, azole, thiazole, dithiolane, triazole, dithiazole, and tetrazole.

$R_A$ is a substituent having the structure

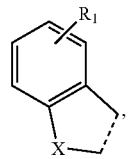

wherein the substituent is fused to the pyridine ring of FORMULA I. The dashed line present in the structure indicates where the substituent is joined to the pyridine ring of FORMULA I. X is selected from the group consisting of CRR', C=O, BR, NR, O, S, and Se. R and R' are independently selected from hydrogen and alkyl. $R_1$, $R_2$, and $R_3$ may represent mono, di, tri, or tetra substitutions; each of $R_1$, $R_2$, and $R_3$ are independently selected from the group consisting of hydrogen, alkyl, alkoxy, amino, alkenyl, alkynyl, arylkyl, aryl, and heteroaryl. The ligand is coordinated to a metal having an atomic weight greater than 40. Preferably, the metal is Ir.

In one aspect, compounds provided which comprise a ligand having the structure:

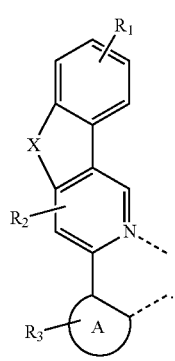

II

In another aspect, compounds provided which comprise a ligand having the structure:

In yet another aspect, compounds provided which comprise a ligand having the structure:

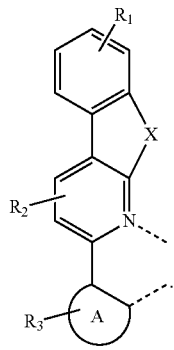
III

In yet another aspect, compounds provided which comprise a ligand having the structure:

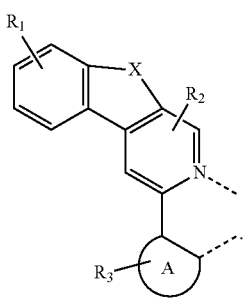
IV

In yet another aspect, compounds provided which comprise a ligand having the structure:

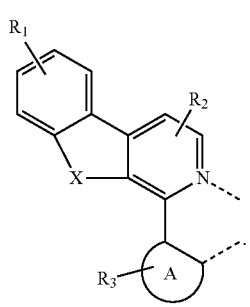
V

In yet another aspect, compounds provided which comprise a ligand having the structure:

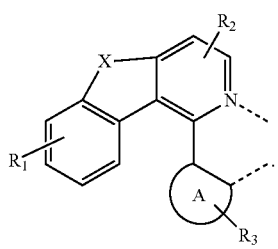
VI

In yet a further aspect, compounds provided which comprise a ligand having the structure:

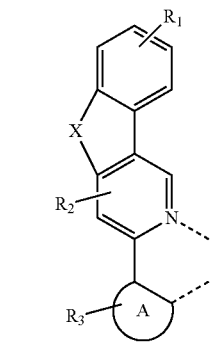
VII

In one aspect, the compound has the formula $(L)_n(L')_{3-n}Ir$. L is selected from the group consisting of

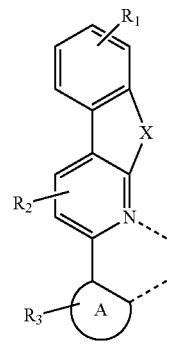
II

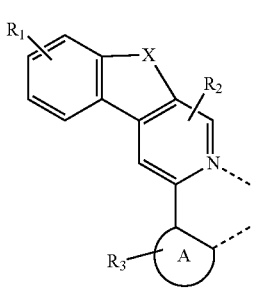
III

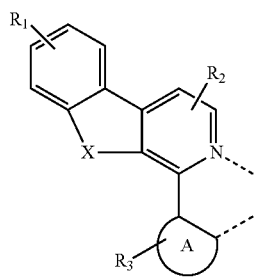
IV

V

-continued

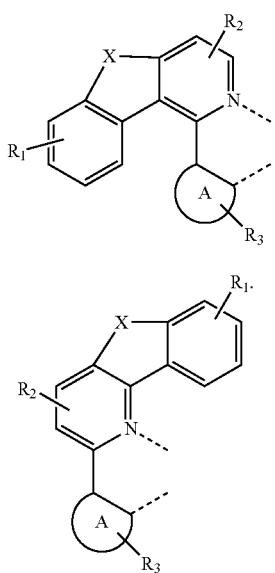

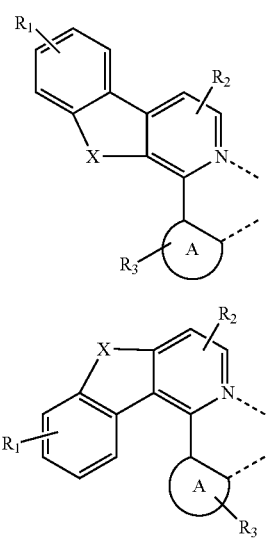

L' is selected from the group consisting of:

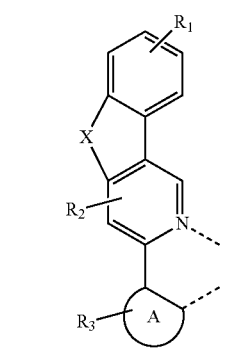

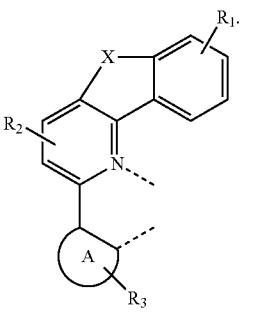

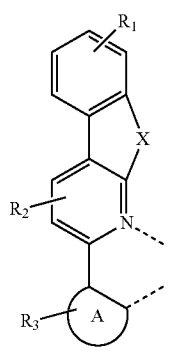

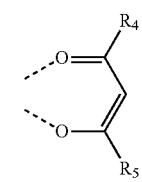

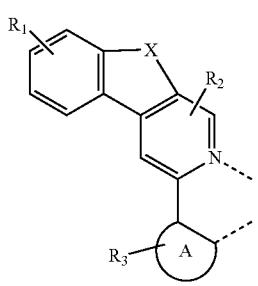

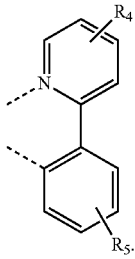

n is 1, 2, or 3. In one aspect, n is 3. When n is 3, the compound is a homoleptic compound. In another aspect, n is 2. In yet another aspect, n is 1. When n is 1 or 2, the compound is a heteroleptic compound.

$R_4$ and $R_5$ may represent mono, di, tri, or tetra substitutions; and $R_4$ and $R_5$ are independently selected from the group consisting of hydrogen, alkyl, alkoxy, amino, alkenyl, alkynyl, arylkyl, aryl, and heteroaryl. Preferably, $R_4$ and $R_5$ are independently selected from hydrogen and alkyl.

The novel compounds provided herein include heteroleptic and homoleptic metal complexes. In particular, compounds are provided wherein the compound is selected from the group consisting of:

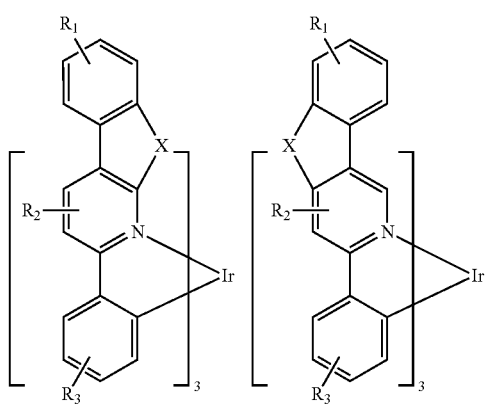
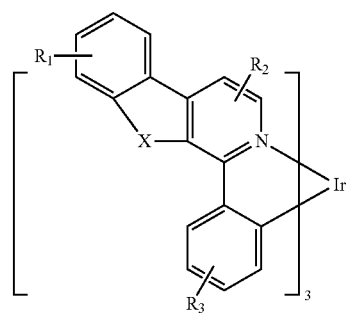
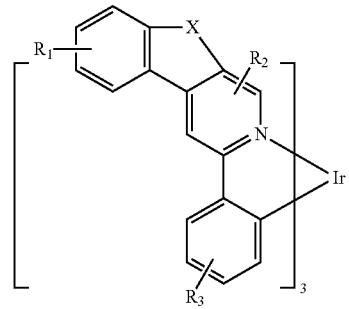
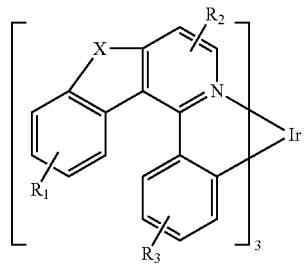
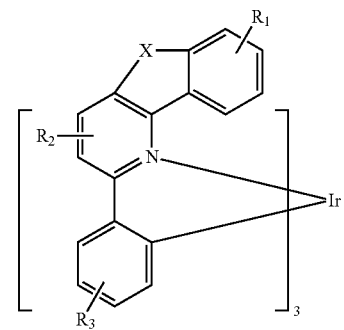
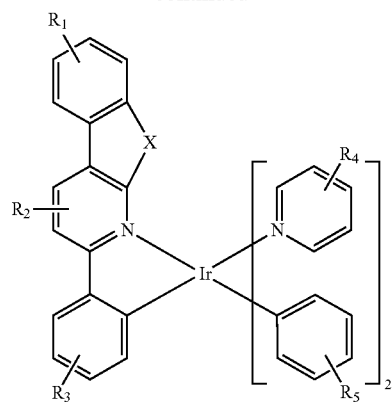
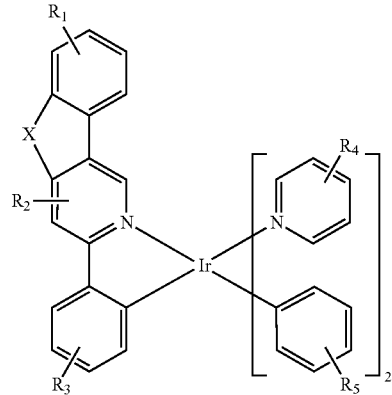
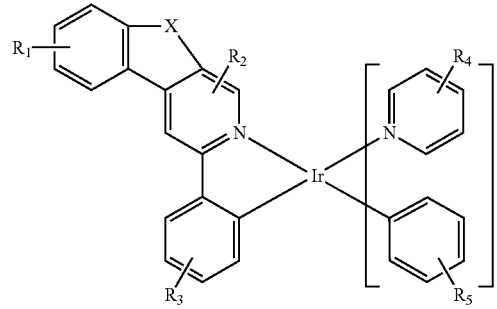
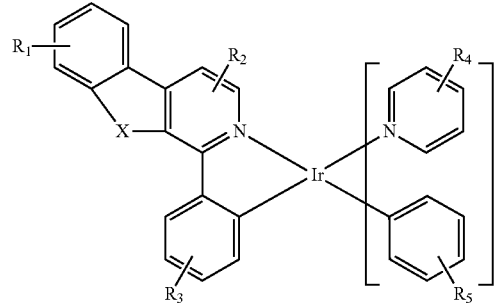
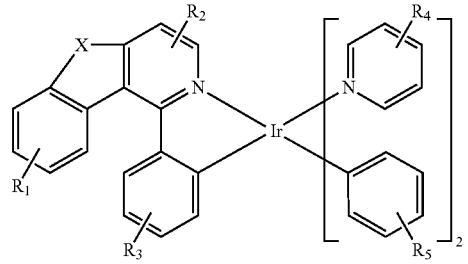

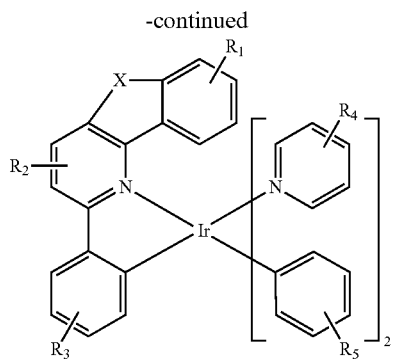
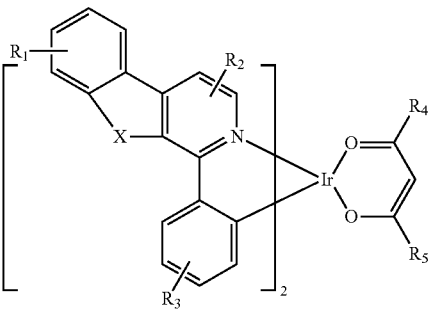
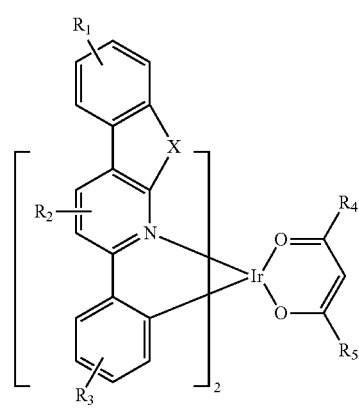
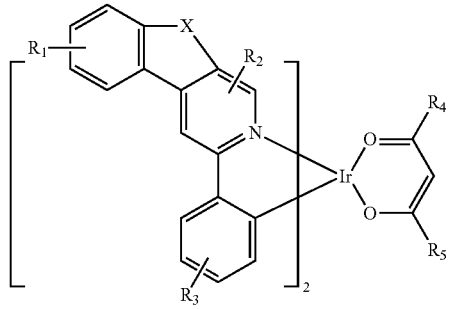
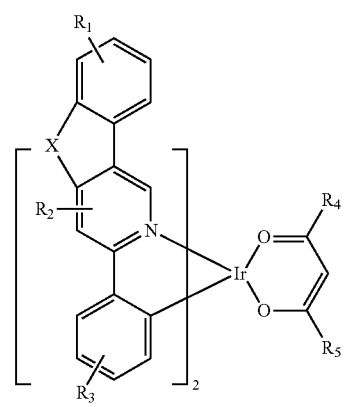
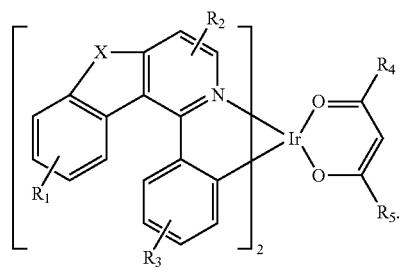
In one aspect, compounds comprising a phenylpyridine ligand, a pyridyl aza DBX ligand, or both ligands are preferred. These compounds include both homoleptic and heteroleptic compounds comprising the novel ligand. In particular, compounds selected from the group consisting of:
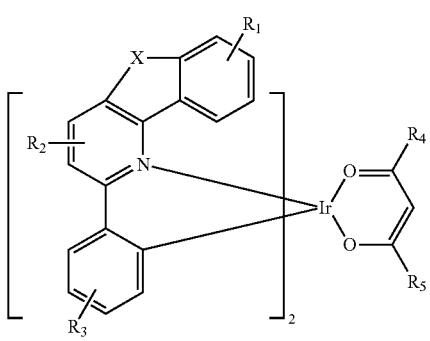
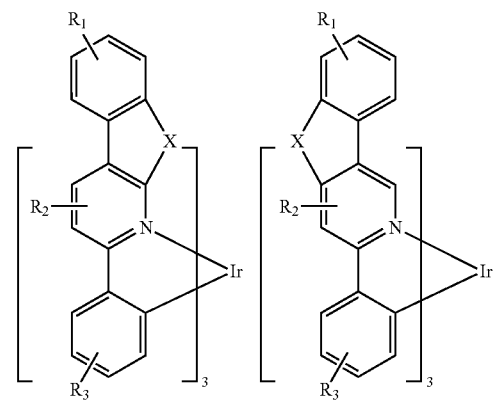

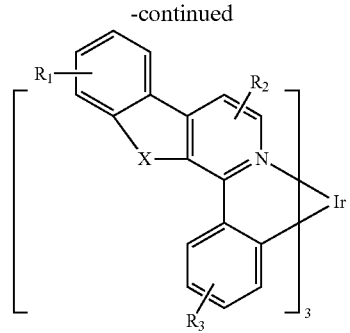
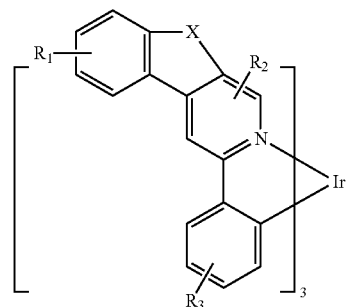
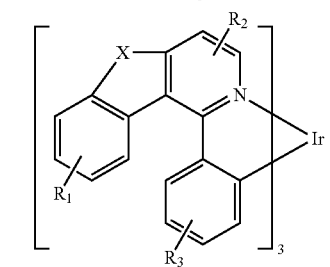
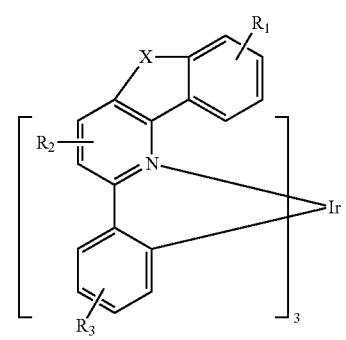
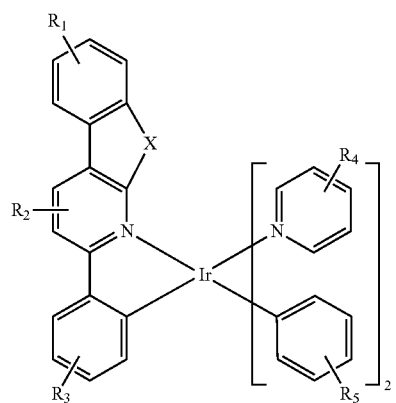
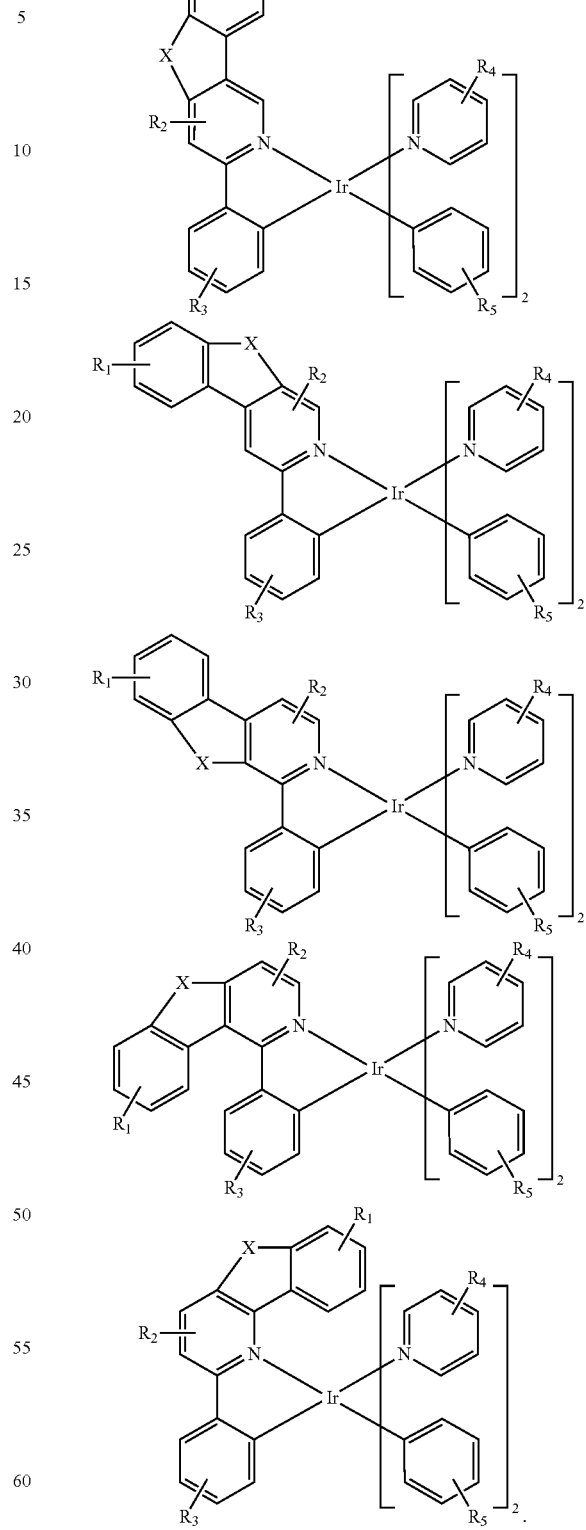
In another aspect, compounds comprising pyridyl aza dibenzo-substituted ligands and an ancillary ligand, such as acac, are preferred. In particular, compounds selected from the group consisting of:

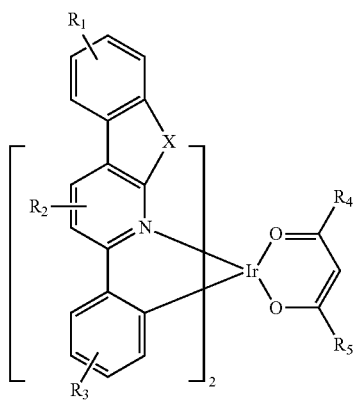
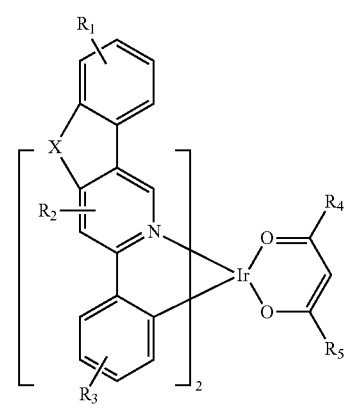
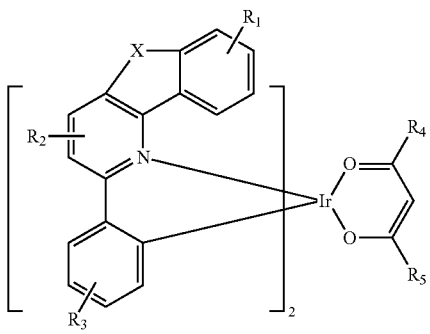
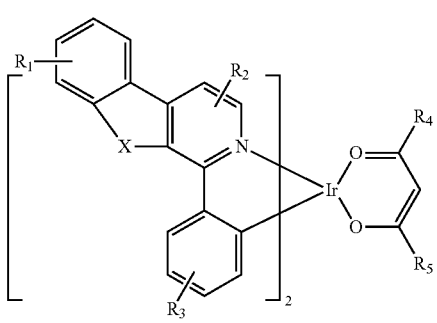
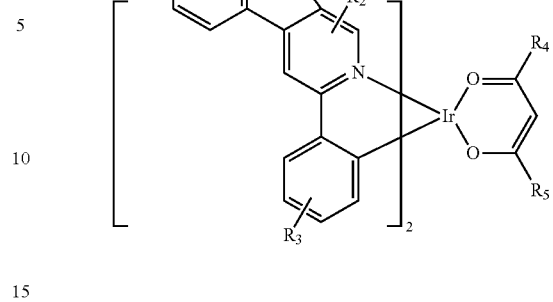
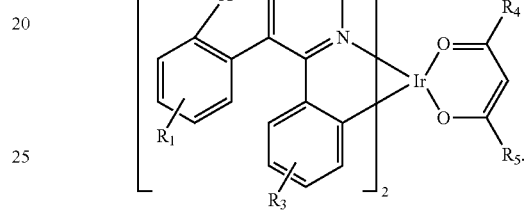
Specific examples of the novel compounds comprising a ligand having FORMULA I are provided, and include compounds selected from the group consisting of:
Compound 1
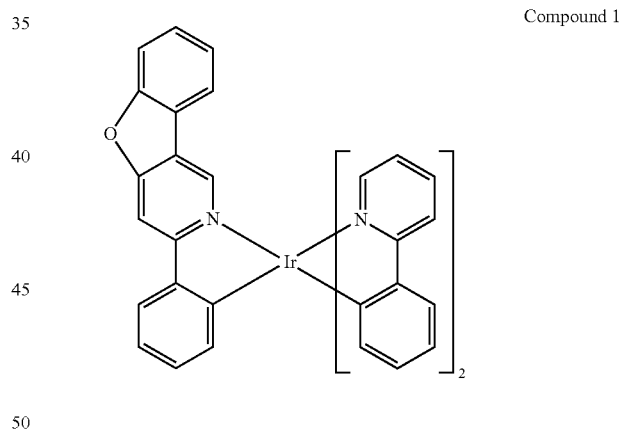
Compound 2
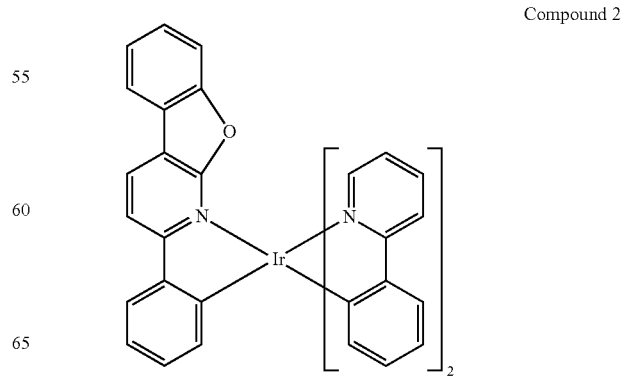

Compound 3
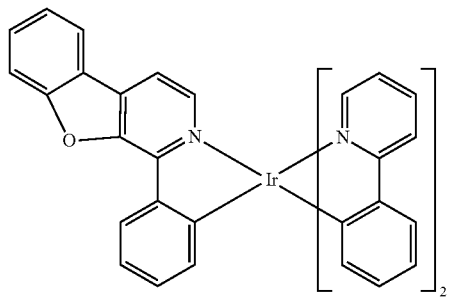
Compound 4
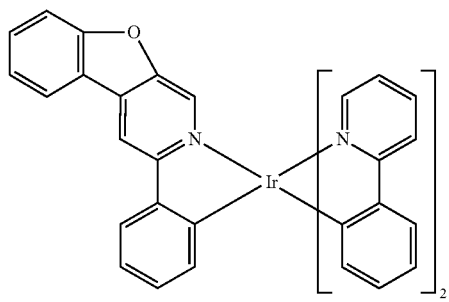
Compound 5
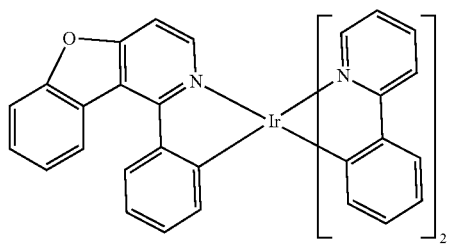
Compound 6
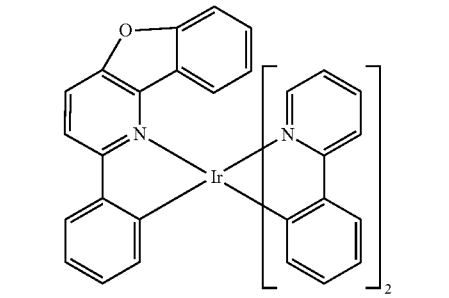
Compound 7
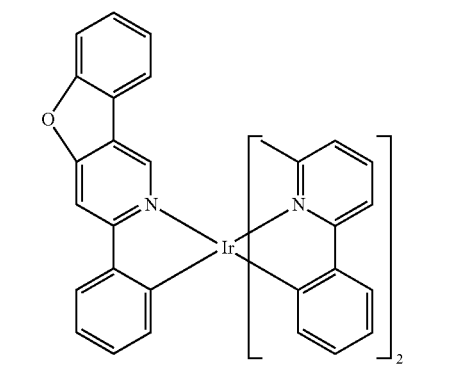
Compound 8
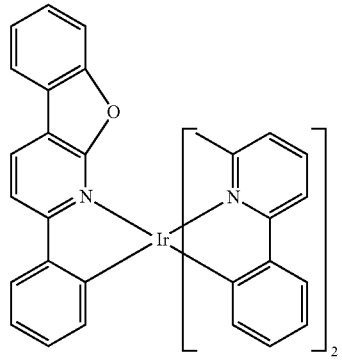
Compound 9
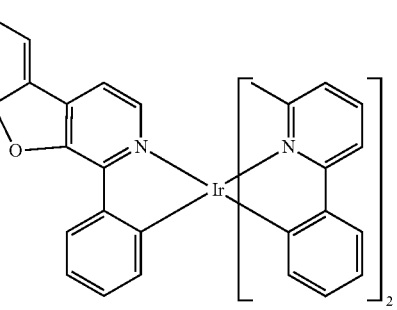
Compound 10
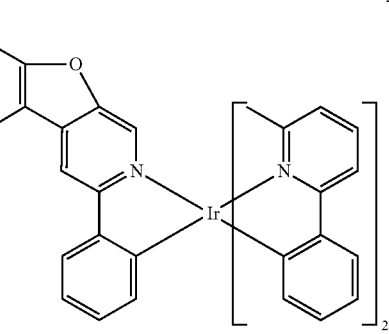
Compound 11
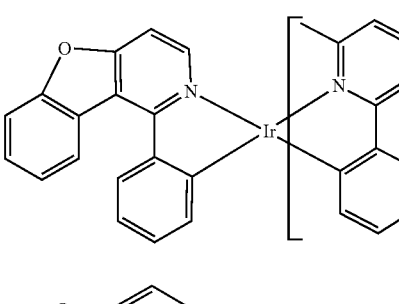
Compound 12

Compound 13
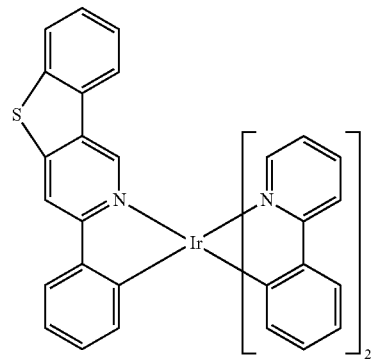
Compound 14
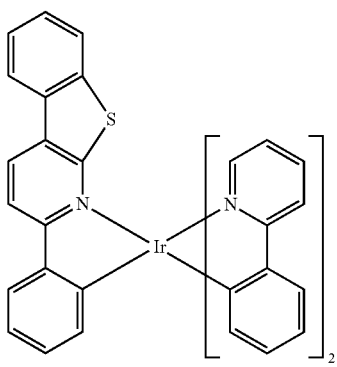
Compound 15
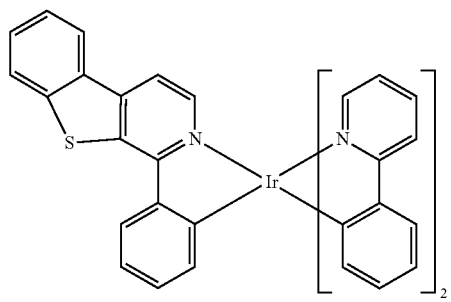
Compound 16
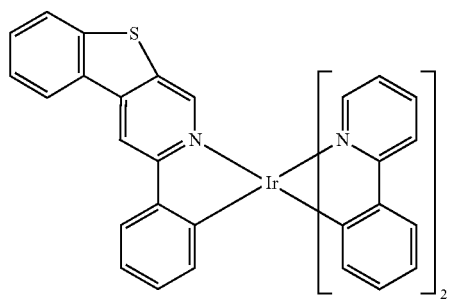
Compound 17
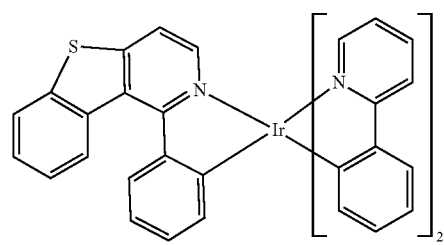
Compound 18
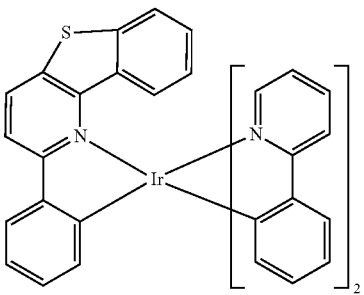
Compound 19
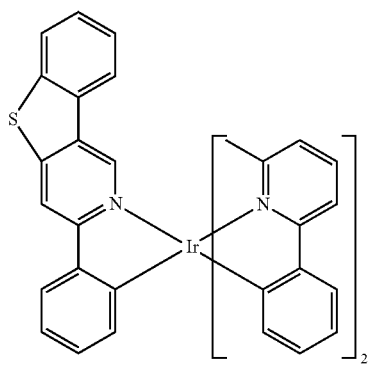
Compound 20
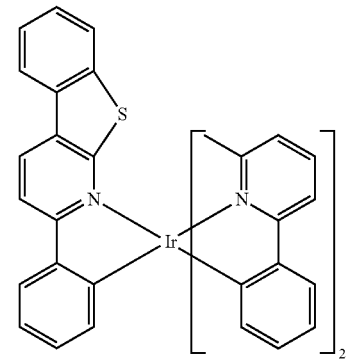
Compound 21
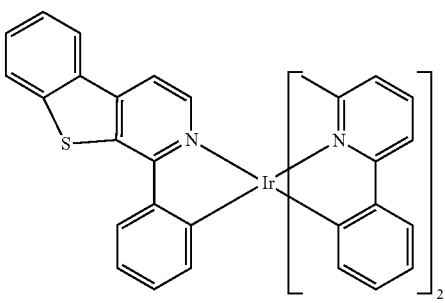
Compound 22
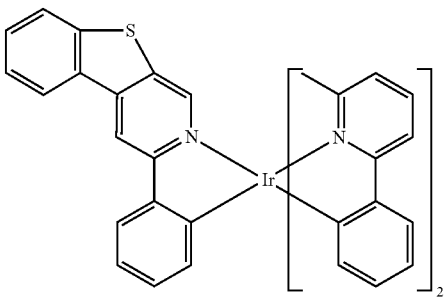

-continued
Compound 23
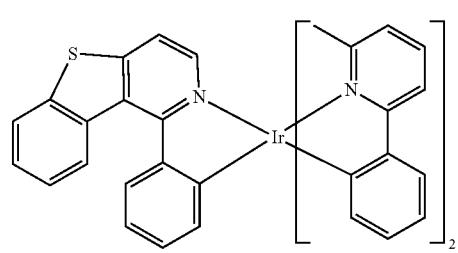
Compound 24
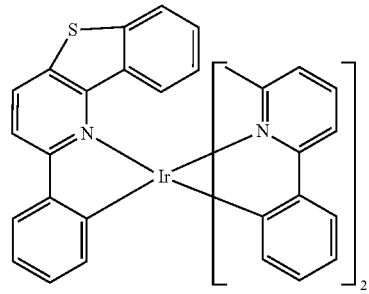
Compound 25
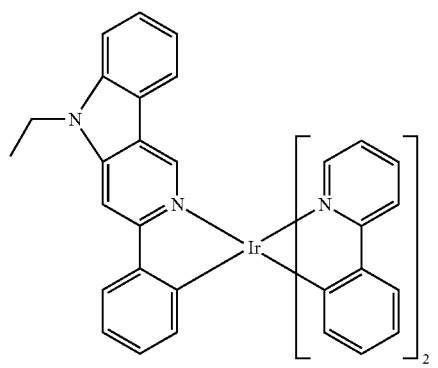
Compound 26
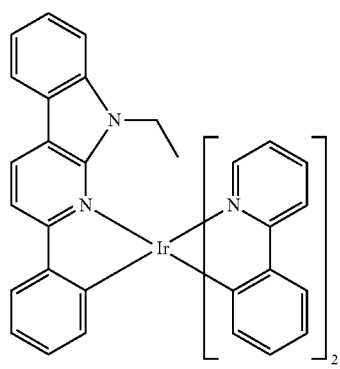
-continued
Compound 27
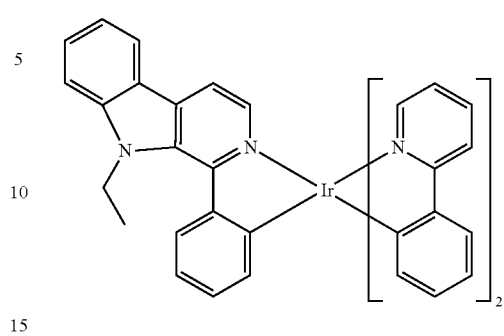
Compound 28
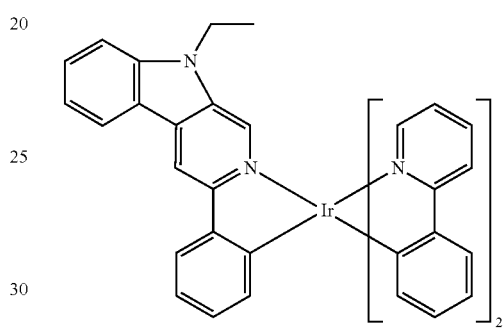
Compound 29
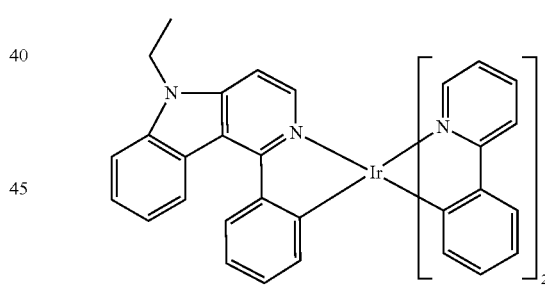
Compound 30
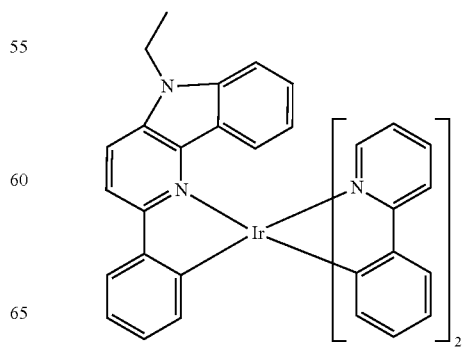

Compound 31
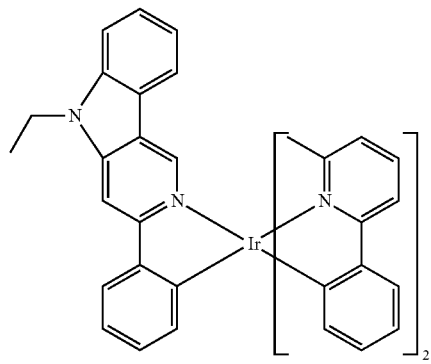
Compound 32
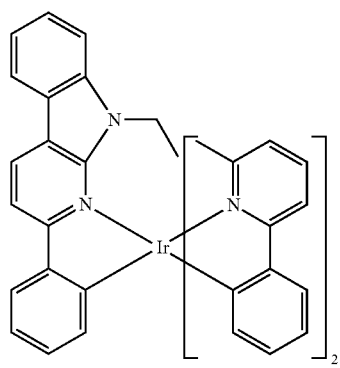
Compound 33
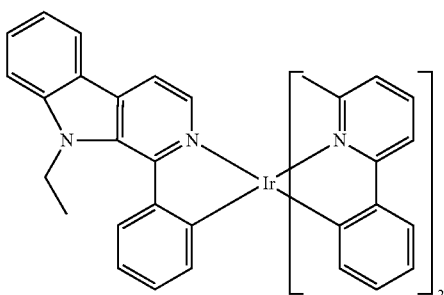
Compound 34
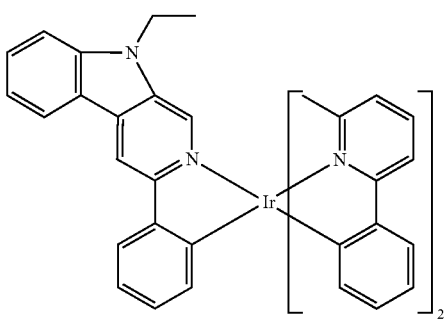
Compound 35
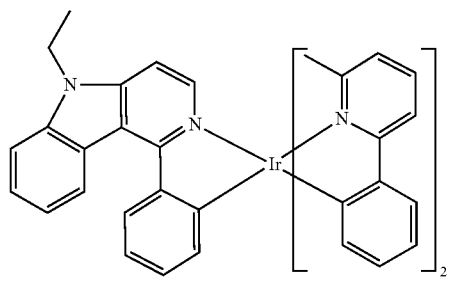
Compound 36
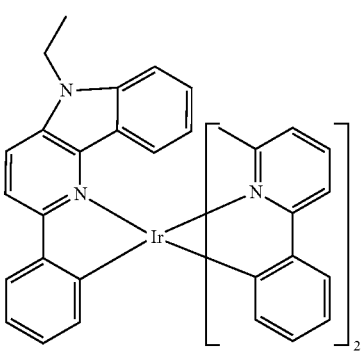
Compound 37
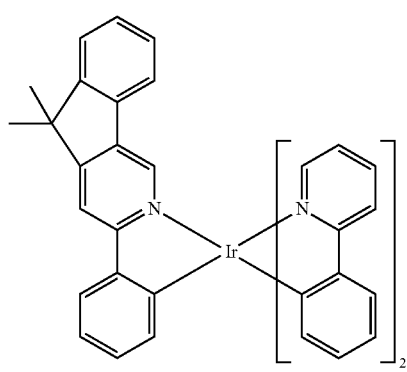
Compound 38
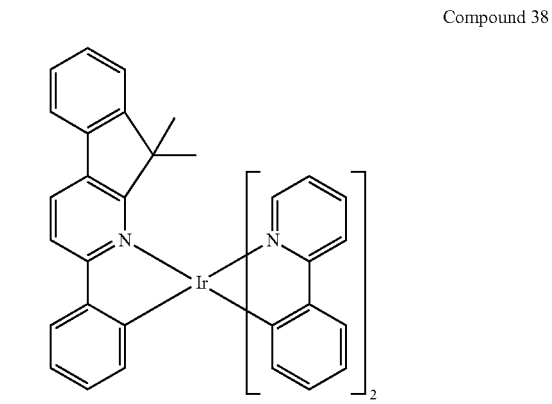

Compound 39
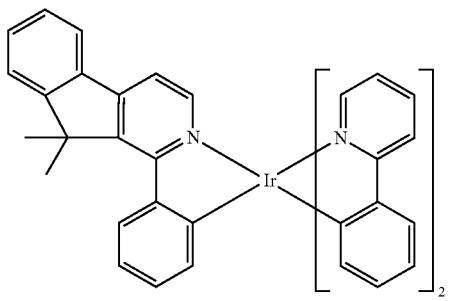
Compound 40
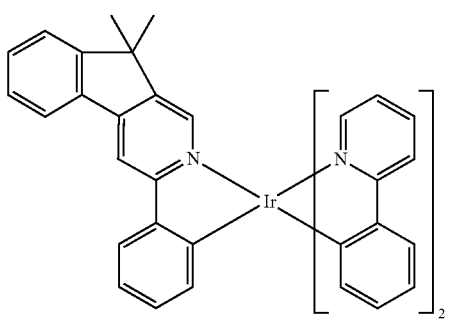
Compound 41
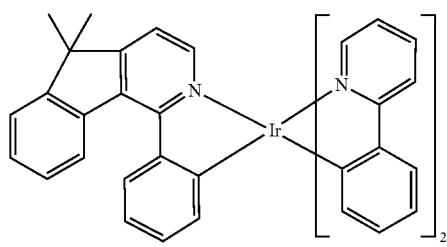
Compound 42
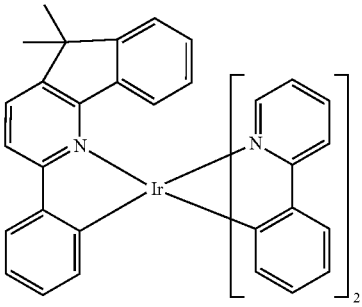
Compound 43
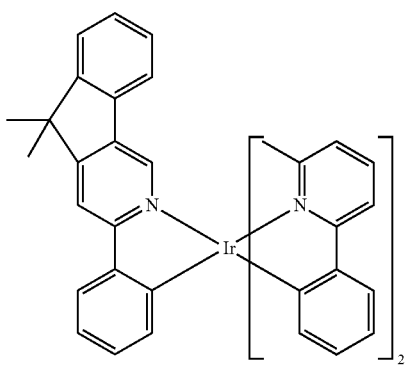
Compound 44
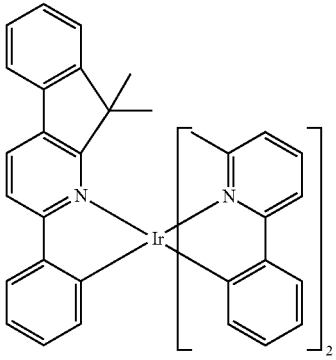
Compound 45
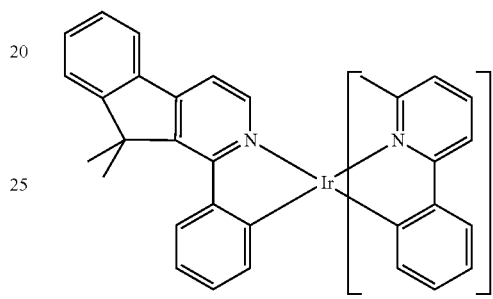
Compound 46
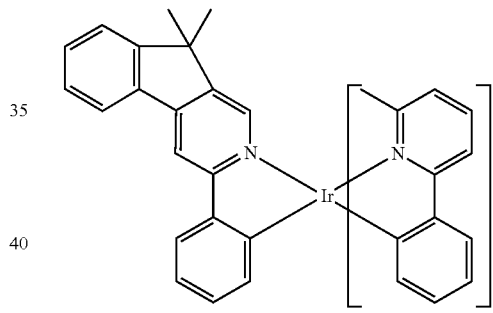
Compound 47
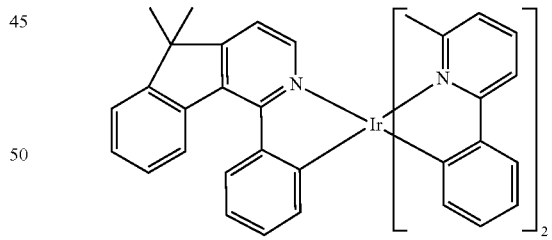
Compound 48

Compound 49
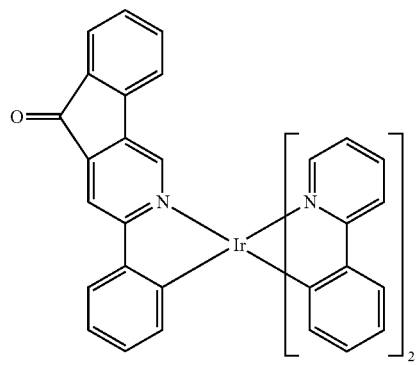
Compound 50
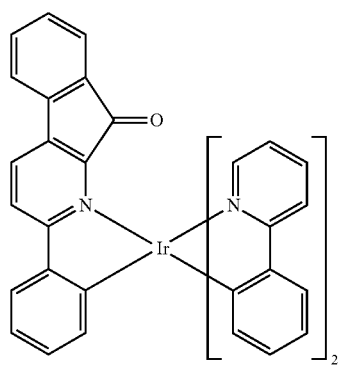
Compound 51
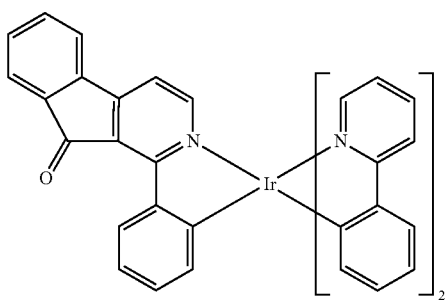
Compound 52
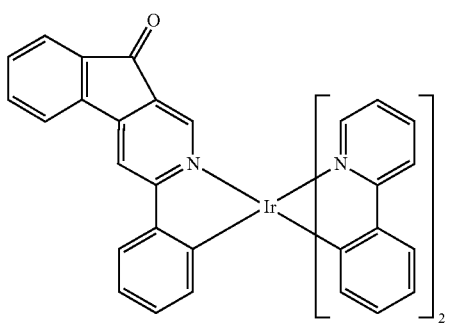
Compound 53
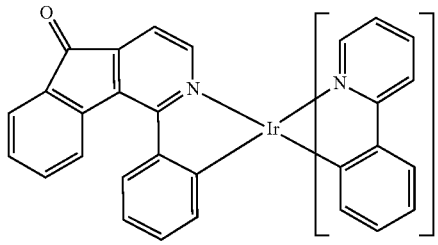
Compound 54
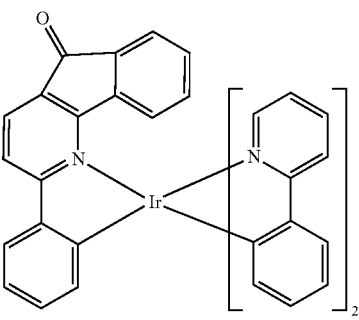
Compound 55
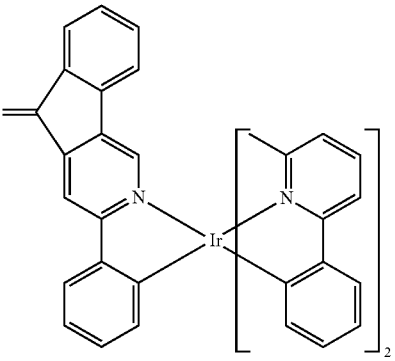
Compound 56
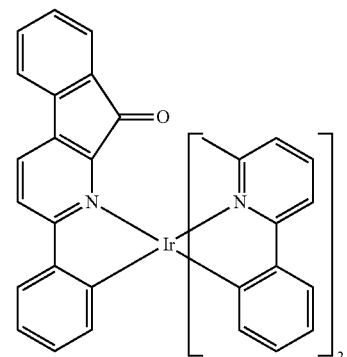
Compound 57
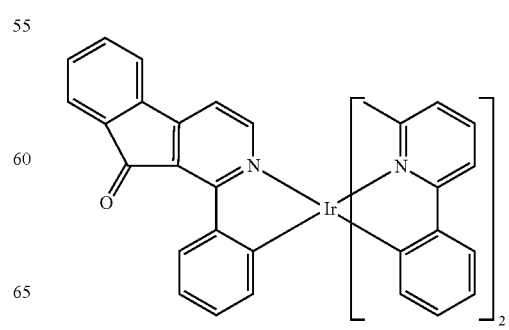

Compound 58
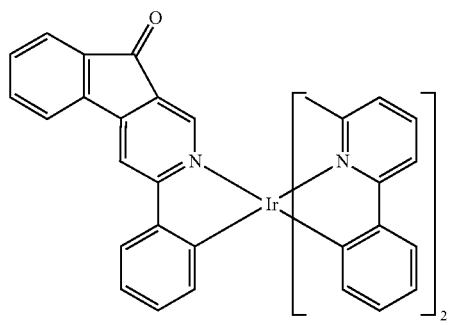
Compound 59
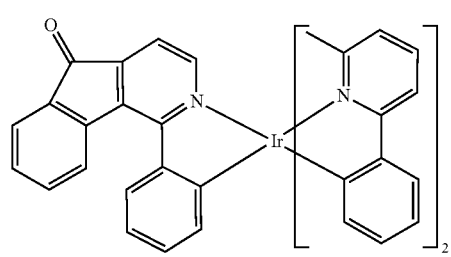
Compound 60
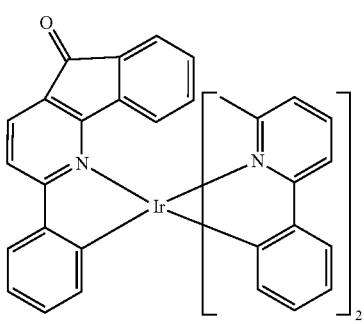
Compound 61
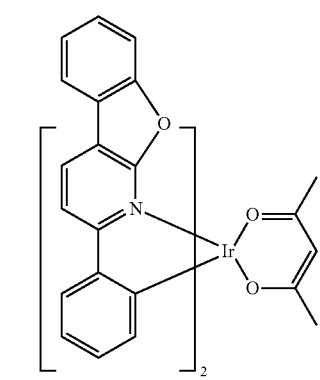
Compound 62
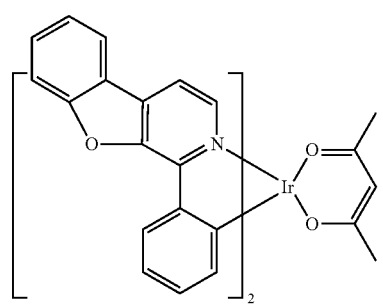
Compound 63
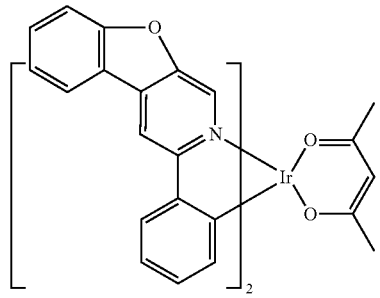
Compound 64
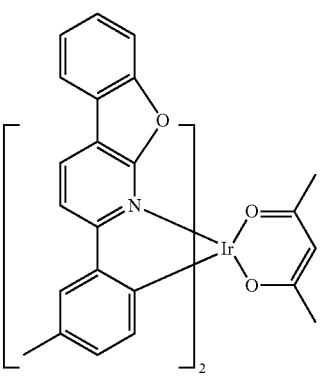
Compound 65
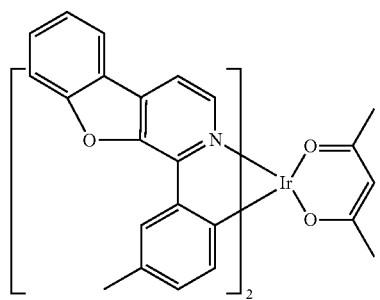
Compound 66
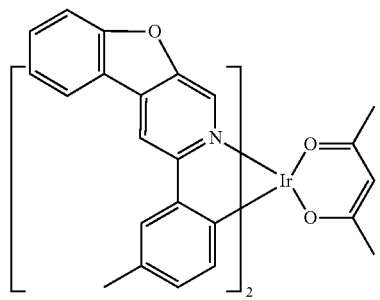
Compound 67
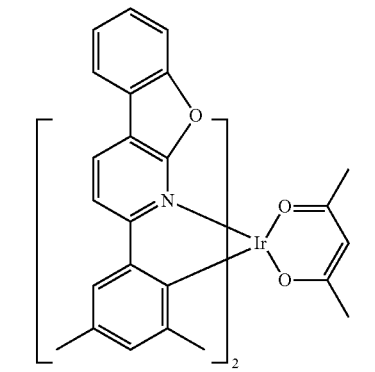

Compound 68
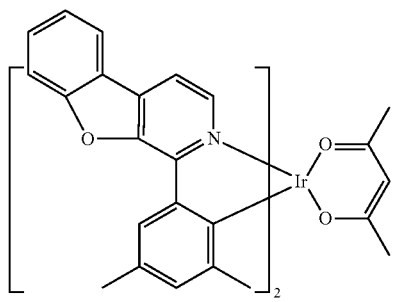
Compound 69
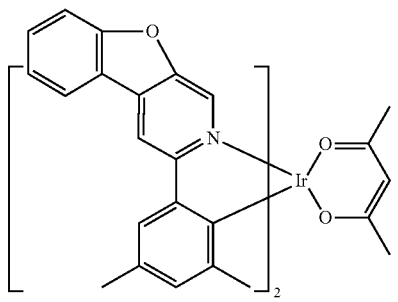
Compound 70
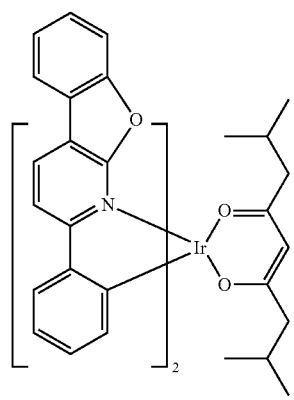
Compound 71
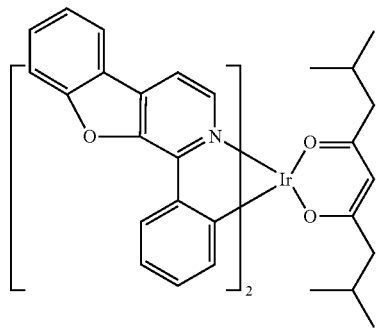
Compound 72
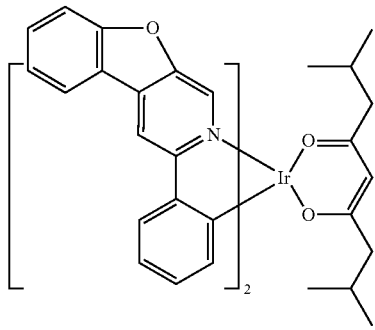
Compound 73
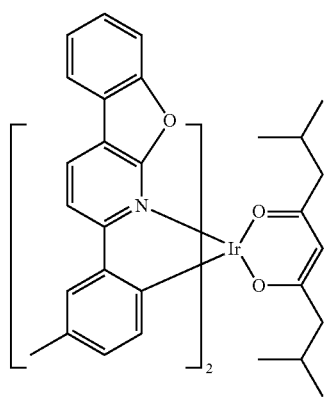
Compound 74
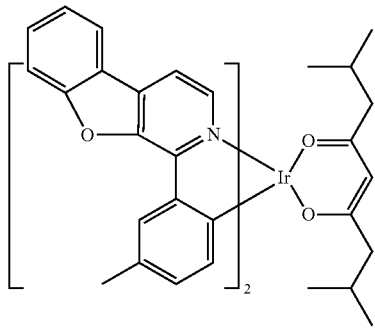
Compound 75
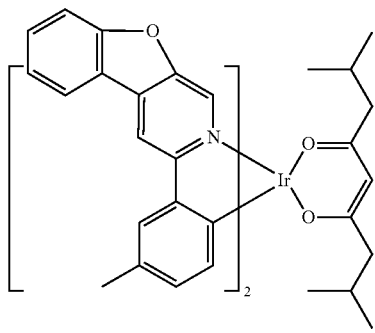

Compound 76
Compound 77
Compound 78
Compound 79
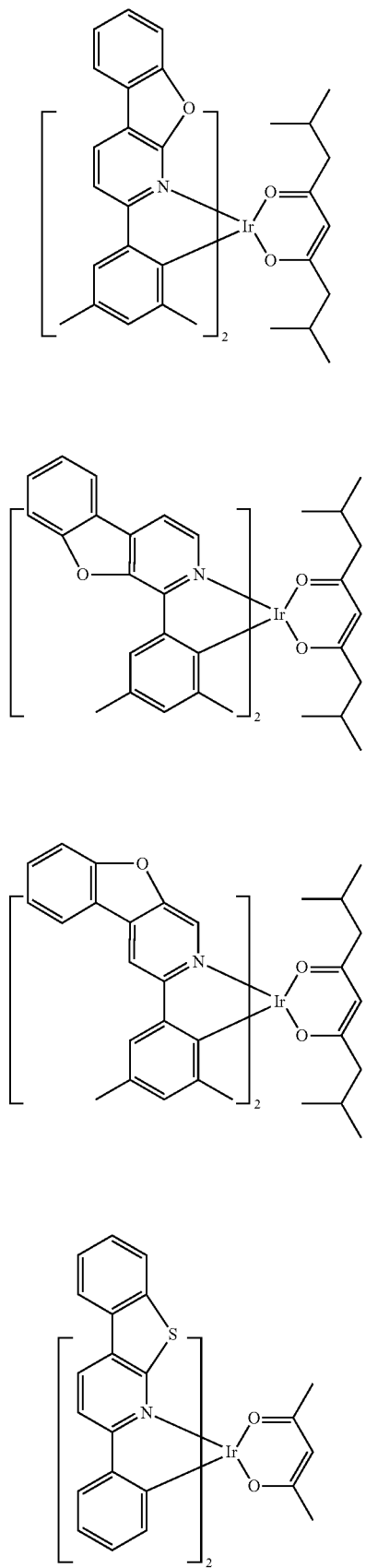
Compound 80
Compound 81
Compound 82
Compound 83
Compound 84
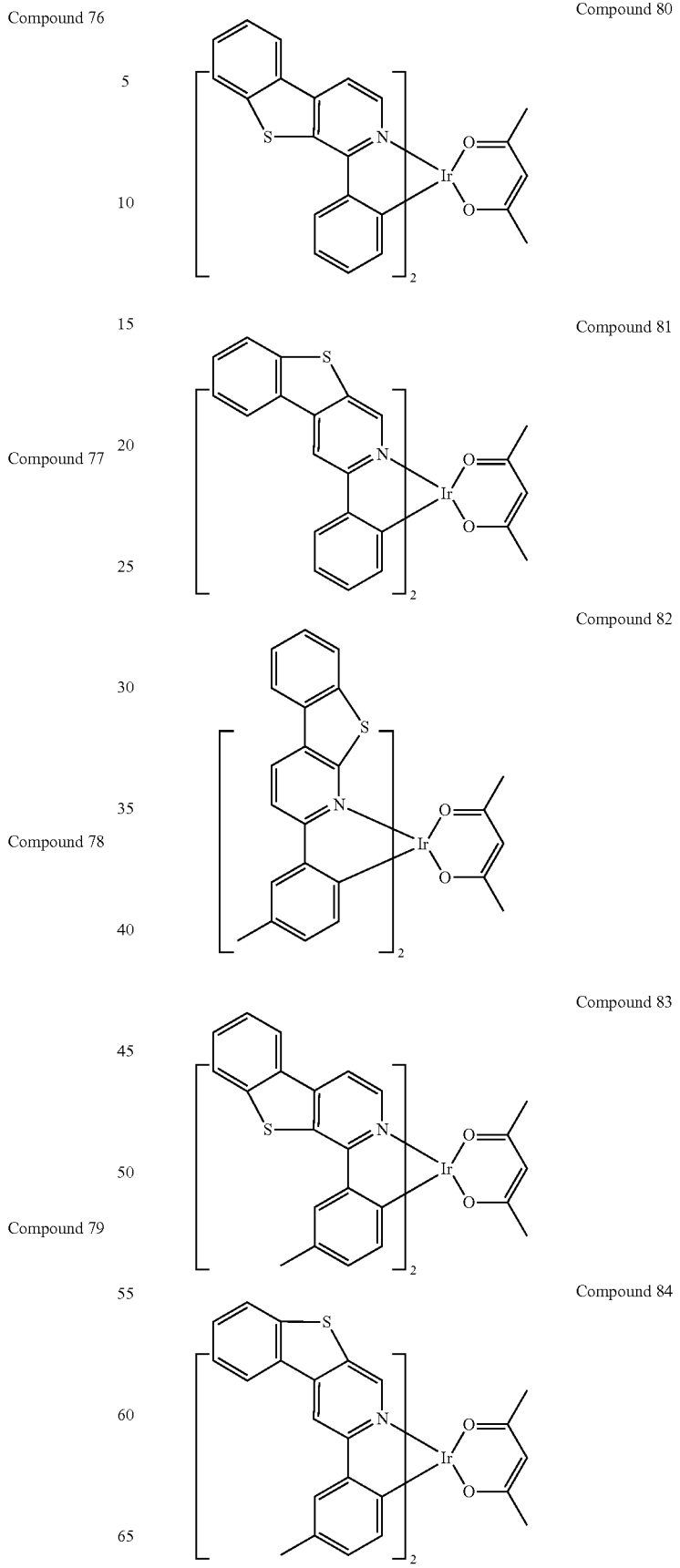

-continued
Compound 85
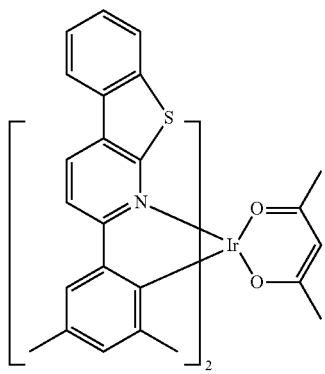
Compound 86
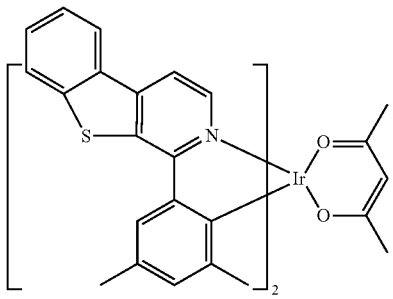
Compound 87
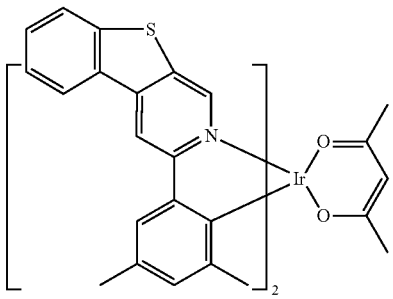
Compound 88
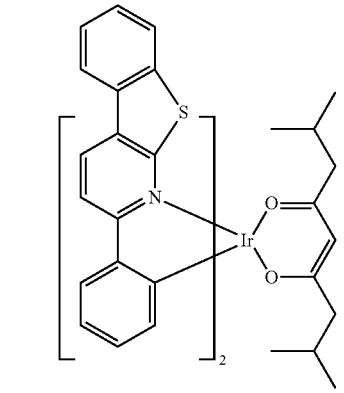
-continued
Compound 89
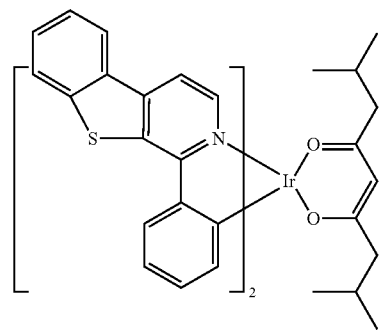
Compound 90
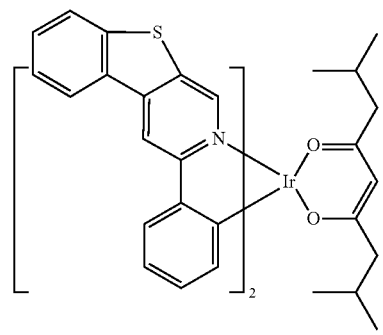
Compound 91
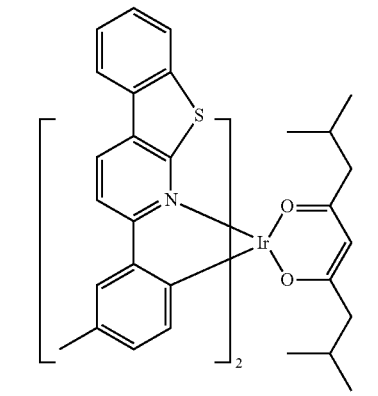
Compound 92
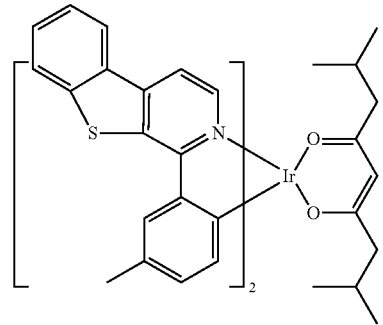

Compound 93
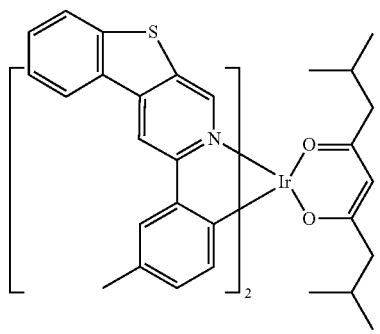
Compound 94
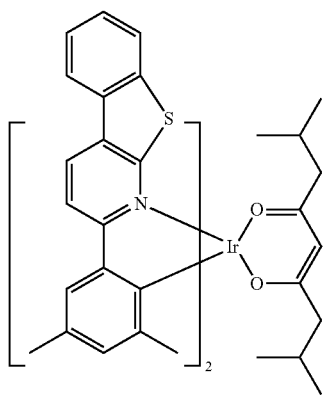
Compound 95
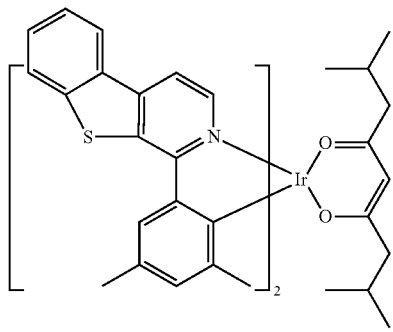
Compound 96
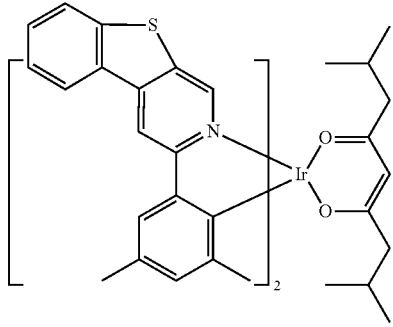
Compound 97
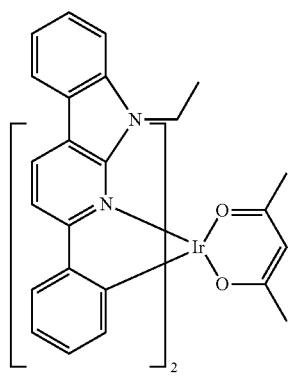
Compound 98
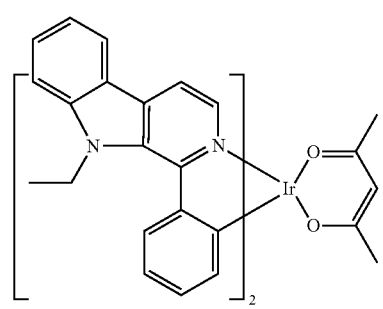
Compound 99
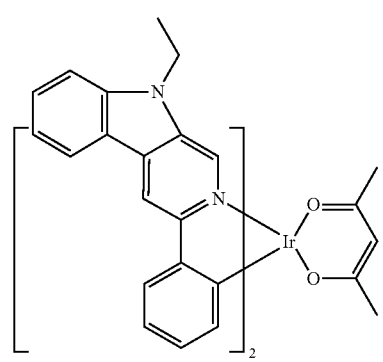
Compound 100
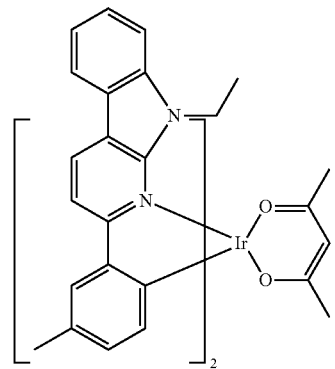

Compound 101
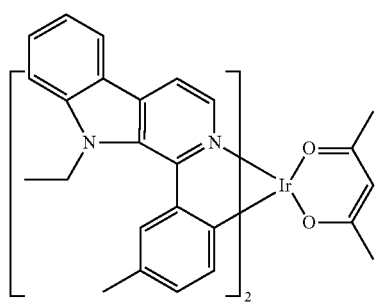
Compound 102
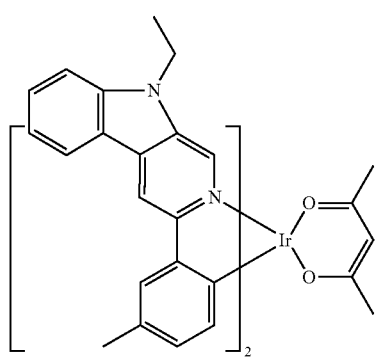
Compound 103
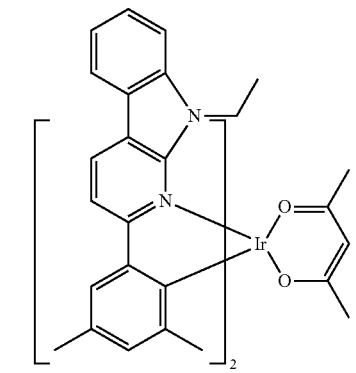
Compound 104
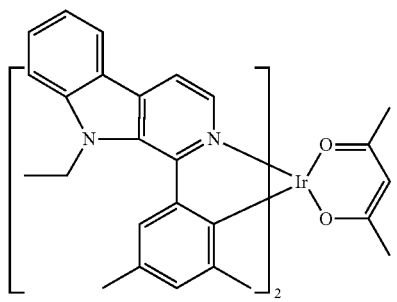
Compound 105
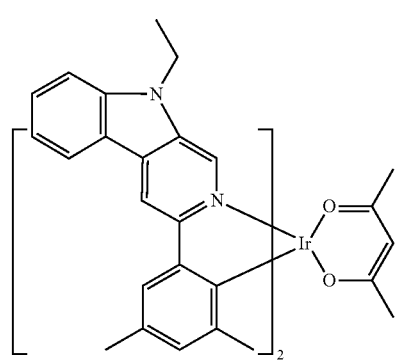
Compound 106
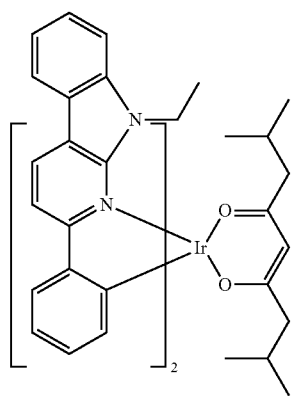
Compound 107
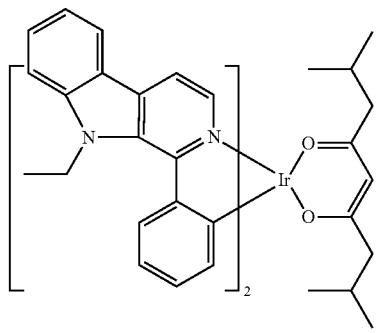
Compound 108
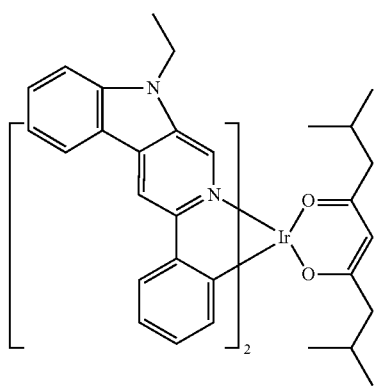

Compound 109
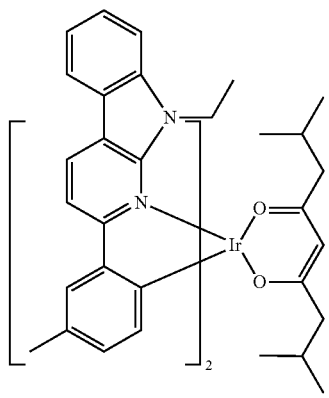
Compound 110
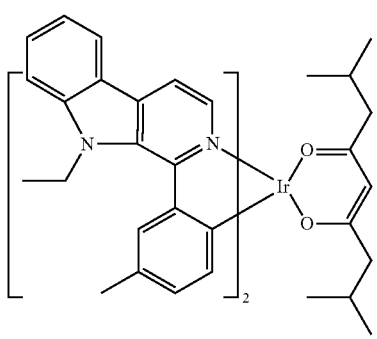
Compound 111
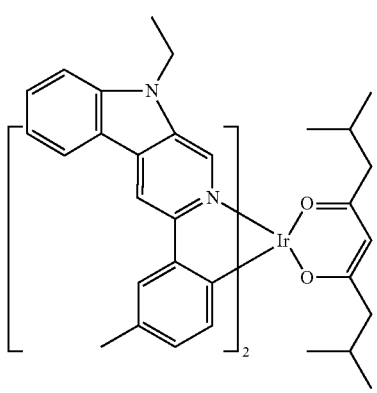
Compound 112
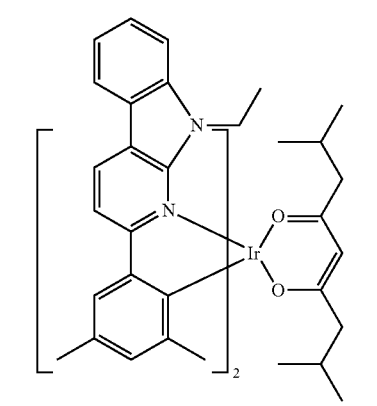
Compound 113
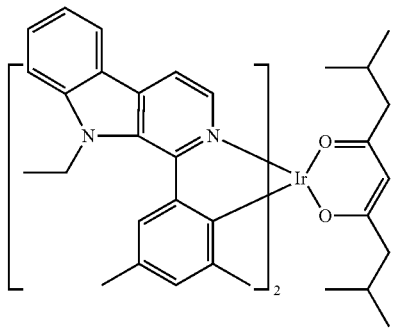
Compound 114
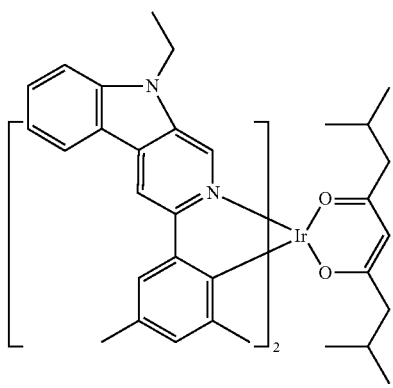
Compound 115
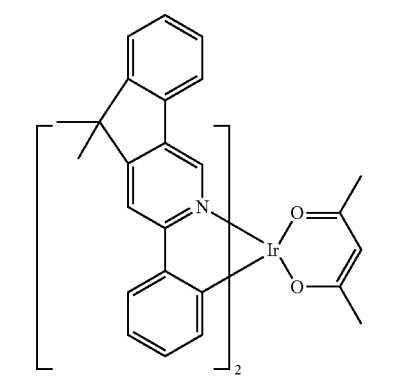
Compound 116
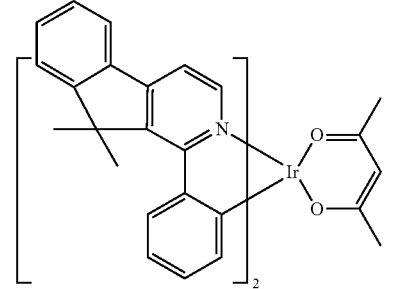

Compound 117
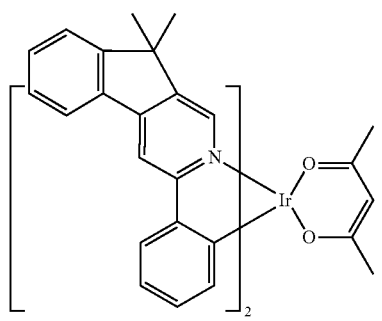
Compound 118
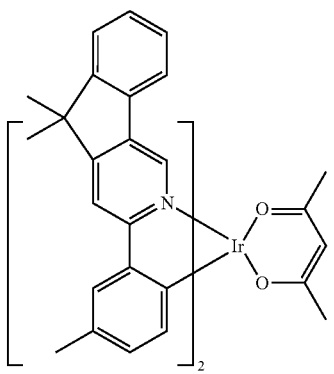
Compound 119
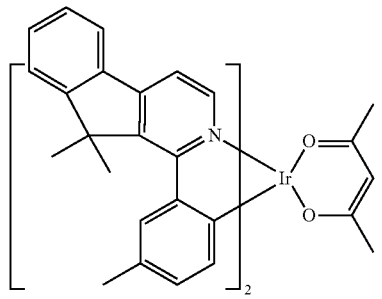
Compound 120
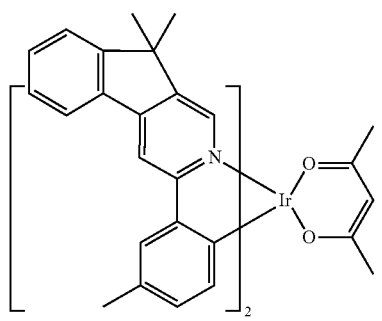
Compound 121
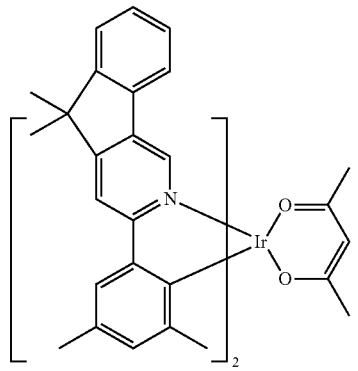
Compound 122
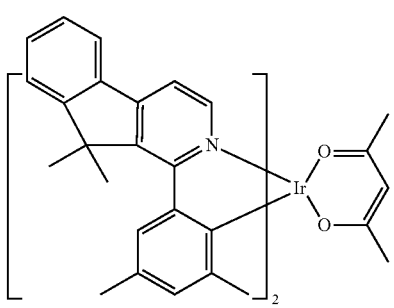
Compound 123
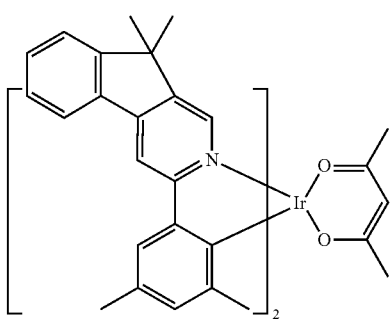
Compound 124
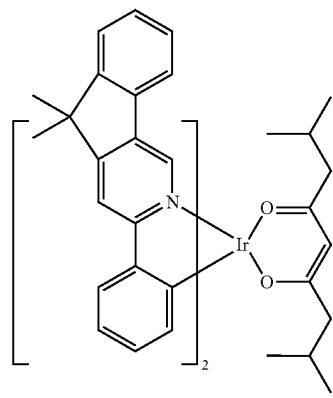

Compound 125
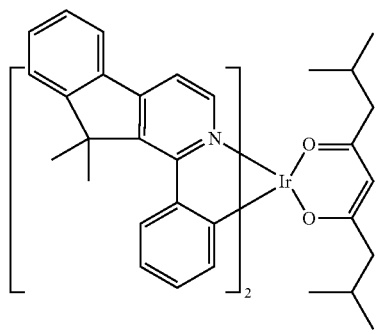
Compound 129
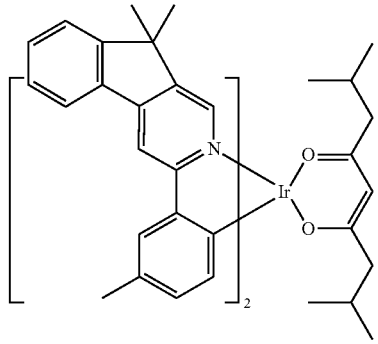
Compound 126
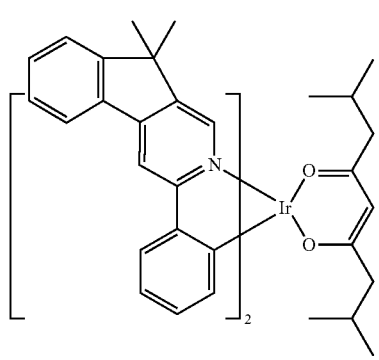
Compound 130
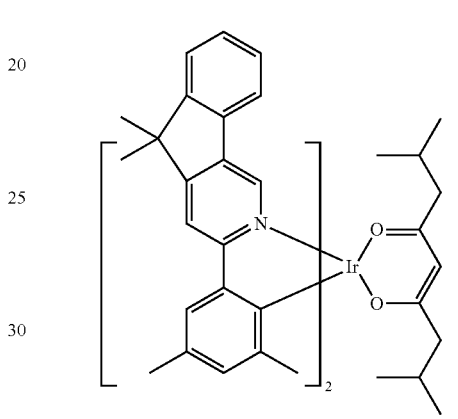
Compound 127
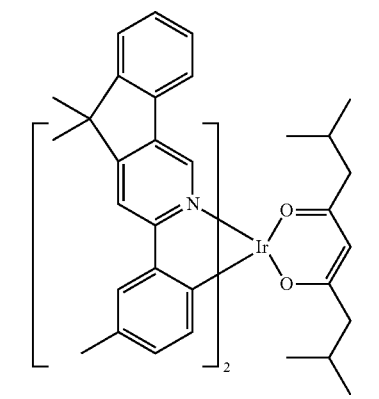
Compound 131
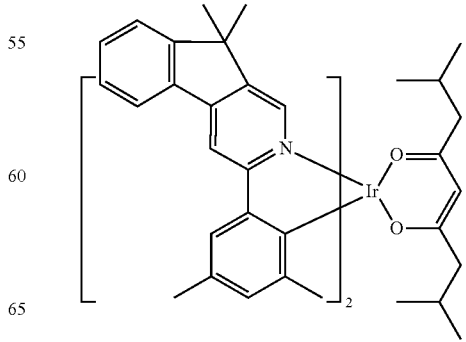
Compound 128
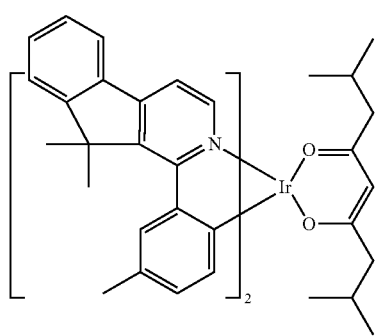
Compound 132

Compound 133
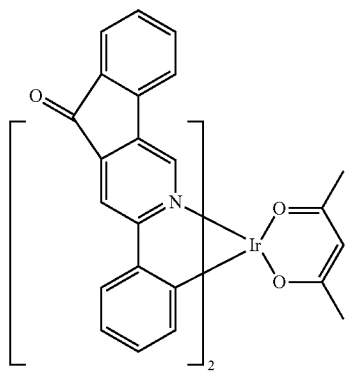
Compound 134
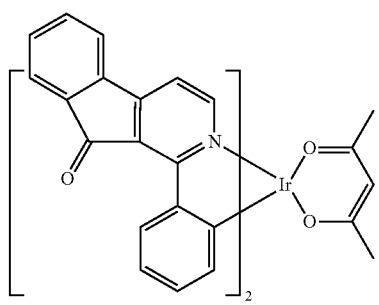
Compound 135
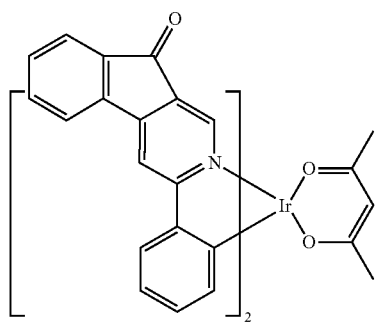
Compound 136
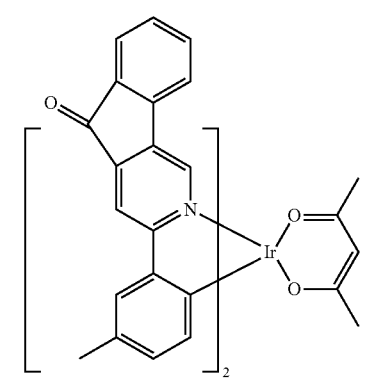
Compound 137
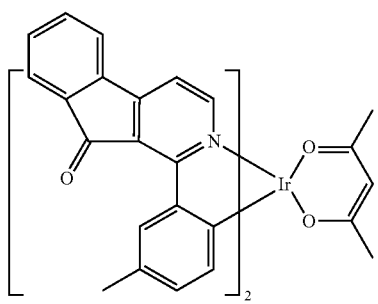
Compound 138
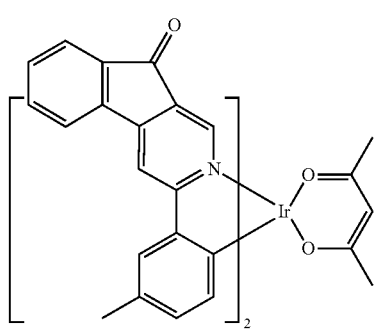
Compound 139
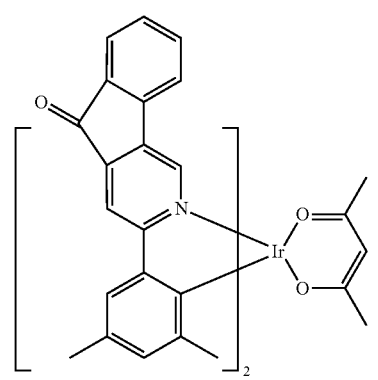
Compound 140
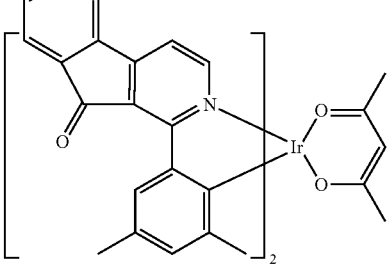
Compound 141
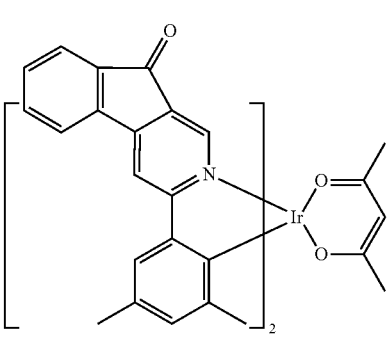

Compound 142
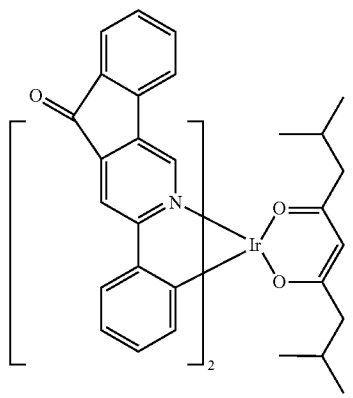
Compound 143
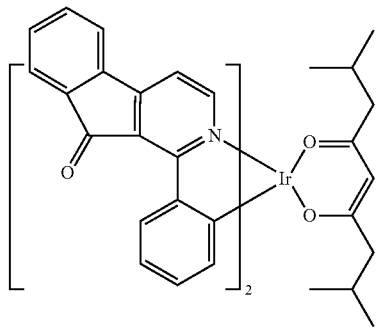
Compound 144
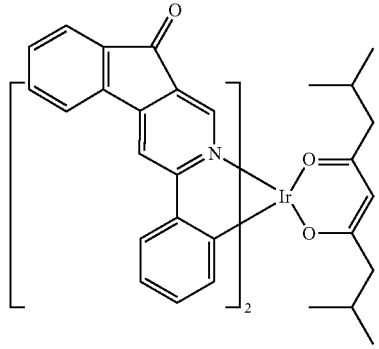
Compound 145
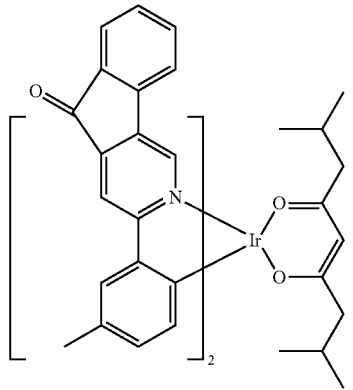
Compound 146
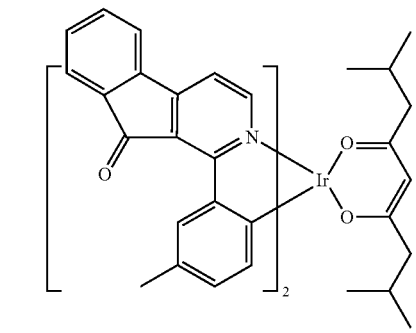
Compound 147
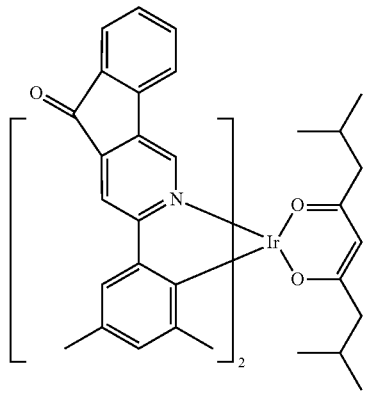
Compound 148
Compound 149
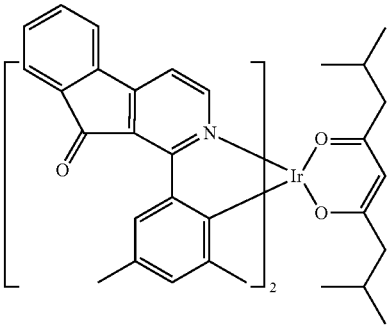

Compound 150

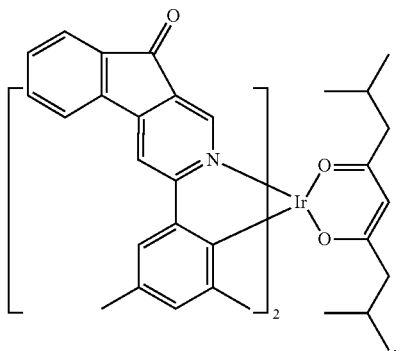

As discussed above, the chemical group used to substitute the aza DBX ligand may be used to tune the properties of the compound providing compounds and devices having improved characteristics. For example, the aza DBX ligands may be substituted with various heteroatoms. In one aspect, compounds are provided wherein X is O. Exemplary compounds wherein X is O include Compounds 1-12 and Compounds 61-78. Such compounds having an aza dibenzofuran ligand may have improved stability and improved efficiency. Devices containing compounds wherein X is O are especially preferred because they may provide improved stability and long lifetime.

In another aspect, compounds are provided wherein X is S. Exemplary compounds wherein X is S include Compounds 13-24 and Compounds 79-96. Such compounds having an aza dibenzothiophene ligand may have improved stability, increased efficiency, and long lifetime. Devices using the compounds wherein X is S are particularly preferred because they may provide the highly desirable combination of good efficiency and long lifetime.

In another aspect, compounds are provided wherein X is NR. Exemplary compounds wherein X is NR include Compounds 25-36 and Compounds 97-114. Such compounds having an aza carbazole ligand may have improved efficiency and stability.

The aza DBX ligands may also be substituted with carbon-containing chemical groups. In one aspect, compounds are provided wherein X is CRR'. Exemplary compounds wherein X is CRR' include Compounds 37-48 and Compounds 115-132. In another aspect, compounds are provided wherein X is C=O. Exemplary compounds wherein X is C=O include Compounds 49-60 and Compounds 133-150.

An organic light emitting device is also provided. The device comprises an anode, a cathode, and an organic emissive layer disposed between the anode and the cathode. The organic emissive layer includes a compound comprising a ligand having the structure FORMULA I, as discussed above. Selections for the heteroatoms and substituents described as preferred for compounds having FORMULA I are also preferred for use in a device that includes a compound having FORMULA I. These selections include those described for X, A, $R_1$, $R_2$, $R_3$, $R_4$, and $R_5$.

A is a 5-membered or 6-membered aromatic or heteroaromatic ring. In one aspect, preferably, A is benzene. In another aspect, preferably A is selected from the group consisting of furan, thiophene, and pyrrole.

$R_A$ is a substituent having the structure

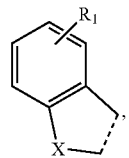

wherein the substituent is fused to the pyridine ring of FORMULA I. X is selected from the group consisting of CRR', C=O, BR, NR, O, S, and Se. R and R' are independently selected from hydrogen and alkyl. $R_1$, $R_2$, and $R_3$ may represent mono, di, tri, or tetra substitutions; each of $R_1$, $R_2$, and $R_3$ are independently selected from the group consisting of hydrogen, alkyl, alkoxy, amino, alkenyl, alkynyl, arylkyl, aryl, and heteroaryl. The ligand is coordinated to a metal having an atomic weight greater than 40. Preferably, the metal is Ir.

In one aspect, devices are provided wherein the compound comprises a ligand having the structure II. In another aspect, devices are provided wherein the compound comprises a ligand having the structure III. In yet another aspect, devices are provided wherein the compound comprises a ligand having the structure IV. In yet another aspect, devices are provided wherein the compound comprises a ligand having the structure V. In yet another aspect, devices are provided wherein the compound comprises a ligand having the structure VI. In a further another aspect, devices are provided wherein the compound comprises a ligand having the structure VII.

In one aspect, device are provided wherein the compound is selected from the group consisting of:

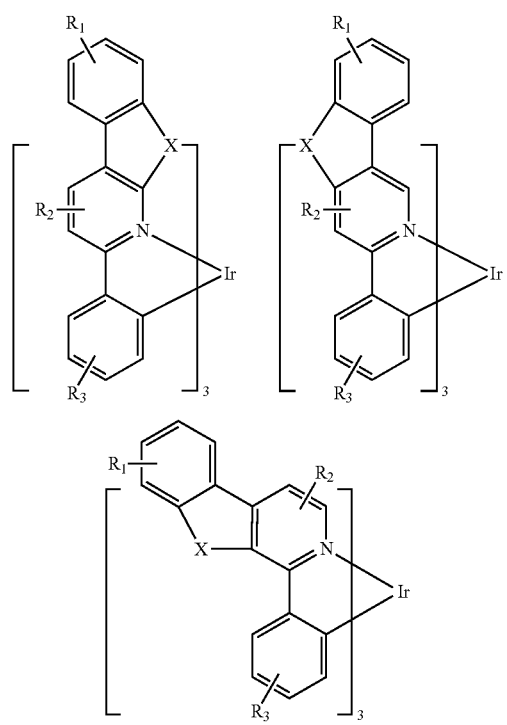

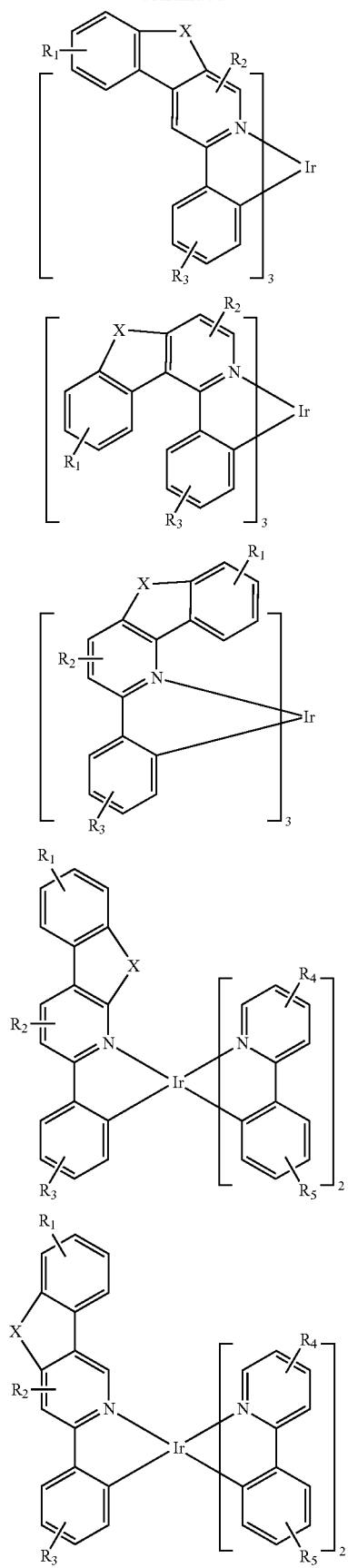
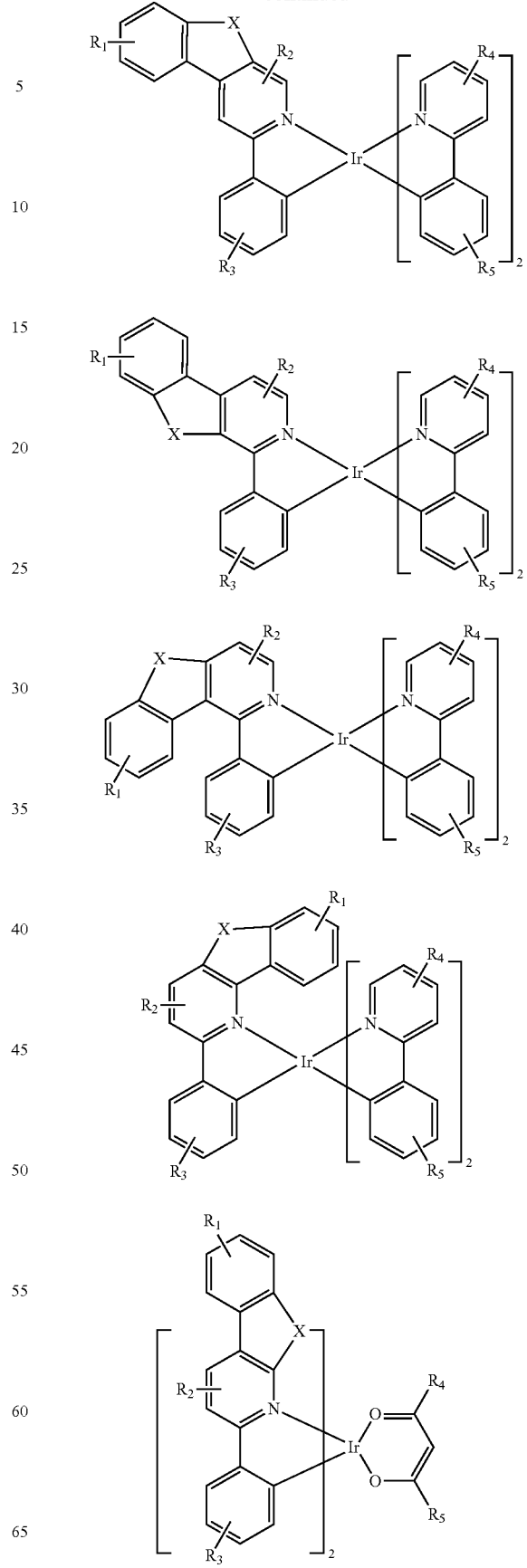

-continued

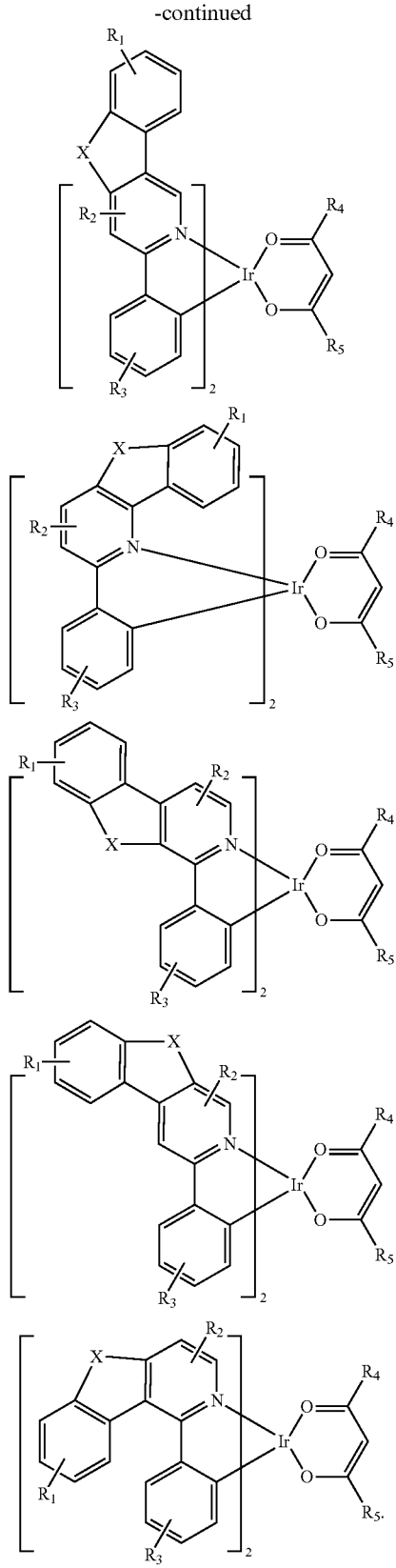

Particular devices are provided, the device comprising an organic layer containing a compound selected from the group consisting of Compounds 1-150, as shown above.

In one aspect, the organic emissive layer is an emissive layer and the compound is an emitting dopant. The organic layer may further comprise a host. Preferably, the host has the formula:

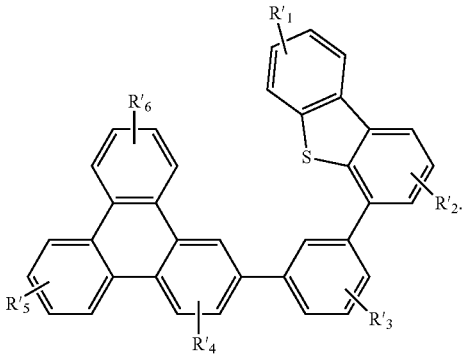

$R'_1$, $R'_2$, $R'_3$, $R'_4$, $R'_5$, and $R'_6$ may represent mono, di, tri, or tetra substitutions, and each of $R'_1$, $R'_2$, $R'_3$, $R'_4$, $R'_5$, and $R'_6$ are independently selected from the group consisting of hydrogen, alkyl, and aryl.

Additionally, a consumer product comprising a device is also provided. The device further comprises an anode, a cathode, and an organic layer disposed between the anode and the cathode. The organic layer further comprises a compound comprising a ligand having FORMULA I, as described above. Selections for the heteroatoms and substituents described as preferred for compounds having FORMULA I are also preferred for use in a device that includes a compound having FORMULA I. These selections include those described for X, A, $R_1$, $R_2$, $R_3$, $R_4$, and $R_5$.

A is a 5-membered or 6-membered aromatic or heteroaromatic ring.

$R_A$ is a substituent having the structure

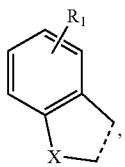

wherein the substituent is fused to the pyridine ring of FORMULA I. X is selected from the group consisting of CRR', C=O, BR, NR, O, S, and Se. R and R' are independently selected from hydrogen and alkyl. $R_1$, $R_2$, and $R_3$ may represent mono, di, tri, or tetra substitutions; each of $R_1$, $R_2$, and $R_3$ are independently selected from the group consisting of hydrogen, alkyl, alkoxy, amino, alkenyl, alkynyl, arylkyl, aryl, and heteroaryl. The ligand is coordinated to a metal having an atomic weight greater than 40.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| Hole injection materials | | |
| Phthalocyanine and prophryin compounds | 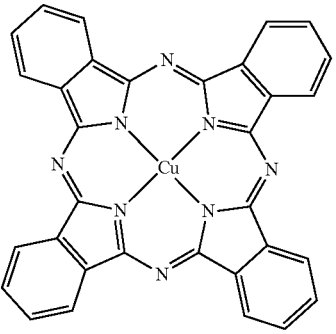 | Appl. Phys. Lett. 69, 2160 (1996) |
| Starburst triarylamines | 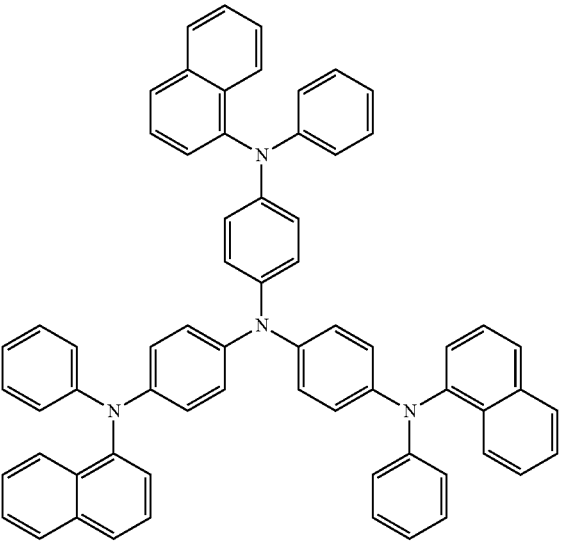 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-(CH_xF_y)_n-$ | Appl. Phys. Lett. 78, 673 (2001) |
| Conducting polymers (e.g., PEDOT:PSS, polyaniline, polypthiophene) | 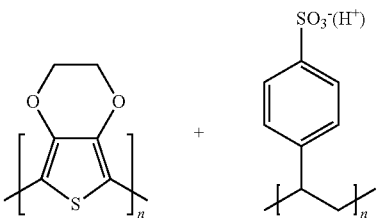 | Synth. Met. 87, 171 (1997) |

71
72
TABLE 1-continued
| MATERIAL | EXAMPLES OF MATERIAL | PUBLICATIONS |
|---|---|---|
| Arylamines complexed with metal oxides such as molybdenum and tungsten oxides | 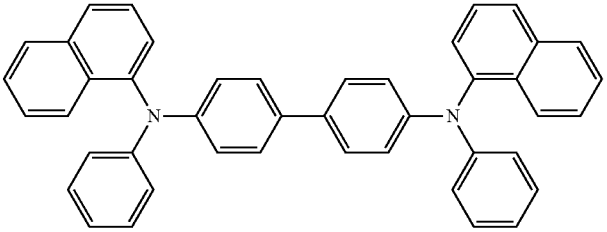 + MoO$_x$ | SID Symposium Digest, 37, 923, (2006) |
| Hole transporting materials | | |
| Triarylamines (e.g., TPD, α-NPD) | 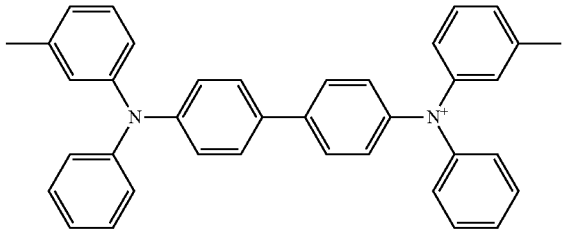 | Appl. Phys. Lett. 51, 913 (1987) |
| | 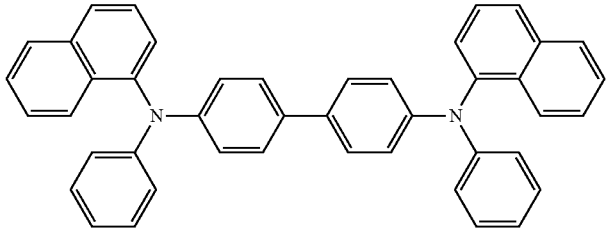 [SMILES: c1ccc(N(c2ccc(-c3ccc(N(c4ccccc4)c4cccc5ccccc45)cc3)cc2)c2cccc3ccccc23)cc1] | U.S. Pat. No. 5061569 |
| | 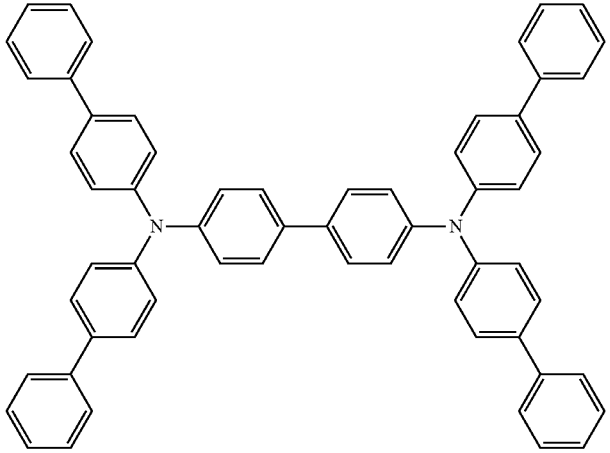 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |

TABLE 1-continued
| MATERIAL | EXAMPLES OF MATERIAL | PUBLICATIONS |
|---|---|---|
| | 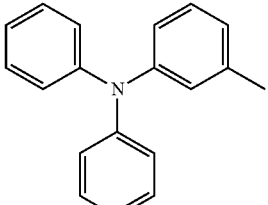 | J. Mater. Chem. 3, 319 (1993) |
| | 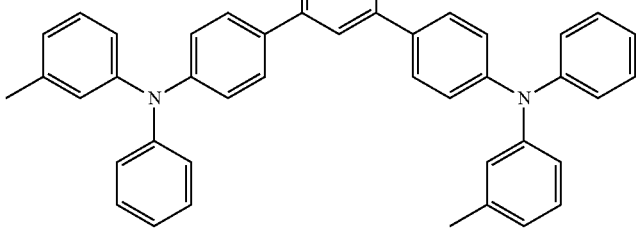 | Appl. Phys. Lett. 90, 183503 (2007) |
| | 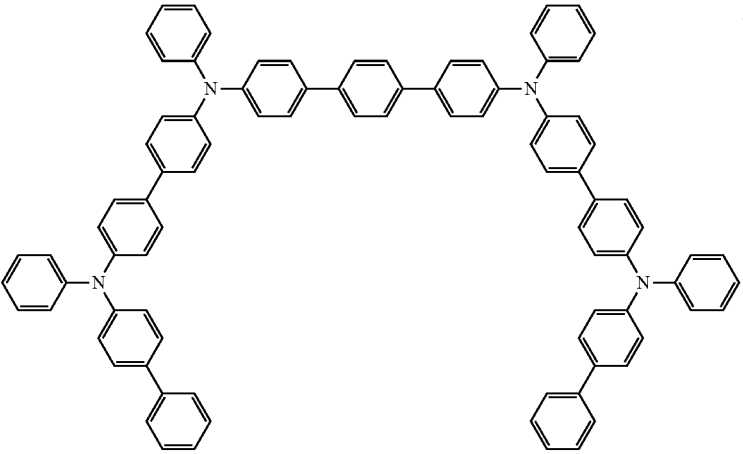 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE 1-continued

| MATERIAL | EXAMPLES OF MATERIAL | PUBLICATIONS |
| --- | --- | --- |
| Triaylamine on spirofluorene core | | Synth. Met. 91, 209 (1997) |
| Arylamine carbazole compounds | | Adv. Mater. 6, 677 (1994) |
| Indolocarbazoles | | Synth. Met. 111, 421 (2000) |
| Isoindole compounds | | Chem. Mater. 15, 3148 (2003) |

TABLE 1-continued

| MATERIAL | EXAMPLES OF MATERIAL | PUBLICATIONS |
| --- | --- | --- |
| Phosphorescent OLED host materials Red hosts | | |
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | U.S. Pat. No. 20060202194 |
| | | WO2005014551 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |

TABLE 1-continued
| MATERIAL | EXAMPLES OF MATERIAL | PUBLICATIONS |
|---|---|---|
| Green hosts | | |
| Arylcarbazoles | 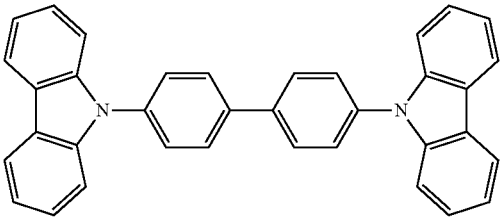 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 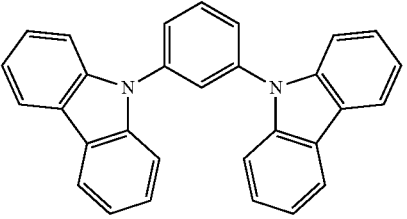 [SMILES: c1cc(-n2c3ccccc3c3ccccc32)cc(-n2c3ccccc3c3ccccc32)c1] | U.S. Pat. No. 2003175553 |
| | 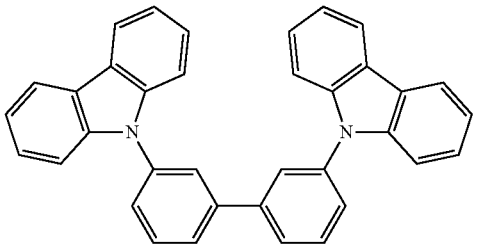 [SMILES: c1cc(-c2cccc(-n3c4ccccc4c4ccccc43)c2)cc(-n2c3ccccc3c3ccccc32)c1] | WO2001039234 |
| Aryltriphenylene compounds | 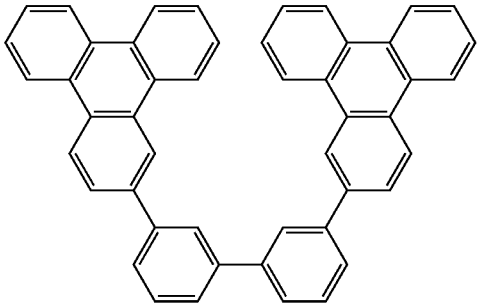 [SMILES: c1cc(-c2cccc(-c3ccc4c5ccccc5c5ccccc5c4c3)c2)cc(-c2ccc3c4ccccc4c4ccccc4c3c2)c1] | U.S. Pat. No. 20060280965 |
| | 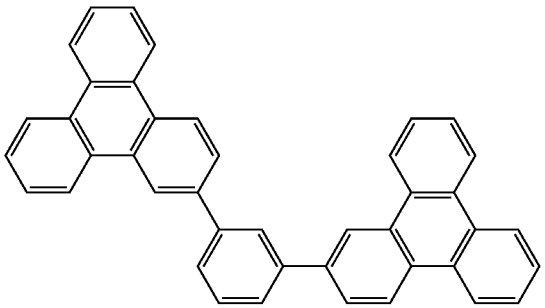 [SMILES: c1cc(-c2ccc3c4ccccc4c4ccccc4c3c2)cc(-c2ccc3c4ccccc4c4ccccc4c3c2)c1] | U.S. Pat. No. 20060280965 |
| Polymers (e.g., PVK) | 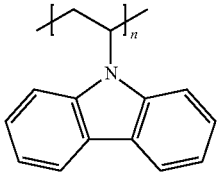 | Appl. Phys. Lett. 77, 2280 (2000) |

TABLE 1-continued

| MATERIAL | EXAMPLES OF MATERIAL | PUBLICATIONS |
|---|---|---|
| Spirofluorene compounds | | WO2004093207 |
| Metal phenoxybenzooxazole compounds | | WO05089025 |
| | | WO06132173 |
| | | JP200511610 |
| Spirofluorene-carbazole compounds | | JP2007254297 |

TABLE 1-continued
| MATERIAL | EXAMPLES OF MATERIAL | PUBLICATIONS |
|---|---|---|
| | 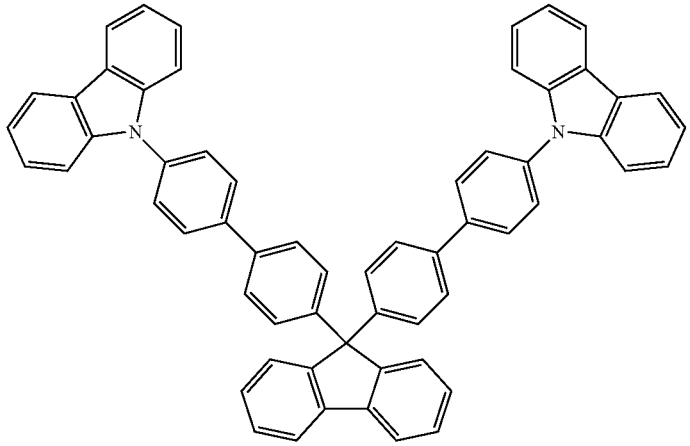 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocabazoles | 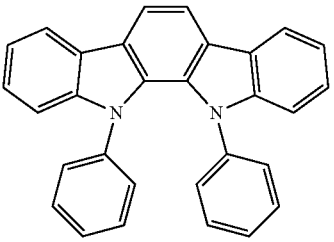 [SMILES: c1ccc(-n2c3ccccc3c3ccc4c5ccccc5n(-c5ccccc5)c4c32)cc1] | WO07063796 |
| | 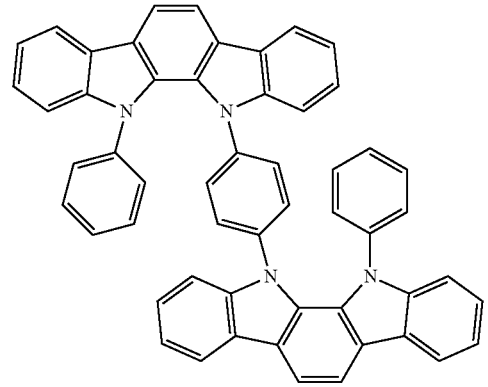 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO07063754 |
| 5-member ring electron deficient heterocycles (e.g., triazole, oxadiazole) | 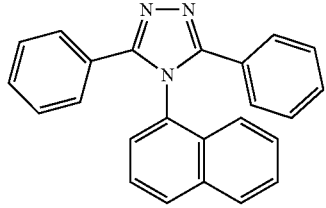 [SMILES: c1ccc(-c2nnc(-c3ccccc3)n2-c2cccc3ccccc23)cc1] | J. Appl. Phys. 90, 5048 (2001) |
| | 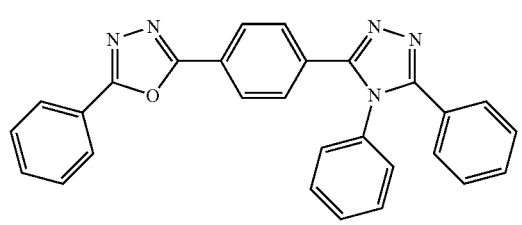 [SMILES: c1ccc(-c2nnc(-c3ccc(-c4nnc(-c5ccccc5)n4-c4ccccc4)cc3)o2)cc1] | WO04107822 |

TABLE 1-continued

| MATERIAL | EXAMPLES OF MATERIAL | PUBLICATIONS |
|---|---|---|
| Metal phenoxypyridine compounds | | WO05030900 |
| Blue hosts | | |
| Arylcarbazoles | | Appl. Phys. Lett, 82, 2422 (2003) |
| | | U.S. Pat. No. 20070190359 |
| Dibenzothiophene-carbazole compounds | | WO2006114966 |
| Phosphorescent dopants | | |
| Red dopants | | |
| Heavy metal porphyrins (e.g., PtOEP) | | Nature 395, 151 (1998) |

TABLE 1-continued

| MATERIAL | EXAMPLES OF MATERIAL | PUBLICATIONS |
|---|---|---|
| Iridium (III) organometallic complexes | | Appl. Phys. Lett. 78, 1622 (2001) |
| | | U.S. Pat. No. 06835469 |
| | | U.S. Pat. No. 06835469 |
| | | U.S. Pat. No. 20060202194 |
| | | U.S. Pat. No. 20060202194 |

| MATERIAL | EXAMPLES OF MATERIAL | PUBLICATIONS |
|---|---|---|
| | 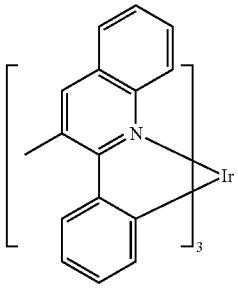 | U.S. Pat. No. 7087321 |
| | 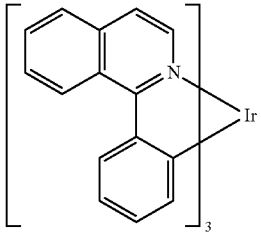 | U.S. Pat. No. 7087321 |
| | 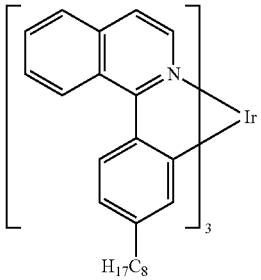 | Adv. Mater. 19, 739 (2007) |
| Platinum(II) organometallic complexes | 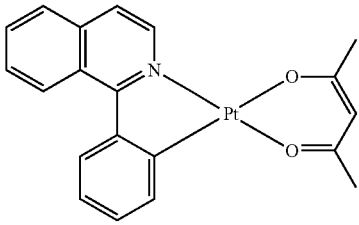 | WO2003040257 |
| Osminum(III) complexes | 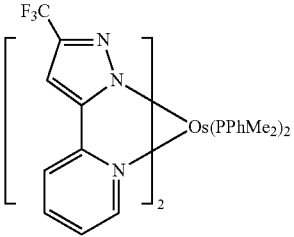 | Chem. Mater. 17, 3532 (2005) |
| Ruthenium(II) complexes | 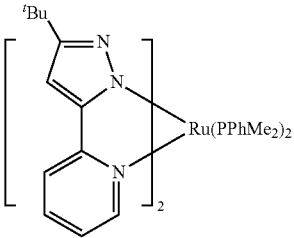 | Adv. Mater. 17, 1059 (2005) |

TABLE 1-continued
| MATERIAL | EXAMPLES OF MATERIAL | PUBLICATIONS |
| --- | --- | --- |
| Green dopants | | |
| Iridium(III) organometallic complexes | 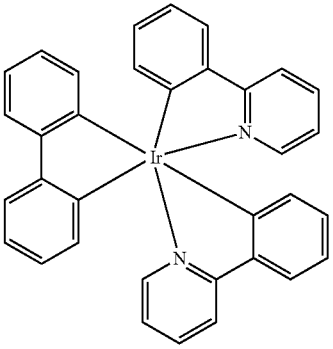<br>and its derivatives | Inorg. Chem. 40, 1704 (2001) |
| | 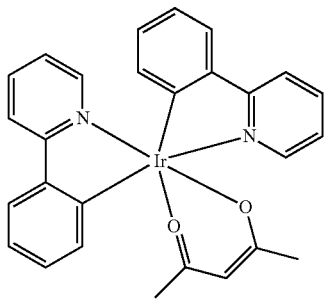 | U.S. Pat. No. 2002034656 |
| | 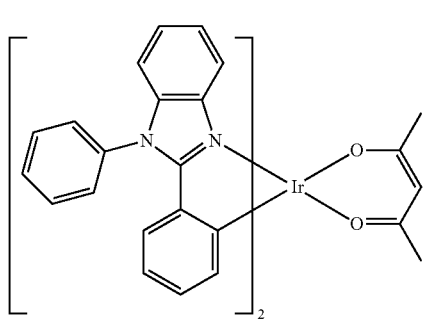 | U.S. Pat. No. 06687266 |
| | 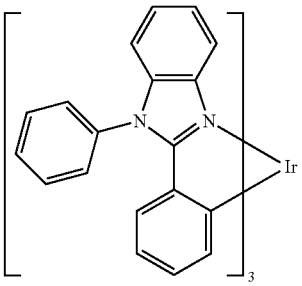 | Chem. Mater. 16, 2480 (2004) |

TABLE 1-continued

| MATERIAL | EXAMPLES OF MATERIAL | PUBLICATIONS |
|---|---|---|
| | | U.S. Pat. No. 2007190359 |
| | | U.S. Pat. No. 2006008670 JP2007123392 |
| | | Adv. Mater. 16, 2003 (2004) |
| | | Angew. Chem. Int. Ed. 2006, 45, 7800 |
| Pt(II) organometallic complexes | | Appl. Phys. Lett. 86, 153505 (2005) |

TABLE 1-continued
| MATERIAL | EXAMPLES OF MATERIAL | PUBLICATIONS |
|---|---|---|
| | 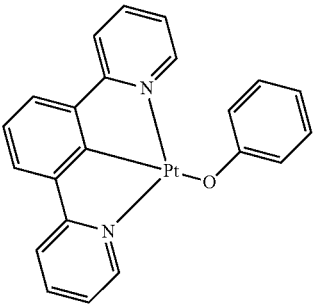 | Appl. Phys. Lett. 86, 153505 (2005) |
| | 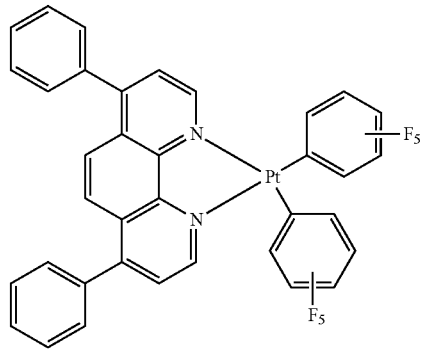 | Chem. Lett. 34, 592 (2005) |
| Gold complexes | 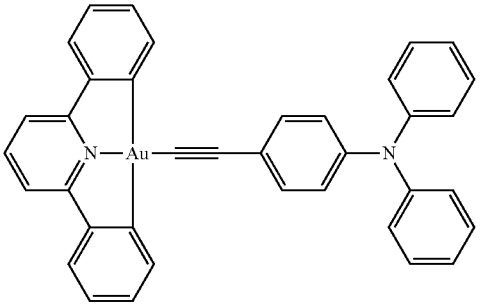 | Chem. Commun. 2906 (2005) |
| Rhenium(III) complexes | 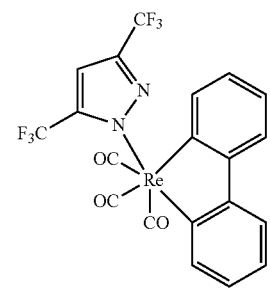 | Inorg. Chem. 42, 1248 (2003) |
| Blue dopants | | |
| Iridium(III) organometallic complexes | 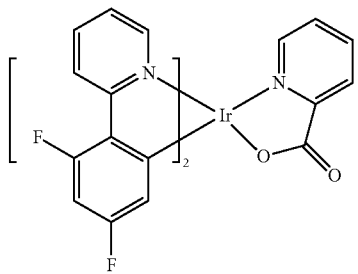 | WO2002002714 |

TABLE 1-continued
| MATERIAL | EXAMPLES OF MATERIAL | PUBLICATIONS |
|---|---|---|
| | 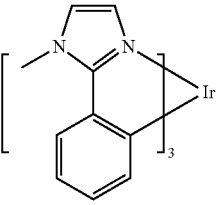 | WO2006009024 |
| | 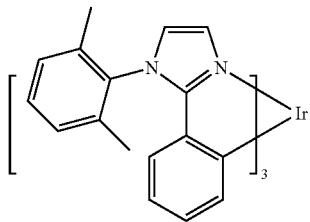 | U.S. Pat. No. 2006251923 |
| | 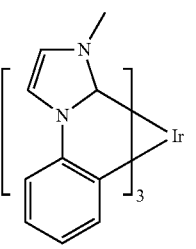 | WO2006056418, U.S. Pat. No. 2005260441 |
| | 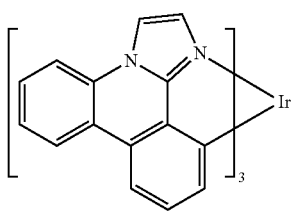 | U.S. Pat. No. 2007190359 |
| | 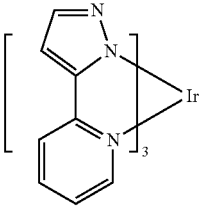 | U.S. Pat. No. 2002134984 |
| | 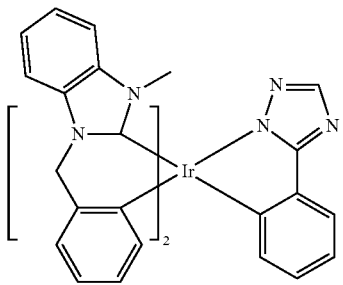 | Angew. Chem. Int. Ed. 47, 1 (2008) |

TABLE 1-continued

| MATERIAL | EXAMPLES OF MATERIAL | PUBLICATIONS |
|---|---|---|
| | | Chem. Mater. 18, 5119 (2006) |
| | | Inorg. Chem. 46, 4308 (2007) |
| | | WO05123873 |
| | | WO05123873 |
| | | WO07004380 |

TABLE 1-continued

| MATERIAL | EXAMPLES OF MATERIAL | PUBLICATIONS |
|---|---|---|
| | | WO06082742 |
| Osmium(II) complexes | | U.S. Pat. No. 2005260449 |
| | | Organometallics 23, 3745 (2004) |
| Gold complexes | | Appl. Phys. Lett. 74, 1361 (1999) |
| Plantinum(II) complexes | | WO06098120, WO06103874 |

TABLE 1-continued

| MATERIAL | EXAMPLES OF MATERIAL | PUBLICATIONS |
|---|---|---|
| Exciton/hole blocking layer materials | | |
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxyquinolates (e.g., BAlq) | | Appl. Phys. Lett. 81, 162 (2002) |
| 5-member ring electron deficient heterocycles such as triazole, oxadiazole, imidazole, benzoimidazole | | Appl. Phys. Lett. 81, 162 (2002) |

TABLE 1-continued
| MATERIAL | EXAMPLES OF MATERIAL | PUBLICATIONS |
|---|---|---|
| Triphenylene compounds | 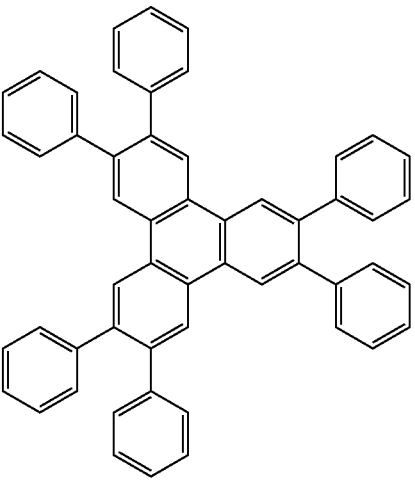 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | U.S. Pat. No. 20050025993 |
| Fluorinated aromatic compounds | 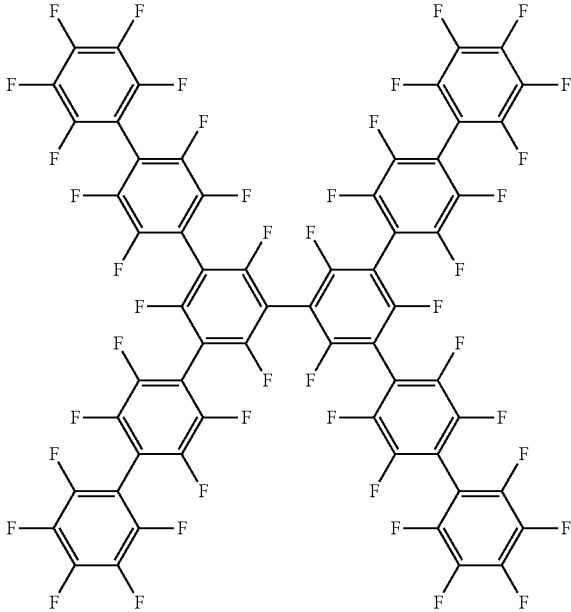 [SMILES: Fc1c(F)c(F)c(-c2c(F)c(F)c(-c3c(F)c(-c4c(F)c(F)c(-c5c(F)c(F)c(F)c(F)c5F)c(F)c4F)c(F)c(-c4c(F)c(-c5c(F)c(F)c(-c6c(F)c(F)c(F)c(F)c6F)c(F)c5F)c(F)c(-c5c(F)c(F)c(-c6c(F)c(F)c(F)c(F)c6F)c(F)c5F)c4F)c3F)c(F)c2F)c(F)c1F] | Appl. Phys. Lett. 79, 156 (2001) |

TABLE 1-continued

| MATERIAL | EXAMPLES OF MATERIAL | PUBLICATIONS |
| --- | --- | --- |
| Electron transporting materials | | |
| Anthracene-benzoimidazole compounds | | WO03060956 |
| Anthracene-benzothiazole compounds | | Appl. Phys. Lett. 89, 063504 (2006) |
| Metal 8-hydroxyquinolates (e.g., Alq$_3$) | | Appl. Phys. Lett. 51, 913 (1987) |
| Metal hydroxybenoquinolates | | Chem. Lett. 5, 905 (1993) |
| Bathocuprine compounds such as BCP, BPhen, etc | | Appl. Phys. Lett. 91, 263503 (2007) |

| MATERIAL | EXAMPLES OF MATERIAL | PUBLICATIONS |
|---|---|---|
| | 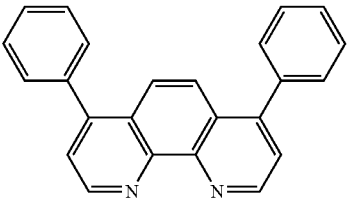 [SMILES: c1ccc(-c2ccnc3c2ccc2c(-c4ccccc4)ccnc23)cc1] | Appl. Phys. Lett. 79, 449 (2001) |
| 5-member ring electron deficient heterocycles (e.g., triazole, oxadiazole, imidazole, benzoimidazole) | 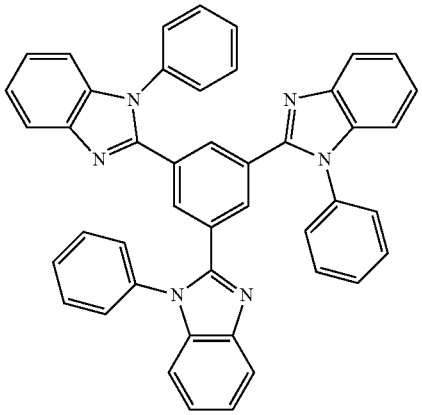 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 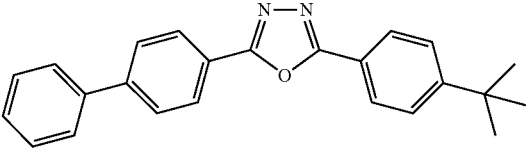 [SMILES: CC(C)(C)c1ccc(-c2nnc(-c3ccc(-c4ccccc4)cc3)o2)cc1] | Appl. Phys. Lett. 55, 1489 (1989) |
| | 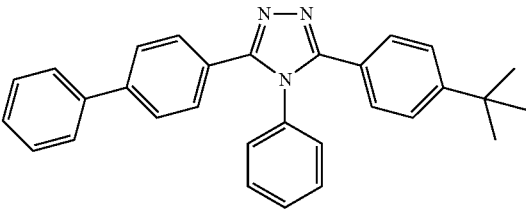 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 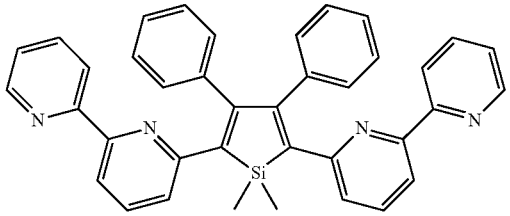 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 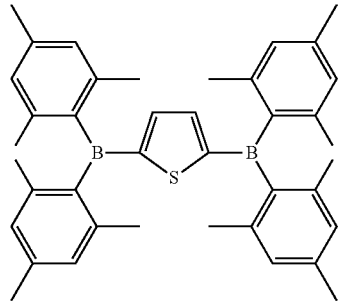 [SMILES: Cc1cc(C)c(B(c2ccc(B(c3c(C)cc(C)cc3C)c3c(C)cc(C)cc3C)s2)c2c(C)cc(C)cc2C)c(C)c1] | J. Am. Chem. Soc. 120, 9714 (1998) |

| MATERIAL | EXAMPLES OF MATERIAL | PUBLICATIONS |
|---|---|---|
| Fluorinated aromatic compounds | 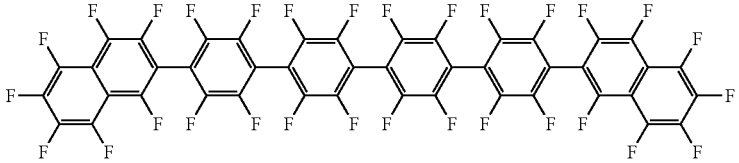 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

EXPERIMENTAL

Compound Examples

Example 1

Synthesis of Compound 1

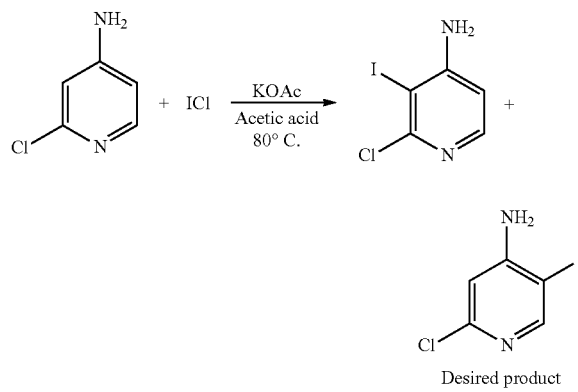

Desired product

Synthesis of 2-chloro-5-iodo-4-aminopyridine 2-chloro-4-aminopyridine (25 g, 194 mmol) and potassium acetate (19.05 g, 194 mmol) were dissolved in 250 mL acetic acid and heated to 80° C. A solution of (31.56 g, 194 mmol) in acetic acid (40 mL) was added dropwise and the reaction mixture was stirred at 80° C. for 3 h. The reaction mixture was cooled to room temperature and neutralized by saturated aq. NaHCO₃ solution. Dark off-white solid precipitated out, which was dissolved in methylene chloride and washed with saturated aq. NaHSO₃, dried over Na₂SO₄, concentrated and purified by column chromatography using hexanes and ethyl acetate as eluent. Isolated 11.6 g of title compound along with 13.4 g of undesired isomer.

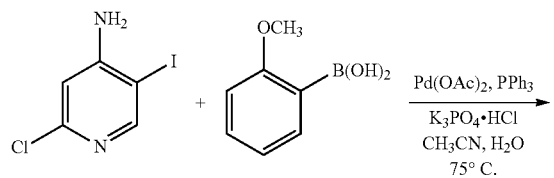

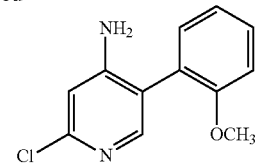

Synthesis of 2-chloro-5-(2-methoxyphenyl)pyridin-4-amine

Potassiumphosphate (18.28 g, 79 mmol), triphenyl phosphine (1.04 g, 3.97 mmol), 2-chloro-5-iodo-4-aminopyridine (10.1 g, 39. mmol), 2-methoxybenzeneboronic acid (8.44 g, 55.57 mmol) and palladium acetate (0.45 g, 1.98 mmol) were sequentially added to degassed acetonitrile (300 mL) and water (100 mL) under nitrogen. The reaction mixture was heated at 75° C. for overnight, then cooled to room temperature. The organic layer was separated and aqueous layer and was extracted with ethyl acetate. The combined organic layers were dried over sodium sulfate, concentrated and performed column chromatography using hexanes and ethyl acetate as eluent. 7.5 g of title compound was isolated.

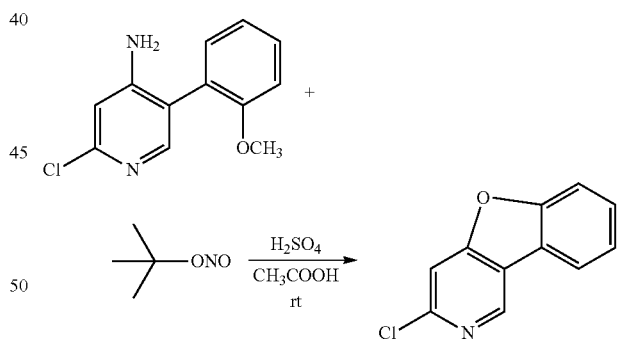

Synthesis of 3-chlorobenzofuro[3,2-c]pyridine 2-chloro-5-(2-methoxyphenyl)pyridin-4-amine (7.5 g, 31.96 mmol) was dissolved in glacial acetic acid (200 mL) and concentrated sulfuric acid (1 mL). A solution of t-butylnitrite (11.39 mL, 95.87 mmol) in 10 mL of acetic acid was added drop wise and stirred for 30 minutes. The reaction mixture was concentrated under reduced pressure, dissolved in methylene chloride. The reaction mixture was dried over sodium sulfate, concentrated and the residue was purified by silica column using hexanes and ethyl acetate as eluent to give 5.0 g of title compound.

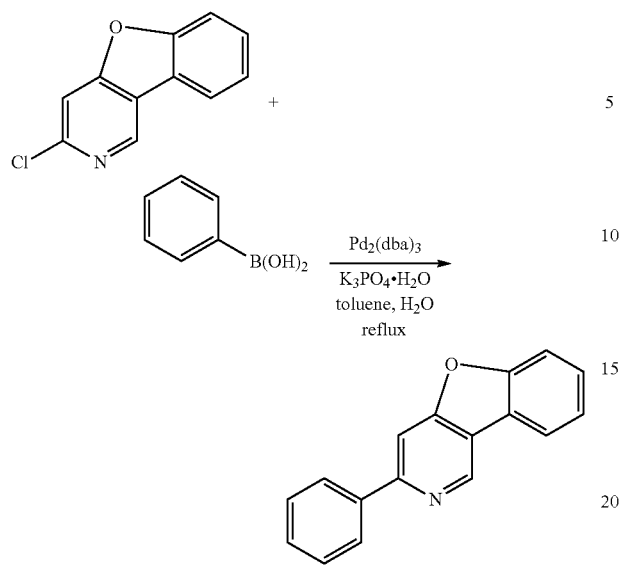

Synthesis of 3-phenylbenzofuro[3,2-c]pyridine 3-chlorobenzofuro[3,2-c]pyridine (2.89 g, 14 mmol), phenylboronic acid (2.56 g, 21 mmol), potassium phosphate (9.6 g, 42 mmol), 2-dicyclohexylphosphino-2',6'-dimethoxybiphenyl (0.45 g, 1.12 mmol) and Pd$_2$(bda)$_3$ (0.256 g, 0.28 mmol) were to toluene (100 mL) and water (10 mL). Nitrogen was bubbled through the solution for 30 minutes and then the solution was refluxed for overnight in an atmosphere of nitrogen. The reaction was then allowed to cool to room temperature and the organic phase was separated from the aqueous phase. The aqueous phase was washed with ethyl acetate and the organic fractions were combined and dried over sodium sulfate and the solvent removed under vacuum. The product was chromatographed using silica gel with ethyl acetate and hexanes as the eluent. The solvent was removed to give 2.77 g of title compound.

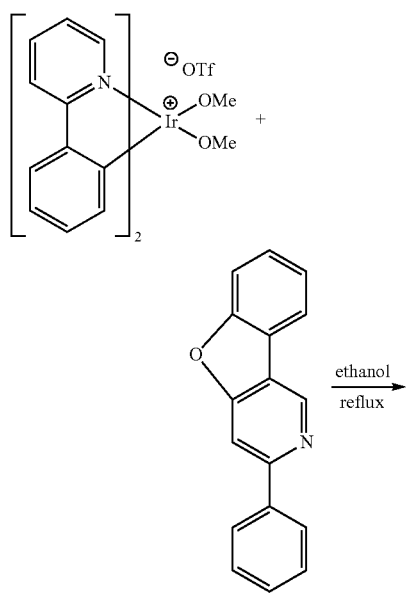

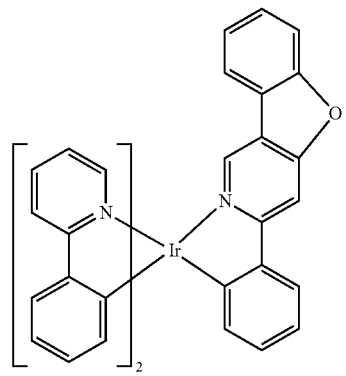

Synthesis of Compound 1:

Iridium intermediate (2.67 g, 3.76 mmol) and 3-phenylbenzofuro[3,2-c]pyridine (2.77 g, 11.29 mmol) was mixed in 50 mL of anhydrous ethanol. The mixture was heated to reflux under nitrogen for 24 h. The reaction mixture was cooled to room temperature; the precipitate was collected by filtration. The crude precipitate (1.9 g) was purified by silica column using 2:3 dichloromethane and hexanes to 0.9 g of desired product was obtained after column purification. The compound was further purified by high vacuum sublimation at 290° C. to yield 0.55 g of product (HPLC purity 99.7%).

Example 2

Synthesis of Compound 7

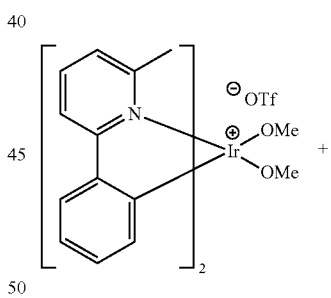

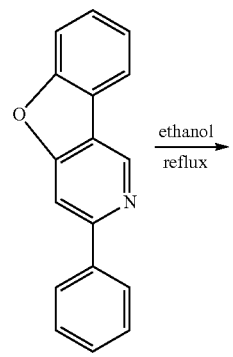

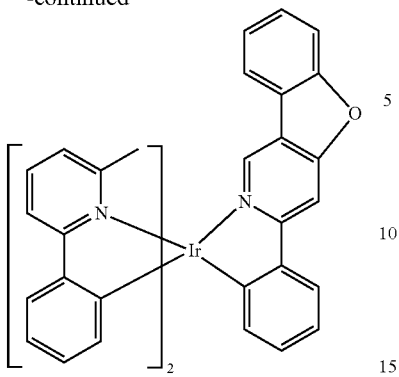

Synthesis of Compound 7:

Iridium intermediate (1.82 g, 2.46 mmol) and 3-phenyl-benzofuro[3,2-c]pyridine (1.81 g, 7.38 mmol) was mixed in 40 mL of anhydrous ethanol. The mixture was heated to reflux under nitrogen for 24 h. The reaction mixture was cooled to room temperature; the precipitate was collected by filtration. The crude precipitate (1.8 g) was purified by short silica column using hot dichloromethane. The compound was further purified by high vacuum sublimation at 290° C. to yield 0.64 g of product (HPLC purity 99%).

Example 3

Synthesis of Compound 8

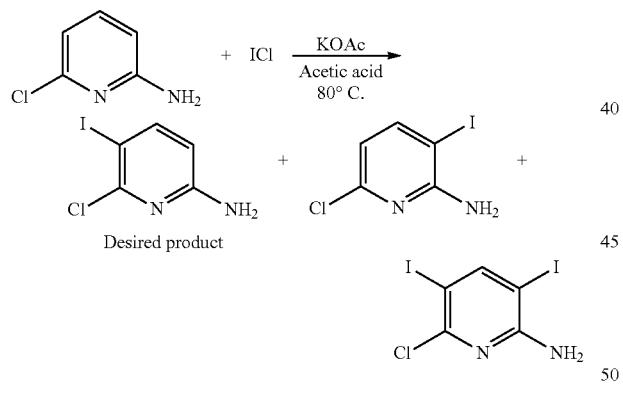

Synthesis of 6-chloro-5-iodo-2-aminopyridine 2-chloro-6-aminopyridine (23.0 g, 178 mmol) and potassium acetate (17.5 g, 178 mmol) were dissolved in 200 mL acetic acid and heated to 80° C. A solution of ICl (29.05 g, 178 mmol) in acetic acid (40 mL) was added dropwise and the reaction mixture was stirred at 80° C. for 4 h. The reaction mixture was cooled to room temperature and the acetic acid was removed under reduced pressure. The residue was dissolved in ethyl acetate and neutralized by saturated aq. NaHCO$_3$ solution. The organic layer was washed with saturated aq. NaHSO$_3$, dried over Na$_2$SO$_4$, concentrated and purified by silica column using hexanes and ethyl acetate as eluent. Isolated 6.1 g of title compound.

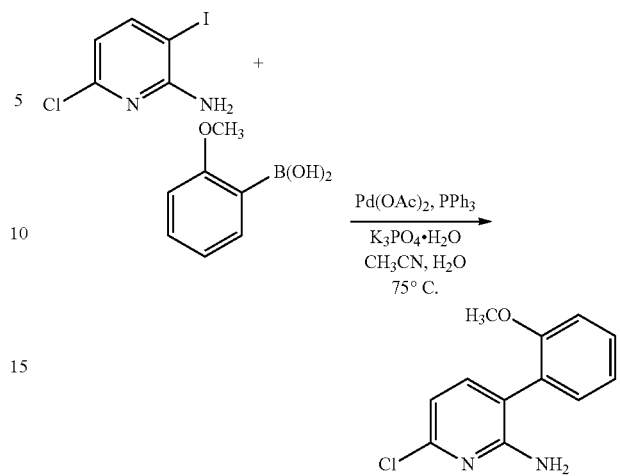

Synthesis of 6-chloro-3-(2-methoxyphenyl)pyridin-2-amine

Potassium phosphate (12.72 g, 60 mmol), triphenyl phosphine (0.682 g, 2.40 mmol), 6-chloro-5-iodo-2-aminopyridine (6.1 g, 24 mmol), 2-methoxybenzeneboronic acid (5.10 g, 33.5 mmol) and palladium acetate (0.27 g, 1.20 mmol) were sequentially added to degassed acetonitrile (200 mL) and water (60 mL) under nitrogen. The reaction mixture was heated at 75° C. for overnight, then cooled to room temperature. The organic layer was separated and aqueous layer and was extracted with ethyl acetate. The combined organic layers were dried over sodium sulfate, concentrated and purified by silica column using hexanes and ethyl acetate as eluent furnishing 4.05 g of title compound.

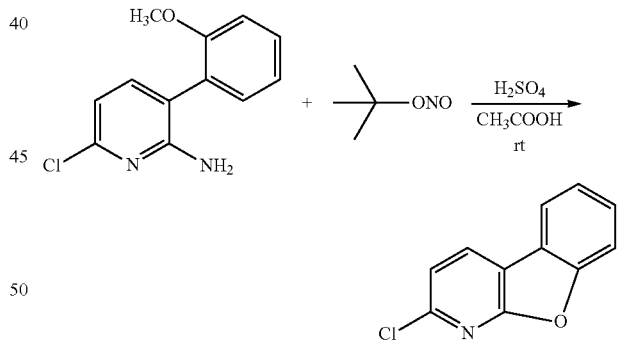

Synthesis of 2-chlorobenzofuro[2,3-b]pyridine 6-chloro-3-(2-methoxyphenyl)pyridin-2-amine (4.0 g, 17.04 mmol) was dissolved in glacial acetic acid (100 mL) and concentrated sulfuric acid (1 mL). A solution of t-butylnitrite (6.1 mL, 51.2 mmol) in 6 mL of acetic acid was added drop wise and stirred for 30 minutes. The reaction mixture was concentrated under reduced pressure, dissolved in methylene chloride. The reaction mixture neutralized by saturated aq. NaHCO$_3$ solution and the organic phase was separated from the aqueous phase. The aqueous phase extracted with methylene chloride and the combined organic layers was dried over sodium sulfate, concentrated and the residue was purified by silica column using hexanes and ethyl acetate as eluent to give 1.85 g of title compound.

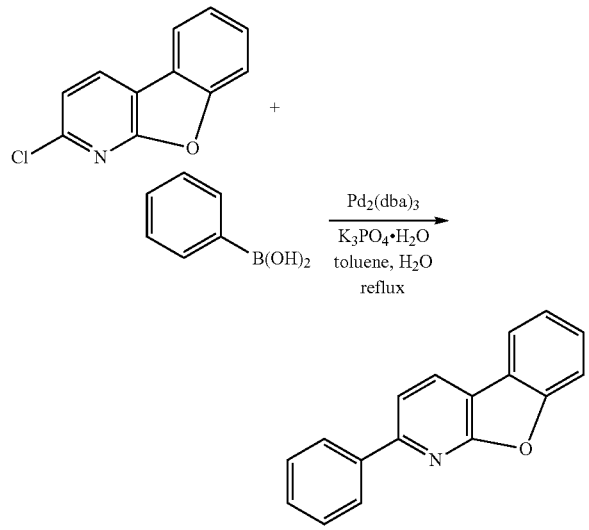

Synthesis of 2-phenylbenzofuro[2,3-b]pyridine 2-chlorobenzofuro[2,3-b]pyridine (1.33 g, 6.53 mmol), phenylboronic acid (1.19 g, 9.80 mmol), potassium phosphate (4.51 g, 19.59 mmol), 2-dicyclohexylphosphino-2',6'-dimethoxybiphenyl (0.214 g, 0.522 mmol) and $Pd_2(bda)_3$ (0.119 g, 0.13 mmol) were to toluene (40 mL) and water (4 mL). Nitrogen was bubbled through the solution for 30 minutes and then the solution was refluxed for overnight in an atmosphere of nitrogen. The reaction was then allowed to cool to room temperature and the organic phase was separated from the aqueous phase. The aqueous phase was extracted with ethylacetate and the organic fractions were combined and dried over sodium sulfate and the solvent removed under vacuum. The product was chromatographed using silica gel with ethylacetate and hexanes as the eluent. The solvent was removed to give 1.45 g of title compound.

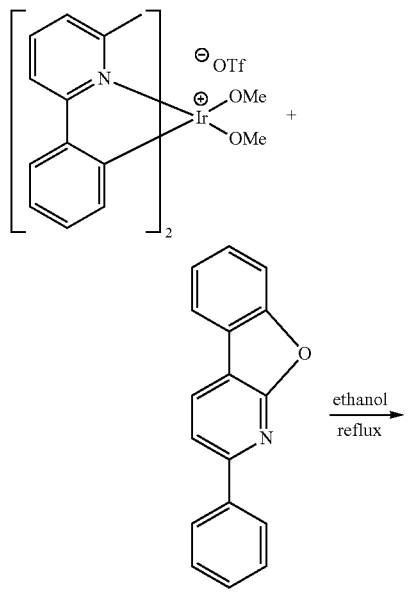

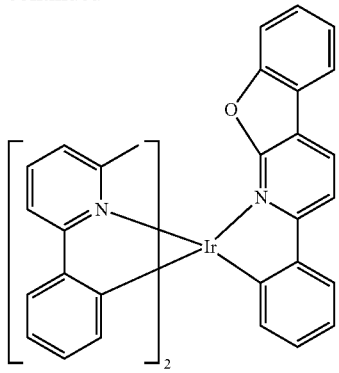

Synthesis of Compound 8:

Iridium intermediate (1.15 g, 1.55 mmol) and 2-phenylbenzofuro[2,3-b]pyridine (1.14 g, 4.66 mmol) was mixed in 30 mL of anhydrous ethanol. The mixture was heated to reflux under nitrogen for 24. The reaction mixture was cooled to room temperature; the precipitate was collected by filtration. The crude precipitate (1.0 g) was purified by silica column using dichloromethane and hexanes as eluent. The compound was further purified by high vacuum sublimation at 290° C. to yield 0.3 g of product (HPLC purity 99%).

Example 4

Synthesis of Compound 22

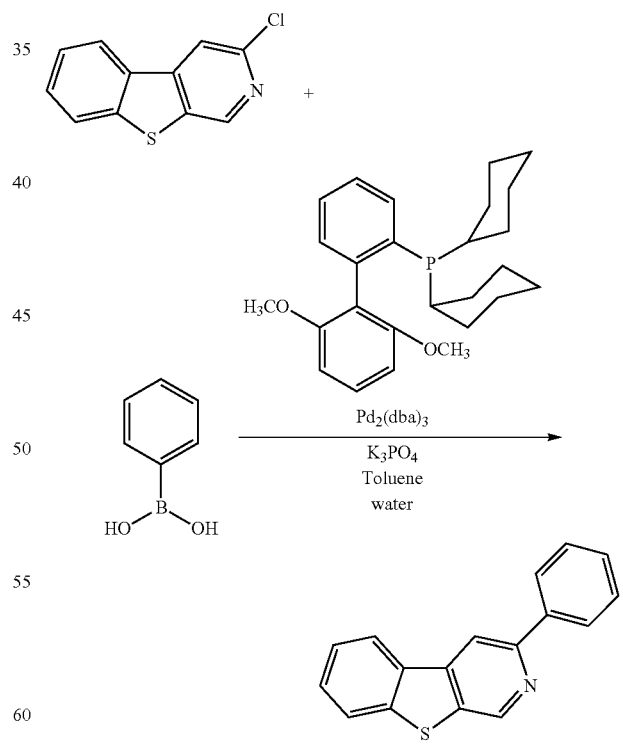

Synthesis of 2-phenyl-3-azadibenzothiophene 2-chloro-3-azadibenzothiophene (1.3 g, 5.7 mmol), phenylboronic acid (0.87 g, 7.1 mmol), dicyclohexyl(2',6'- dimethoxybiphenyl-2-yl)phosphine (S-Phos) (0.09 g, 0.23 mmol), and potassium phosphate (3.3 g, 14.3 mmol) were mixed in 60 mL of toluene and 6 mL of water. Nitrogen is bubbled directly into the mixture for 30 minutes. Next, Pd$_2$(dba)$_3$ was added (0.05 g, 0.05 mmol) and the mixture was heated to reflux under nitrogen for 3 days. The mixture was cooled and the organic layer was separated. The organic layers are washed with brine, dried over magnesium sulfate, filtered, and evaporated to a residue. The residue was purified by column chromatography eluting with 5% ethyl acetate/hexanes. 0.4 g of desired product was obtained after purification.

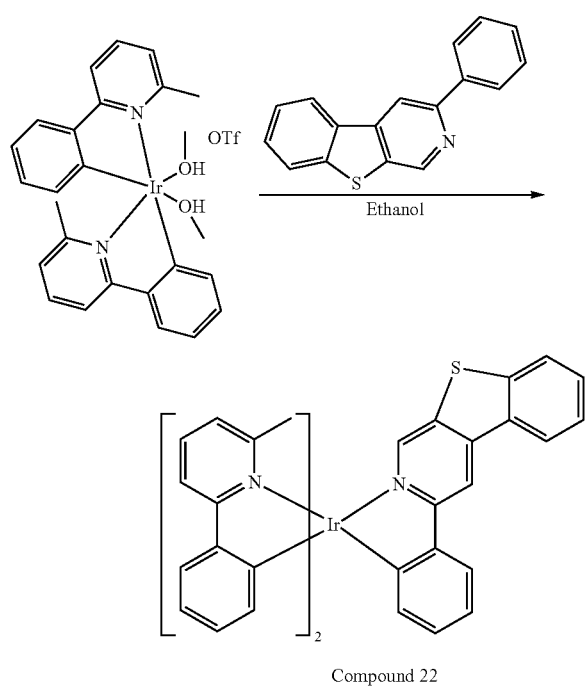

Compound 22

Synthesis of Compound 22:

The iridium triflate precursor (0.4 g, 1.5 mmol) and 2-phenyl-3-azadibenzothiophene (0.4 g, 0.5 mmol) were mixed in 20 mL of ethanol. The mixture was heated at reflux for 24 h under nitrogen. Precipitate formed during reflux. The reaction mixture was filtered through a celite bed. The product was washed with methanol and hexanes. The solid was dissolved in dichloromethane and purified by column using 1:1 of dichloromethane and hexanes. 0.34 g of pure product was obtained after the column purification. (HPLC purity: 99.3%)

Example 5

Synthesis of Compound 31

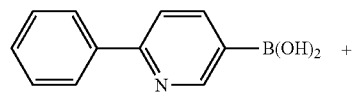

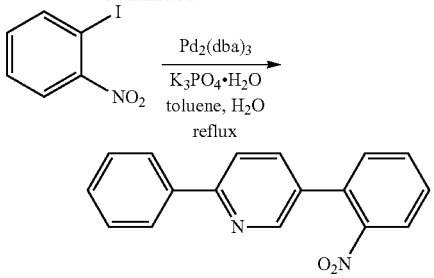

Synthesis of 5-(2-nitrophenyl)-2-phenylpyridine

2-Iodo-1-nitrobenzene (6.88 g, 27.64 mmol), 6-phenyl-3-pyridinylboronic acid (5.5 g, 27.64 mmol), potassium phosphate (17.6 g, 82.91 mmol), 2-dicyclohexylphosphino-2',6'-dimethoxybiphenyl (0.451 g, 0.522 mmol) and Pd$_2$(bda)$_3$ (0.119 g, 0.55 mmol) were to toluene (150 mL) and water (12 mL). Nitrogen was bubbled through the solution for 30 minutes and then the solution was refluxed for overnight in an atmosphere of nitrogen. The reaction was then allowed to cool to room temperature and the organic phase was separated from the aqueous phase. The aqueous phase was extracted with ethylacetate and the organic fractions were combined and dried over sodium sulfate and the solvent removed under vacuum. The product was chromatographed using silica gel with ethylacetate and hexanes as the eluent. The solvent was removed to give 5.02 g of the title compound.

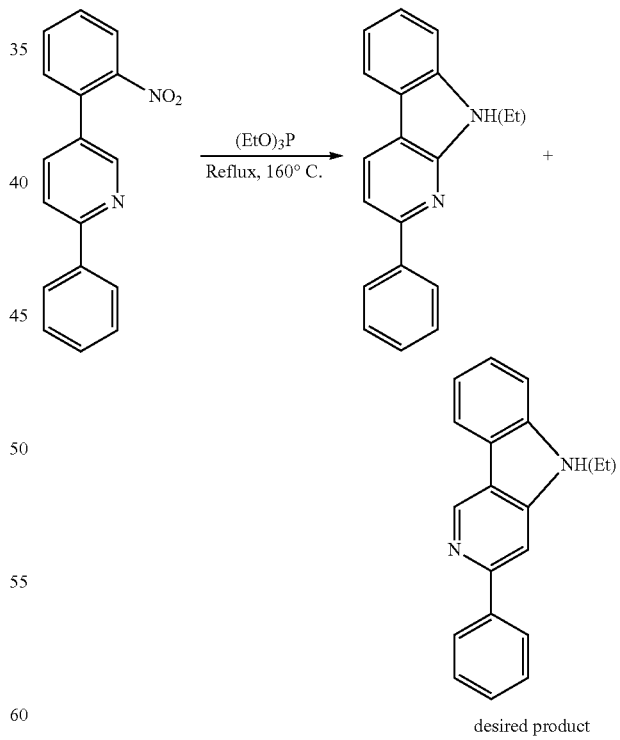

desired product

Synthesis of aza-carbozole:
5-(2-nitrophenyl)-2-phenylpyridine (5.0 g, 18.10 mmol) and triethyl phosphite (30 g, 180.97 mmol) were heated at 160° C. under nitrogen atmosphere for overnight. After the time, the reaction mixture is cooled to room temp. and aq. 6N HCl (60 mL) was added. The acidic solution was neutralized with NaOH pellets till the pH is 12. The reaction mixture was extracted with ethylacetate and the combined organic fractions were dried over sodium sulfate and the solvent was removed under reduced vacuum. The product was chromatographed using silica gel with ethylacetate and hexanes as the eluent. The solvent was removed to give 3.0 g of the carbozole products.

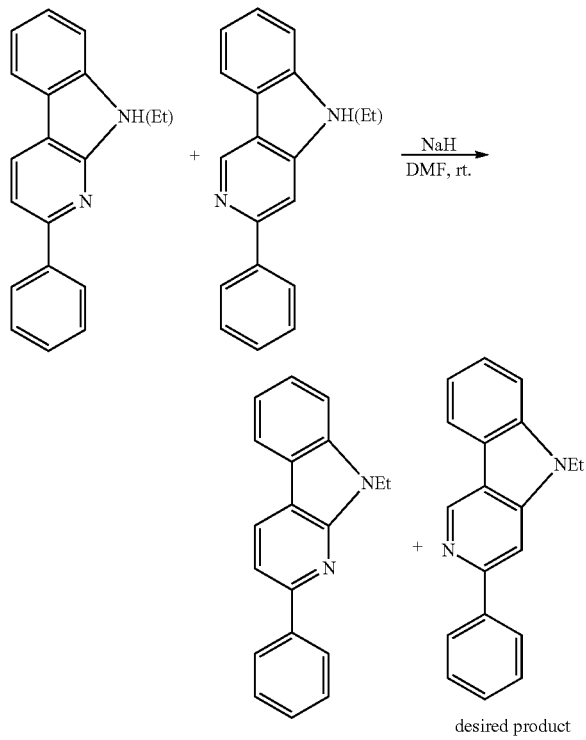

Synthesis of 5-ethyl-3-phenyl-5H-pyrido[4,3-b]indole

To a flask containing carbozoles (1.90 g, 7.78 mmol) and sodium hydride (0.55 g, 23.33 mmol), dry DMF (50 mL) was added and the reaction was stirred for 30 minutes at room temperature. After the time, ethyl iodide was added and the reaction was stirred for overnight. TLC showed the reaction was complete, and the reaction was quenched with saturated aq. NaCl solution. The mixture was extracted with ethyl acetate and the combined organic fractions were washed with NaCl solution, LiCl solution and dried over sodium sulfate and the solvent removed under vacuum. The product was chromatographed using silica gel with ethylacetate and hexanes as the eluent. The solvent was removed to give 502 mg of the desired title compound.

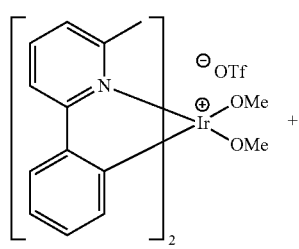

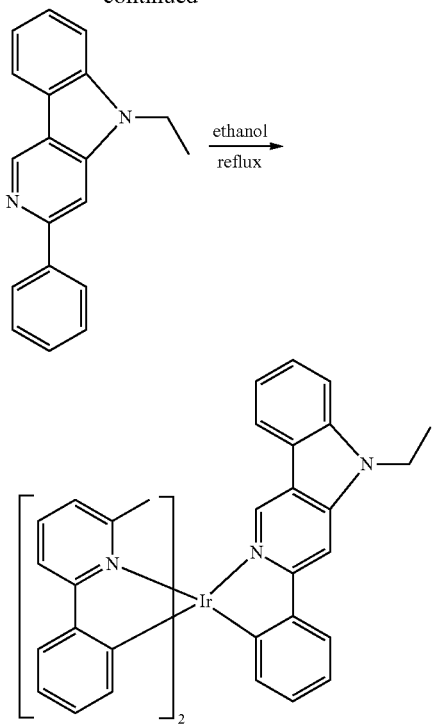

Synthesis of Compound 31:

Iridium intermediate (0.416 g, 0.563 mmol) and 5-ethyl-3-phenyl-5H-pyrido[4,3-b]indole (0.46 g, 1.69 mmol) was mixed in 10 mL of anhydrous ethanol. The mixture was heated to reflux under nitrogen for 24 h. The reaction mixture was cooled to room temperature, and the precipitate was collected by filtration. The crude precipitate was purified by silica column using dichloromethane and hexanes as eluent to yield 0.35 g of the complex.

Example 6

Synthesis of Compound 86

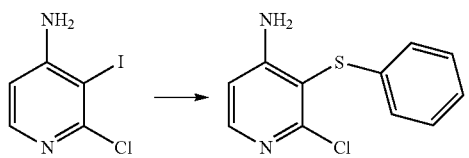 [SMILES: Nc1ccnc(Cl)c1I ; Nc1ccnc(Cl)c1Sc1ccccc1]

Synthesis of 2-chloro-3-(phenylthio)pyridin-4-amine

Into a 250 mL round bottom flask was placed the 2-chloro-3-iodo-4-aminopyridine (3.0 g, 11.8 mmol), thiophenol (1.3 g, 11.8 mmol), copper(I) iodide (0.11 g, 0.58 mmol), ethylene glycol (1.5 g, 24 mmol) and potassium carbonate (3.3 g, 24 mol). 100 mL of 2-propanol was then added to the reaction mixture and the mixture was heated at reflux for 18 h. The reaction mixture was cooled to room temperature and was filtered under vacuum. The filtrate was diluted with 200 mL of water then was extracted two times with 150 mL of ethyl acetate. The extracts were dried over magnesium sulfate then were filtered and stripped under vacuum. The product was purified using Silica gel chromatography with 2-15% ethyl acetate/dichloromethane as the mobile phase. 2.0 g (72% yield of product was collected.

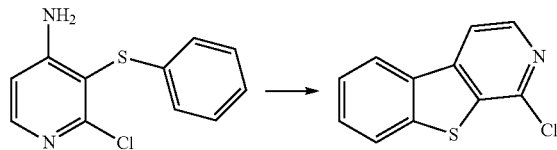 [SMILES: Nc1ccnc(Cl)c1Sc1ccccc1 ; Clc1nccc2c1sc1ccccc12]

Synthesis of 3-aza-4-chlorodibenzothiophene

Into a 250 mL three neck flask was placed the aminopyridine (2.0 g, 8.5 mmol). This material was dissolved in 30 mL of glacial acetic acid and was stirred at room temperature. To this mixture tert-butyl nitrite (0.87 g, 8.5 mol) was added dropwise over a 15 minute period. This mixture was then stirred for 1 h at room temperature. Next, additional tert-butyl nitrite (0.44 g, 0.0043 mol) was added to the reaction mixture and this was stirred at room temperature for an additional 2 h. The reaction mixture was poured onto ice and was basified using sodium bicarbonate. The mixture was then extracted with ethyl acetate and the extracts were dried over magnesium sulfate. The extracts were then filtered and stripped under vacuum. The product was purified using Silica gel chromatography with 10-20% ethyl acetate/hexanes as the mobile phase. 1.55 g (83% yield) of product was collected.

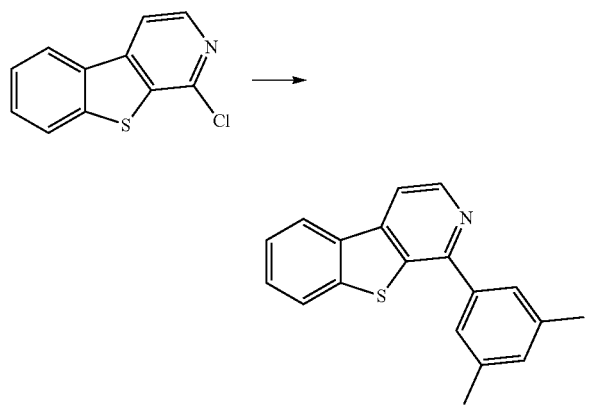

Synthesis of 4-(3',5'-dimethylphenyl)-3-azadibenzothiophene

Into a 250 mL round bottom flask was placed the chloroazabenzothiophene (1.55 g, 7.1 mmol), 3,5-Dimethylphenyl boronic acid (1.70 g, 11 mmol)., potassium phosphate tribasic monohydrate (7.6 g, 33 mol), $Pd_2(dba)_3$ (0.065 g, 0.071 mol) and 2-Dicyclohexylphosphino-2',6'-dimethoxylbiphenyl (0.12 g, 0.28 mol). To this mixture was added 200 mL of toluene and 30 mL of water. This mixture was evacuated and back-filled with nitrogen. This procedure was repeated a total of 3 times. The reaction mixture was stirred and heated at reflux for 18 h. The toluene layer was separated and was dried over magnesium sulfate. The organics were then filtered and stripped under vacuum. The product was purified using Silica gel chromatography with 10-20% ethyl acetate/hexanes as the mobile phase. 2.0 g (97% yield) of product was collected.

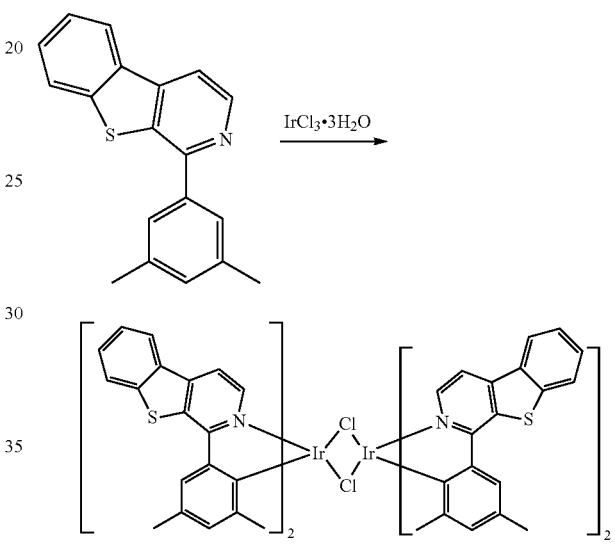

Synthesis of Dimer:

4-(3',5'-dimethylphenyl)-3-azadibenzothiophene (2.0 g, 6.9 mmol), 2-ethoxyethanol (25 mL) and water (5 mL) were charged in a 100 mL three-neck round bottom flask. Nitrogen gas was bubbled through the reaction mixture 45 minutes. $IrCl_3.H_2O$ (0.6 g, 2 mmol) was then added and the reaction mixture was heated to reflux under nitrogen for 17 h. The reaction mixture was cooled to ambient and filtered. The orange/red residue was collected and washed with methanol (2×15 mL) followed by hexanes (2×15 mL). 1.0 gram of the dichlorobridged Iridium dimer was obtained after drying in vacuum oven.

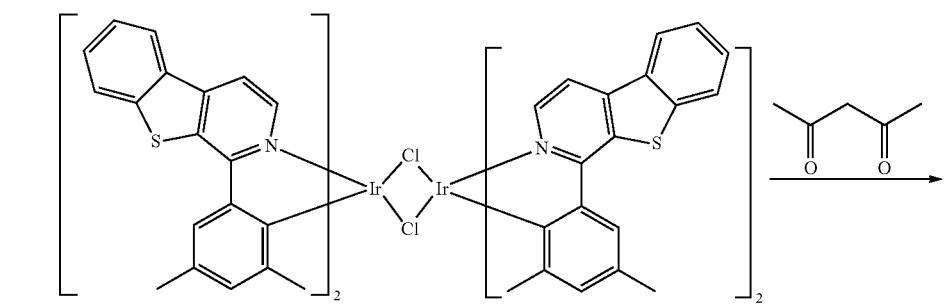

-continued

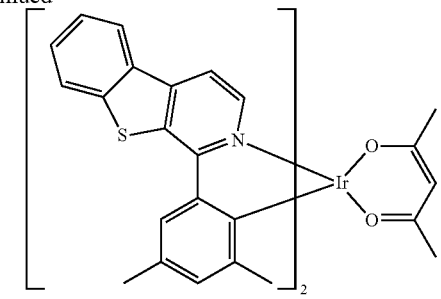

Compound 86

Synthesis of Compound 86.

Dichlorobridged Iridium dimer (1.0 g, 0.7 mmol), 10 mol eq. 2,4-pentanedione (1.4 g), 20 mol. eq. of $Na_2CO_3$ (2.0 g) and 25 mL of 2-ethoxyethanol were placed in a 250 mL round bottom flask. The reaction mixture was stirred at ambient for 24 h. 1 g of celite and 100 mL of dichloromethane was added to the reaction mixture to dissolve the product. The mixture was then filtered through a bed of celite. The filtrate was then passed through a through a silica/alumina plug and washed with dichloromethane. The clarified solution was then filtered through GF/F filter paper the filtrate was heated to remove most of the dichloromethane. 10 mL of isopropanol was then added and the slurry was cooled to ambient and the product was filtered and washed with isopropanol and dried to give 1.0 g of crude product (57% yield). This product was then recrystallised twice using dichloromethane and isopropanol and then sublimed.

Device Examples

All devices are fabricated by high vacuum (<$10^{-7}$ Torr) thermal evaporation. The anode electrode is 800 Å of indium tin oxide (ITO). The cathode consisted of 10 Å of LiF followed by 1000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

Particular devices are provided wherein inventive compounds, Compound 1, Compound 7, Compound 8, Compound 22, and Compound 31, are the emitting dopant and H1 is the host. All device examples have organic stacks consisting of sequentially, from the ITO surface, 100 Å of E1 as the hole injecting layer (HIL), 300 Å of 4,4'-bis[N-(1-naphthyl)-N-phenylamino]biphenyl (α-NPD) as the hole transport layer (HTL), 300 Å of H1, a host material, doped with 7% and 10% of the invention compound, as the emissive layer (EML) (i.e., A % indicates the percentage of the dopant compound present in the EML), 50 Å of H1 as the blocking layer (BL) and 400 Å of $Alq_3$ (tris-8-hydroxyquinoline aluminum) as the electron transport layer (ETL).

Comparative Example 1 was fabricated similarly to the Device Examples, except that the EML comprised H1 as the host doped with 7% of E1.

As used herein, the following compounds have the following structures:

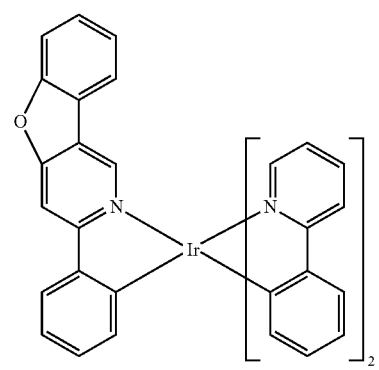

Compound 1

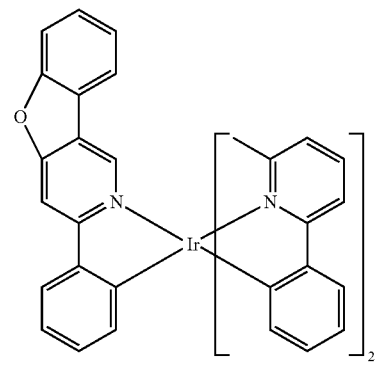

Compound 7

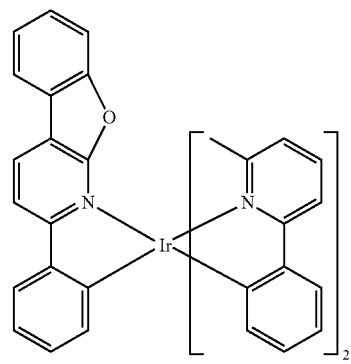

Compound 8

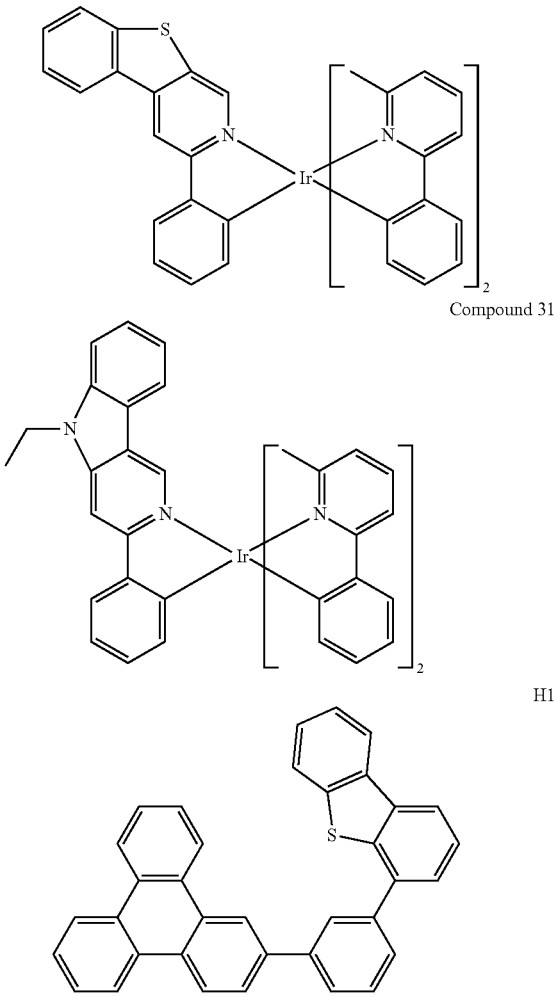

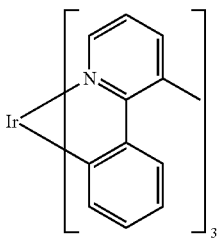

Particular materials for use in an OLED are provided. In particular, the materials may be used as an emitting dopant in the emissive layer of an OLED are provided which may lead to devices having particularly good properties. The device structures are provided in Table 2 and the corresponding measured device data is provided in Table 3. Devices having an emissive layer comprising Compounds, 1, 7, 8, 22, and 31 show high device efficiency, reduced operating voltage and long lifetime.

The following terms are used in Tables 2 and 3 and are defined herein:

Ex. is an abbreviation for example. Comp. Ex. is an abbreviation for Comparative Example. LE is luminous efficiency, which is defined as the luminance divided by the driving current density of the OLED. EQE is external quantum efficiency, which is defined as the ratio of measured number of photons to the electrons passed across the junction. PE is power efficiency, which is defined as the total luminous flux emitted divided by the total power input. $L_0$ is the initial luminance, which is defined as the initial brightness at a certain current density. $RT_{80\%}$ is a measure of lifetime, which is defined as the time required for the initial luminance, $L_0$, to decay to 80% of its value, at a constant current density of 40 mA/cm² at room temperature.

TABLE 2

| Example | HIL | HTL | Host | A | % | BL | ETL |
|---|---|---|---|---|---|---|---|
| Example 1 | E1 100 Å | NPD 300 Å | H1 | Compound 1 | 7% | H1 50 Å | Alq₃ 400 Å |
| Example 2 | E1 100 Å | NPD 300 Å | H1 | Compound 1 | 10% | H1 50 Å | Alq₃ 400 Å |
| Example 3 | E1 100 Å | NPD 300 Å | H1 | Compound 7 | 7% | H1 50 Å | Alq₃ 400 Å |
| Example 4 | E1 100 Å | NPD 300 Å | H1 | Compound 7 | 10% | H1 50 Å | Alq₃ 400 Å |
| Example 5 | E1 100 Å | NPD 300 Å | H1 | Compound 8 | 7% | H1 50 Å | Alq₃ 400 Å |
| Example 6 | E1 100 Å | NPD 300 Å | H1 | Compound 8 | 10% | H1 50 Å | Alq₃ 400 Å |
| Example 7 | E1 100 Å | NPD 300 Å | H1 | Compound 22 | 7% | H1 50 Å | Alq₃ 400 Å |
| Example 8 | E1 100 Å | NPD 300 Å | H1 | Compound 22 | 10% | H1 50 Å | Alq₃ 400 Å |
| Example 9 | E1 100 Å | NPD 300 Å | H1 | Compound 31 | 7% | H1 50 Å | Alq₃ 400 Å |
| Example 10 | E1 100 Å | NPD 300 Å | H1 | Compound 31 | 10% | H1 50 Å | Alq₃ 400 Å |
| Comparative Example 1 | E1 100 Å | NPD 300 Å | H1 | E1 | 7% | H1 50 Å | Alq₃ 400 Å |

TABLE 3

| | | CIE | | | At 1000 nits | | | At 40 mA/cm² | |
|---|---|---|---|---|---|---|---|---|---|
| Ex. | λ max, nm | X | Y | V (V) | LE (cd/A) | EQE (%) | PE (lm/W) | Lo, nits | RT$_{80\%}$, h |
| Ex. 1 | 526 | 0.336 | 0.618 | 5.9 | 60.9 | 16.7 | 32.2 | 16,756 | 42 |
| Ex. 2 | 524 | 0.346 | 0.614 | 5.5 | 59.3 | 16.3 | 34.0 | 17,225 | 28 |
| Ex. 3 | 522 | 0.336 | 0.619 | 5.6 | 68.9 | 18.9 | 38.7 | 18,954 | 31 |
| Ex. 4 | 522 | 0.344 | 0.616 | 5.1 | 71.7 | 19.6 | 44.1 | 21,234 | 16 |
| Ex. 5 | 562 | 0.488 | 0.507 | 5.3 | 66.9 | 20.7 | 39.9 | 21,511 | 68 |
| Ex. 6 | 564 | 0.493 | 0.503 | 5.1 | 67.1 | 21 | 41.7 | 22,767 | 44 |
| Ex. 7 | 540 | 0.376 | 0.596 | 5.6 | 69.2 | 18.8 | 38.8 | 18,869 | 120 |
| Ex. 8 | 546 | 0.396 | 0.583 | 5.1 | 66.9 | 18.4 | 41.2 | 20,471 | 120 |
| Ex. 9 | 520 | 0.333 | 0.618 | 5.6 | 55.8 | 15.4 | 31.3 | 15,085 | 71 |
| Ex. 10 | 526 | 0.344 | 0.614 | 5.1 | 65.6 | 18 | 40.8 | 20,055 | 52 |
| Comp. Ex. 1 | 527 | 0.344 | 0.614 | 6.4 | 56.7 | 15.6 | 27.6 | 15,436 | 155 |

From Device Examples 1-10, it can be seen that the invention compounds, Compounds 1, 7, 8, 22, and 31, as emitting dopants in green phosphorescent OLEDs provide high device efficiency (i.e., LE>60 cd/A at 1000 cd/m2). This suggests that the novel ligand structures have a sufficiently high triplet energy for green electrophosphorescence. Also of note is the high stability of devices containing invention compounds as the emitting dopant. The lifetime, $RT_{80\%}$ is 120 h for Compound 22. Thus, the invention compounds may provide devices with improved efficiency and a long lifetime.

In addition, devices incorporating the inventive compounds display reduced operating voltage. For example, Compound 1, Compound 7, Compound 8, Compound 22, and Compound 31 all gave a lower device voltage, 5.5 V at 1000 cd/m², 5.1 V at 1000 cd/m², 5.1 V at 1000 cd/m², 5.1 V at 1000 cd/m², and 5.1 V at 1000 cd/m² respectively) compare E1 which had 6.4 V at 1000 cd/m².

The data suggest that these novel metal complexes containing aza DBX ligands can be excellent emitting dopants for phosphorescent OLEDs, providing devices having low voltage, high efficiency and long lifetime. Taken together, this indicates that the novel compounds provided may be an improvement over the commonly used emitting dopants, such as Ir(ppy)₃, which display industry standards characteristics.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A compound having the structure of formula (L)$_n$ (L')$_{3-n}$Ir, wherein n is 1 or 2, ligand L has a structure

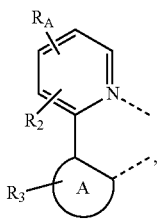

FORMULA I and ligand L' has a structure selected from the group consisting of:

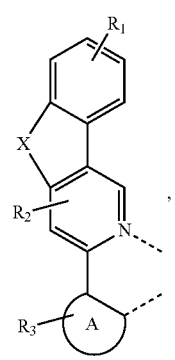

II

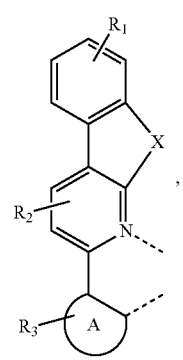

III

-continued

IV

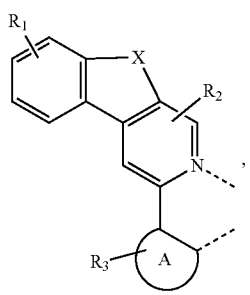

V

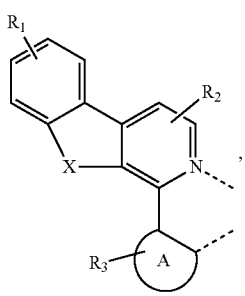

VI

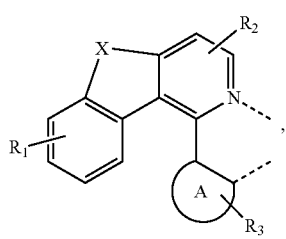

VII

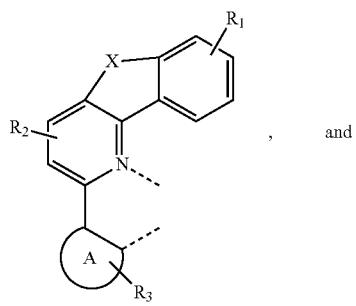

IX

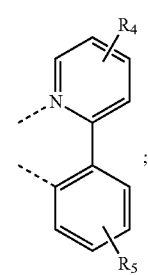

wherein each A is independently a 5-membered or 6-membered aromatic or heteroaromatic ring;

wherein $R_A$ is a substituent having the structure

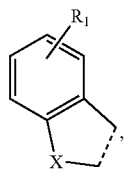

wherein $R_A$ is fused to the pyridine ring of FORMULA I and the dashed line in $R_A$ indicates where $R_A$ is fused to the pyridine ring of FORMULA I;

wherein each X is independently selected from the group consisting of CRR", C=O, BR, O, S, and Se;

wherein each R and R' is independently selected from hydrogen and alkyl;

wherein each $R_1$, $R_3$, $R_4$, and $R_5$ may independently represent mono, di, tri, or tetra substitutions;

wherein $R_2$ may represent mono or di substitutions;

wherein each of $R_1$, $R_7$, $R_3$, $R_4$, and $R_5$ are independently selected from the group consisting of hydrogen, alkyl, alkoxy, amino, alkenyl, alkynyl, arylalkyl, aryl, and heteroaryl; and wherein the compound is heteroleptic.

2. The compound of claim 1, wherein ligand L' is

IX

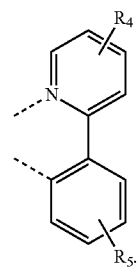

3. The compound of claim 2, wherein the compound is selected from the group consisting of:

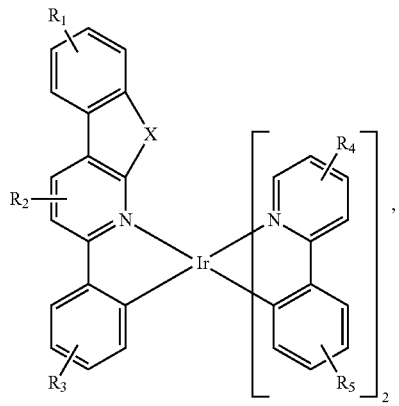

-continued
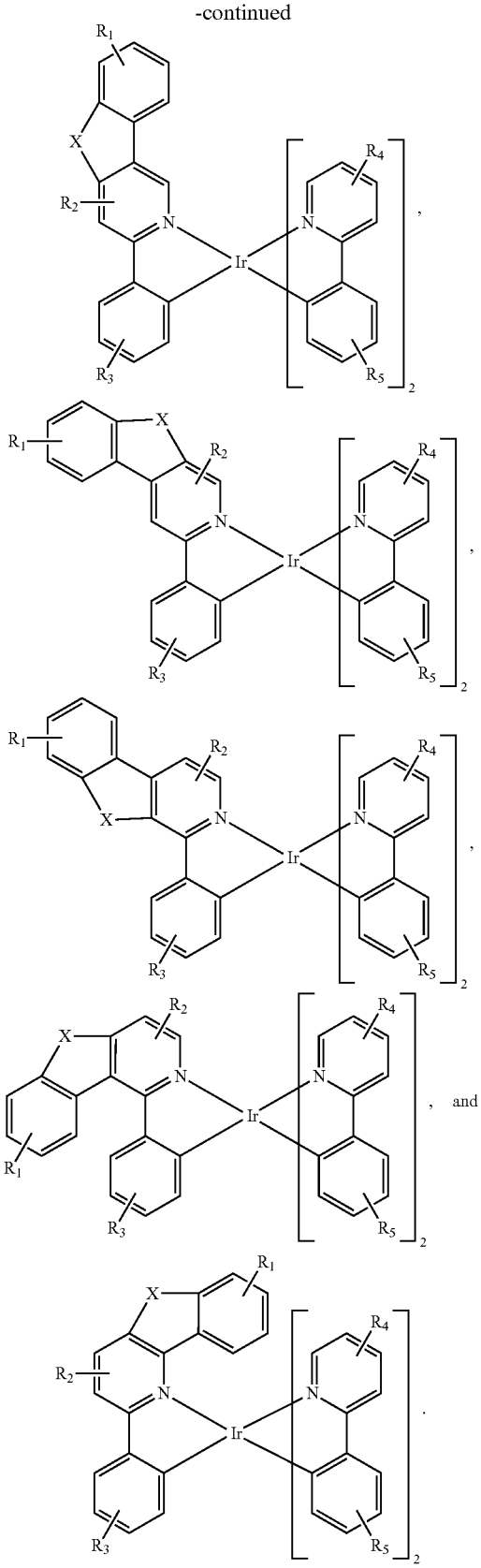
4. The compound of claim 1, wherein X is O.
5. The compound of claim 1, wherein X is S.
6. The compound of claim 1, wherein X is CRR'.
7. The compound of claim 1, wherein X is CO.
8. The compound of claim 1, wherein the compound is selected from the group consisting of:
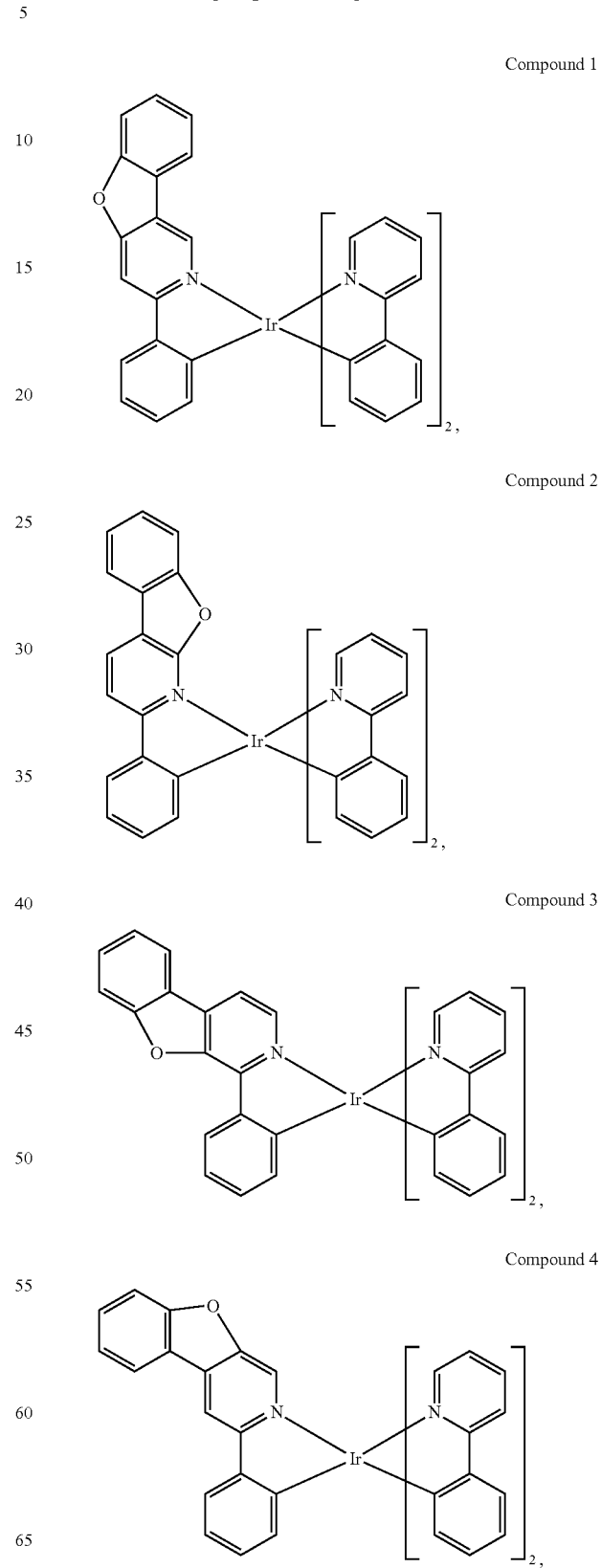

Compound 5
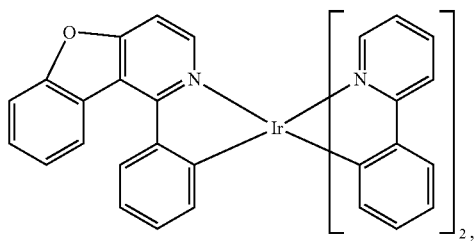
Compound 6
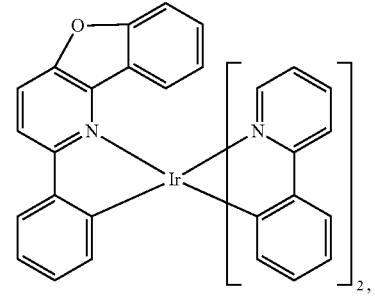
Compound 7
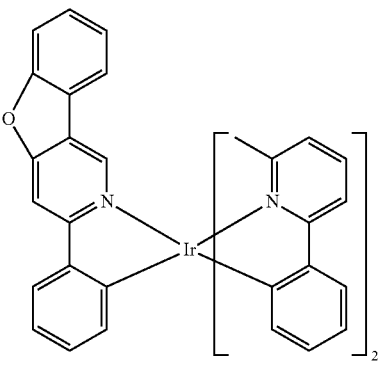
Compound 8
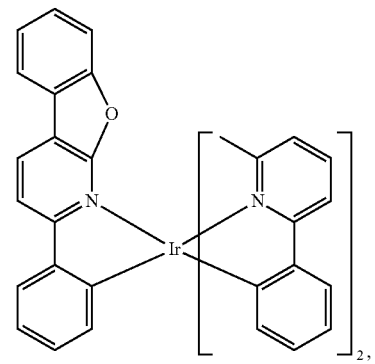
Compound 9
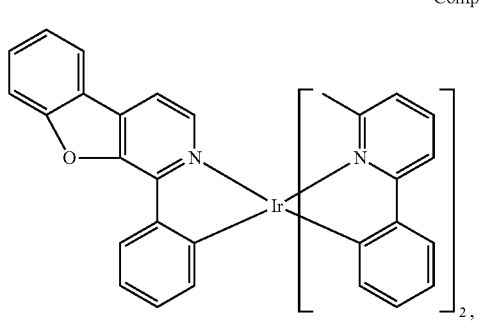
Compound 10
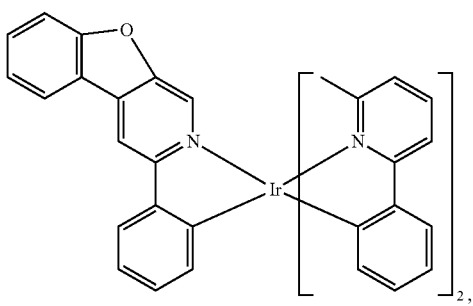
Compound 11
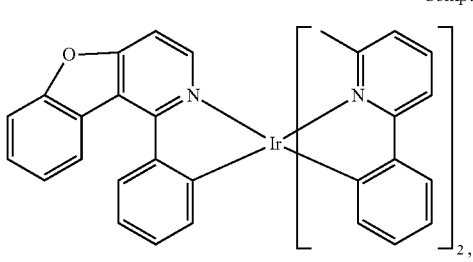
Compound 12
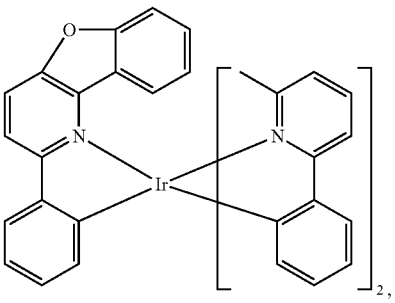
Compound 13
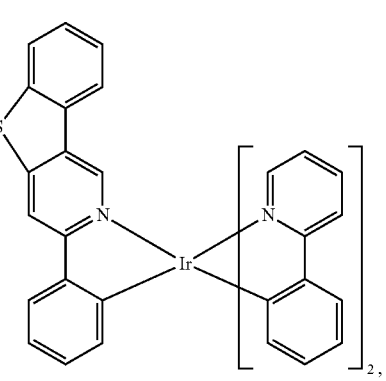

Compound 14
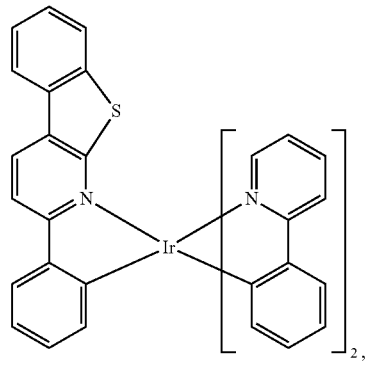
Compound 15
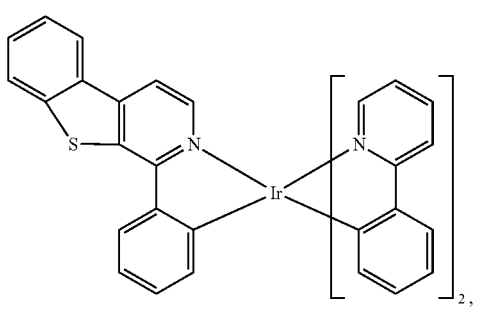
Compound 16
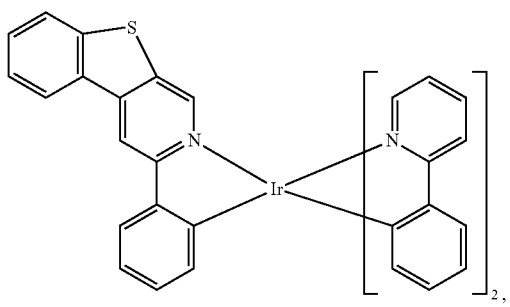
Compound 17
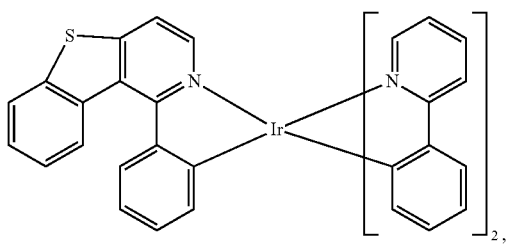
Compound 18
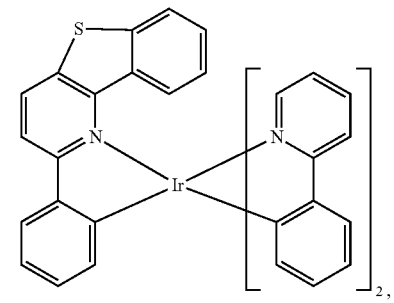
Compound 19
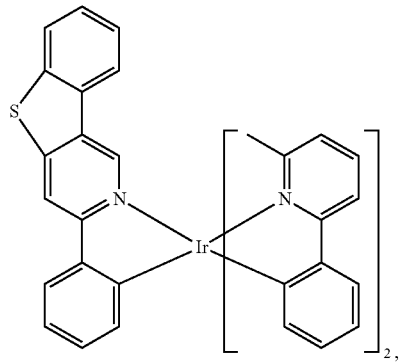
Compound 20
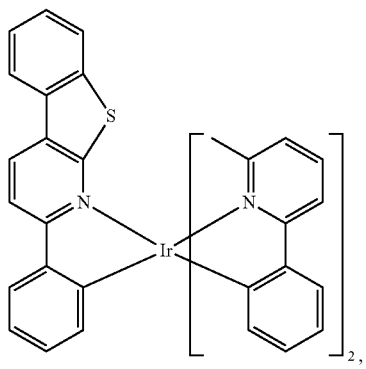
Compound 21
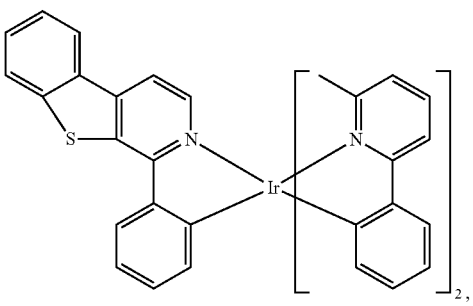
Compound 22
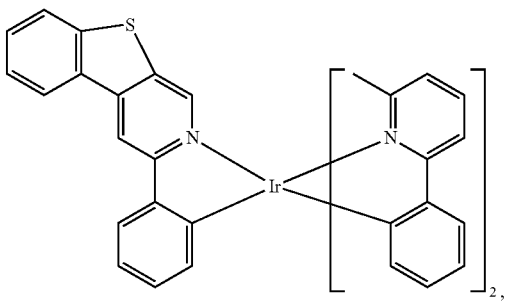

Compound 23
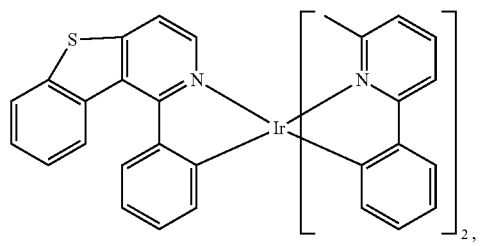
Compound 24
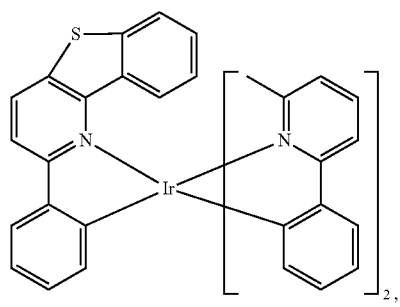
Compound 37
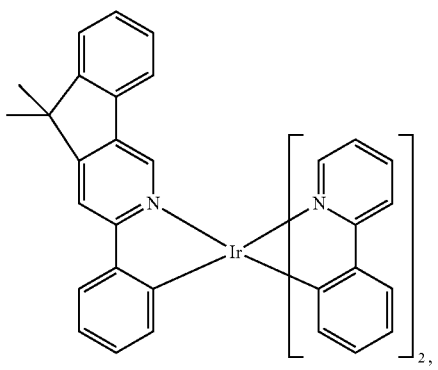
Compound 38
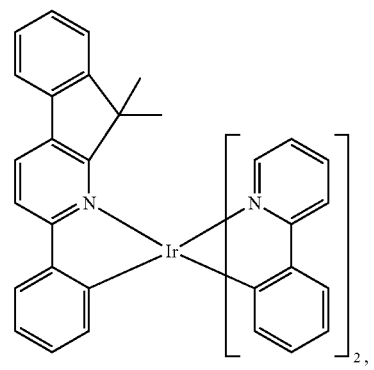
Compound 39
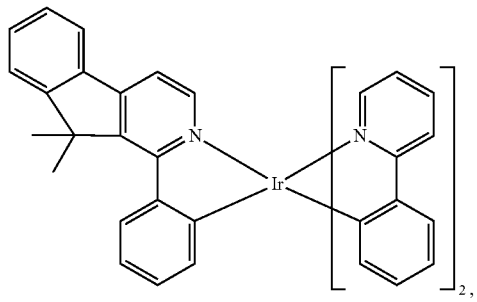
Compound 40
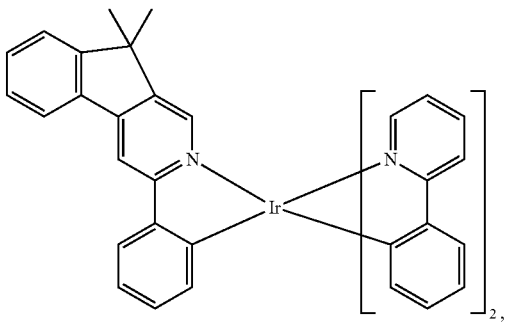
Compound 41
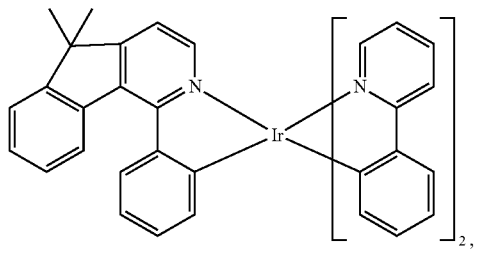
Compound 42
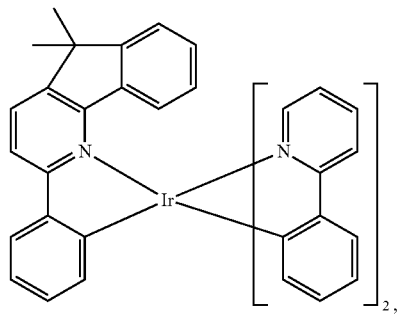

Compound 43
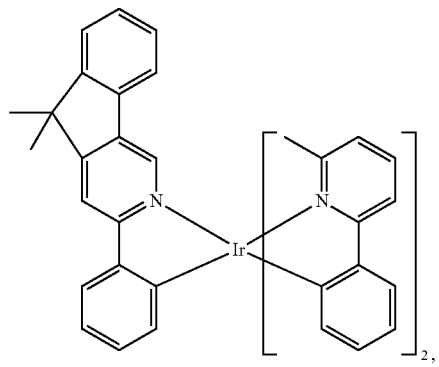
Compound 44
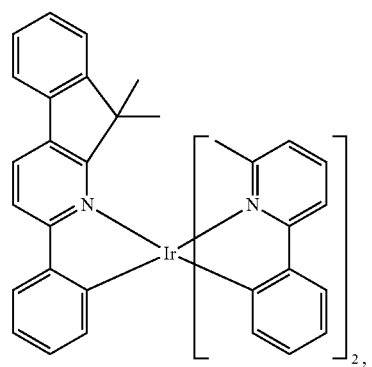
Compound 45
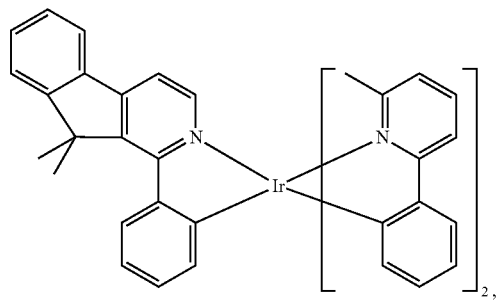
Compound 46
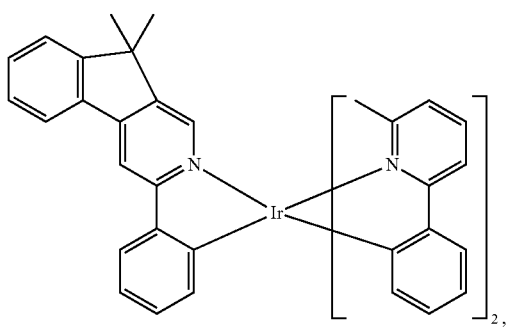
Compound 47
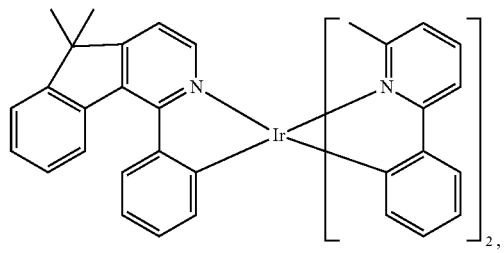
Compound 48
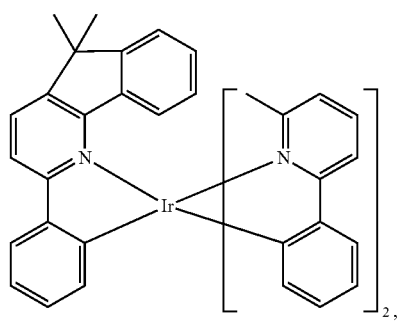
Compound 49
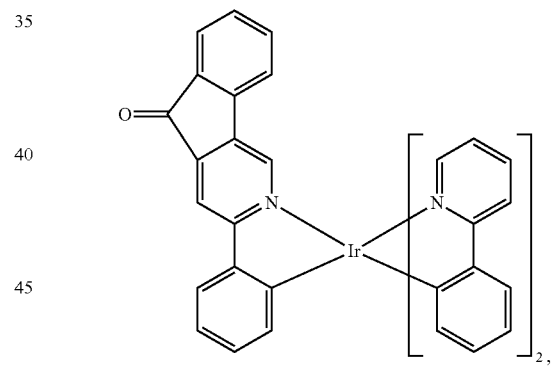
Compound 50
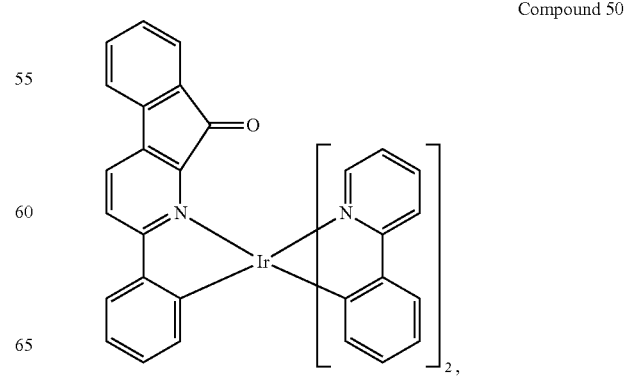

Compound 51
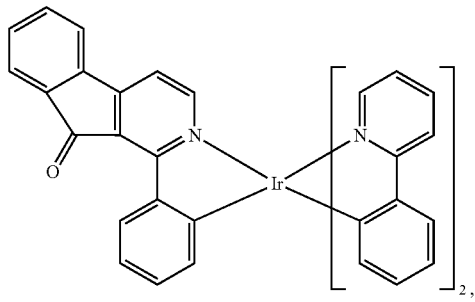
Compound 52
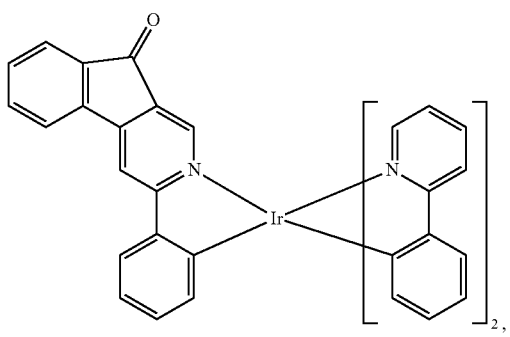
Compound 53
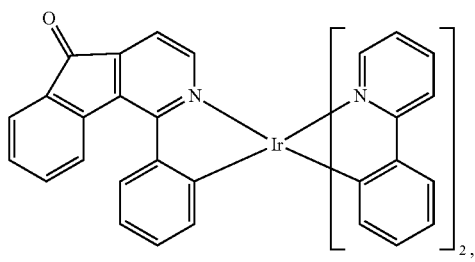
Compound 54
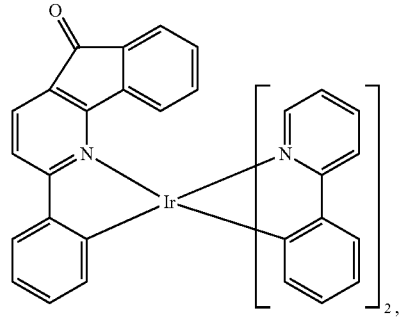
Compound 55
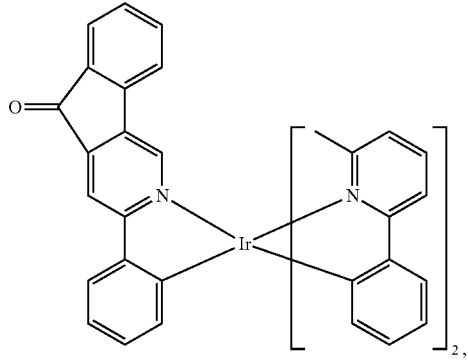
Compound 56
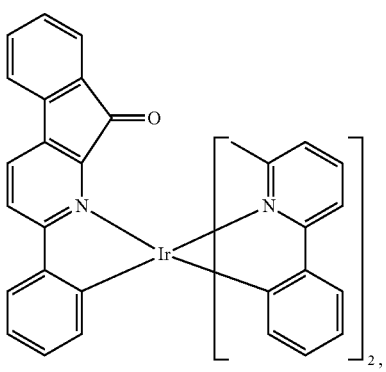
Compound 57
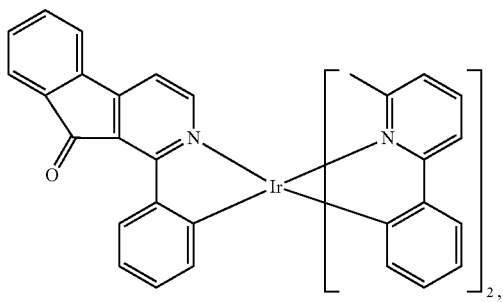
Compound 58
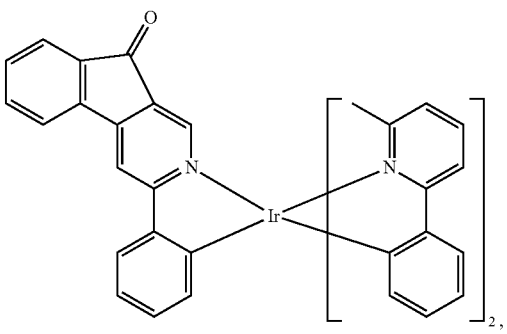

Compound 59

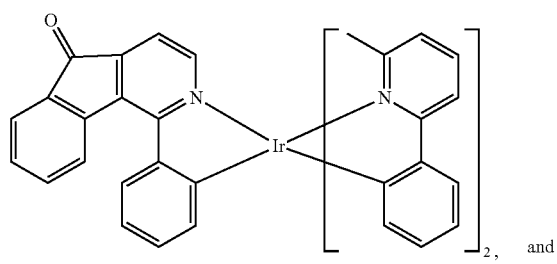

Compound 60

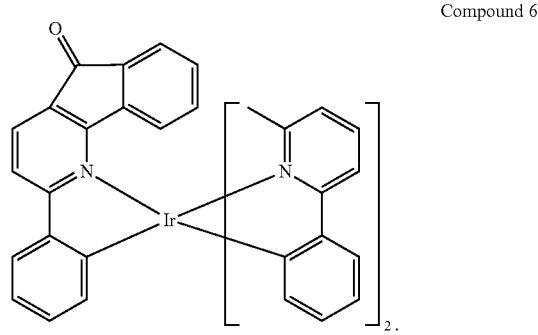

9. The compound of claim 8, wherein the compound is selected from the group consisting of Compound 1-Compound 12.

10. The compound of claim 8, wherein the compound is selected from the group consisting of Compound 13-Compound 24.

11. The compound of claim 8, wherein the compound is selected from the group consisting of Compound 37-Compound 48.

12. The compound of claim 8, wherein the compound is selected from the group consisting of Compound 49-Compound 60.

13. An organic light emitting device, comprising:
an anode;
a cathode; and
an organic layer disposed between the anode and the cathode, the organic layer comprising a compound having the structure of formula $(L)_n(L')_{3-n}$Ir, wherein n is 1 or 2, ligand L has a structure

FORMULA I

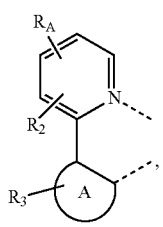

and ligand L' has a structure selected from the group consisting of:

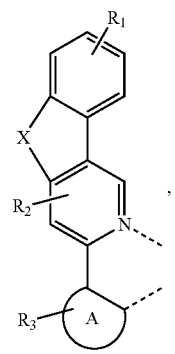
II

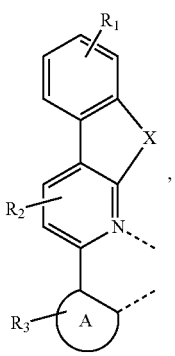
III

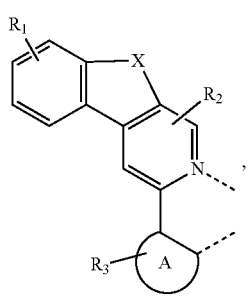
IV

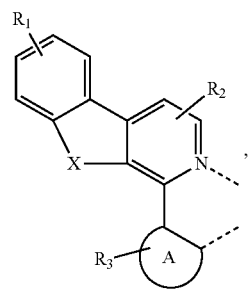
V

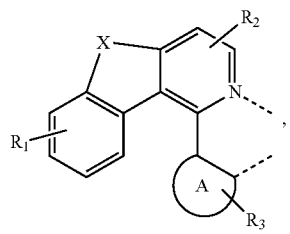
VI

-continued

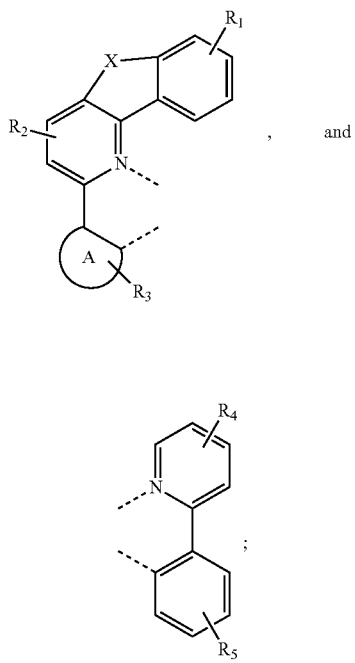

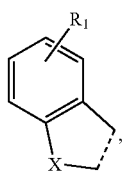

wherein each A is independently a 5-membered or 6-membered aromatic or heteroaromatic ring;

wherein $R_A$ is a substituent having the structure

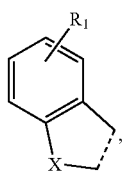

wherein $R_A$ is fused to the pyridine ring of FORMULA I and the dashed line in $R_A$ indicates where $R_A$ is fused to the pyridine ring of FORMULA I;

wherein each X is independently selected from the group consisting of CRR', C=O; BR, O; S, and Se;

wherein each R and R' is independently selected from hydrogen and alkyl;

wherein each $R_1$, $R_3$, $R_4$, and $R_5$ may independently represent mono, di, tri, or tetra substitutions;

wherein $R_2$ may represent mono or di substitutions;

wherein each of $R_1$, $R_2$, $R_3$, $R_4$, and $R_5$ are independently selected from the group consisting of hydrogen, alkyl, alkoxy, amino, alkenyl, alkynyl, arylalkyl, aryl, and heteroaryl; and wherein the compound is heteroleptic.

14. The device of claim 13, wherein the organic layer is an emissive layer and the compound is an emitting dopant.

15. The device of claim 13, wherein the organic layer further comprises a host.

16. The device of claim 15, wherein the host has the formula:

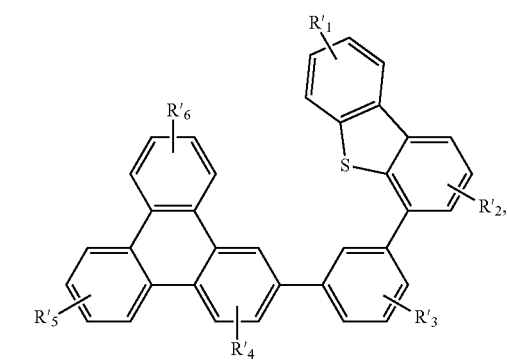

wherein $R'_2$ and $R'_4$ may represent mono, di, or tri substitutions;

wherein $R'_1$, $R'_3$, $R'_5$, and $R'_6$ may represent mono, di, tri, or tetra substitutions; and wherein each of $R'_1$, $R'_2$, $R'_3$, $R'_4$, $R'_5$, and $R'_6$ are each independently selected from the group consisting of hydrogen, alkyl and aryl.

17. The device of claim 13, wherein the compound is selected from the group consisting of:

Compound 1

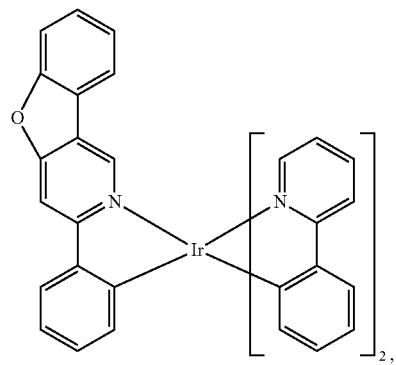

Compound 2

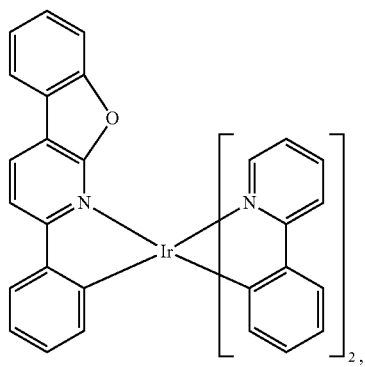

Compound 3
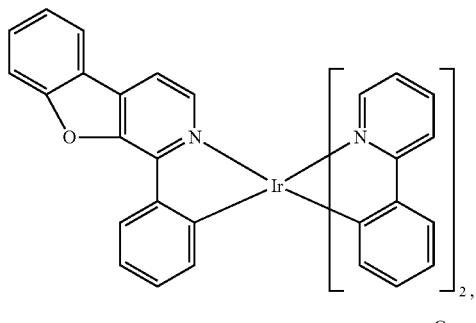
Compound 4
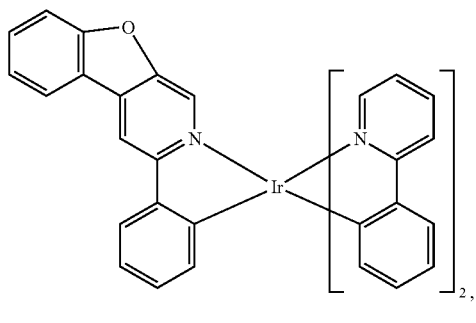
Compound 5
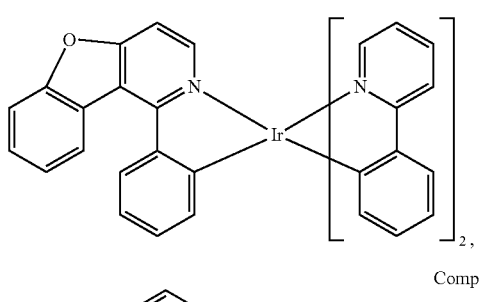
Compound 6
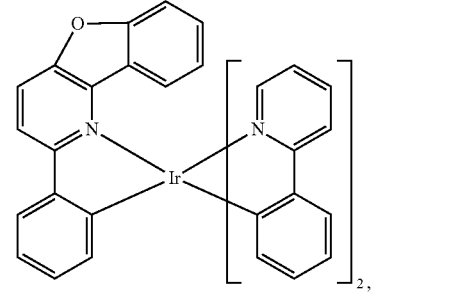
Compound 7
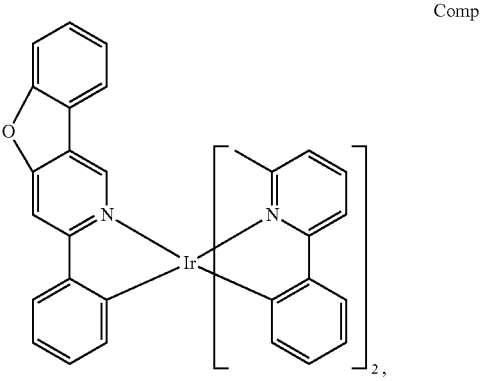
Compound 8
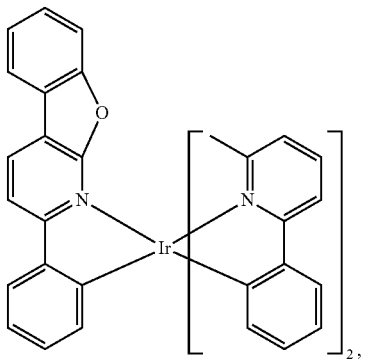
Compound 9
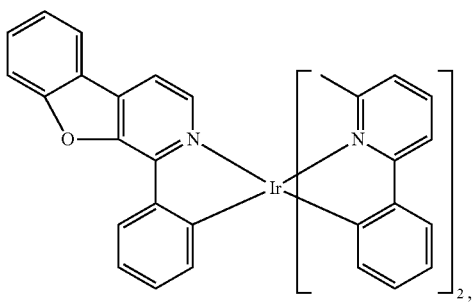
Compound 10
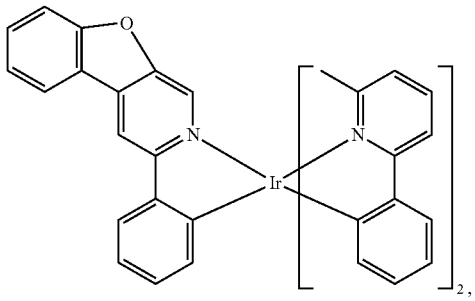
Compound 11
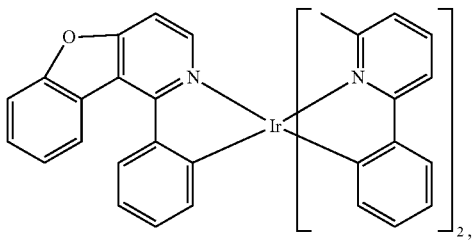
Compound 12
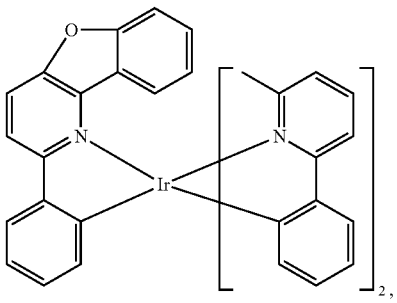

Compound 13
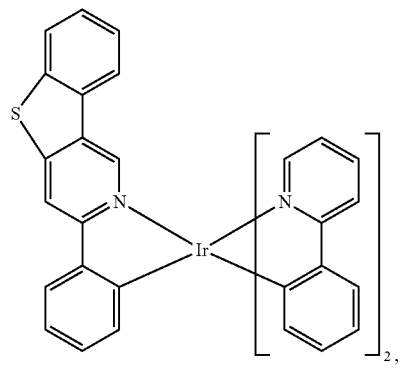
Compound 14
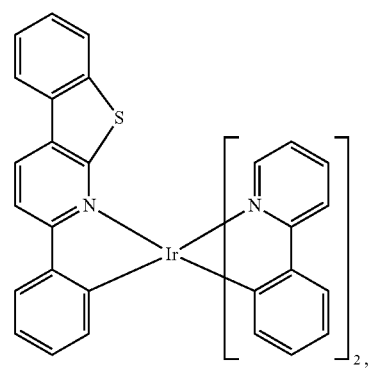
Compound 15
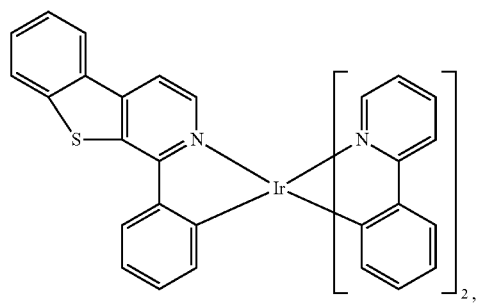
Compound 16
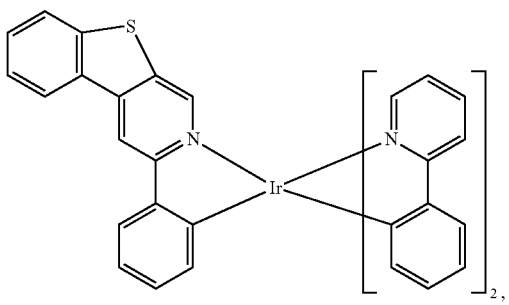
Compound 17
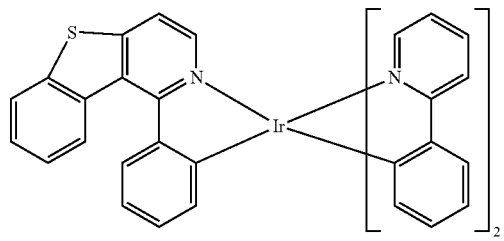
Compound 18
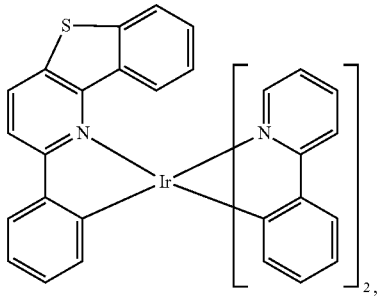
Compound 19
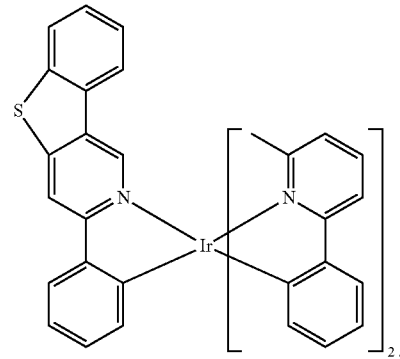
Compound 20
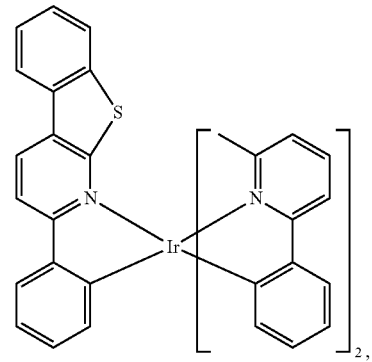
Compound 21

Compound 22
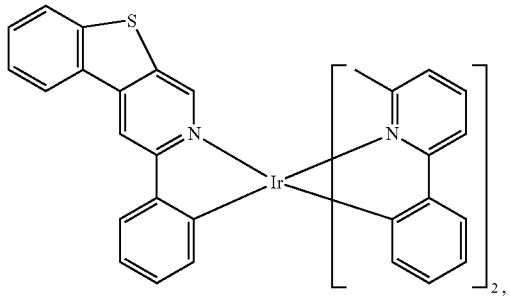
Compound 23
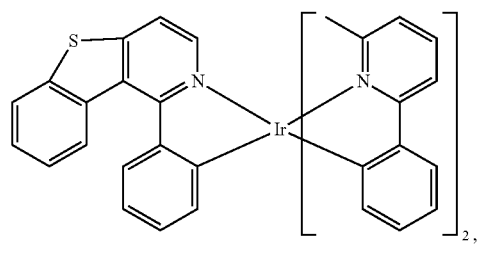
Compound 24
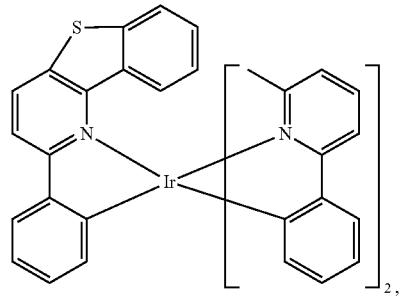
Compound 37
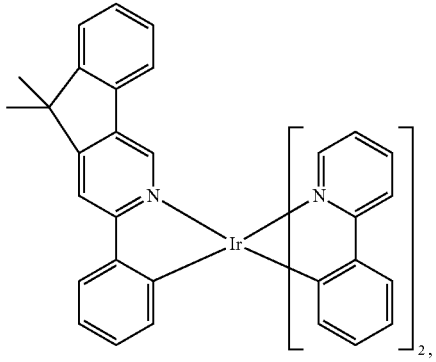
Compound 38
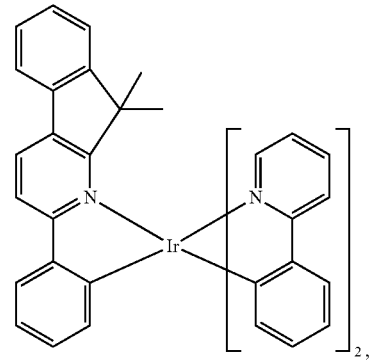
Compound 39
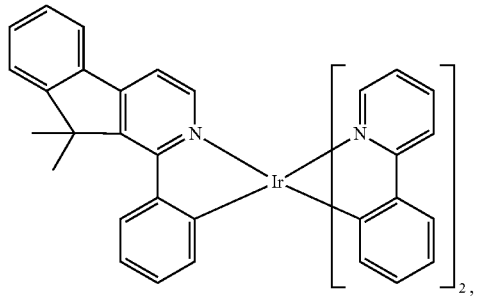
Compound 40
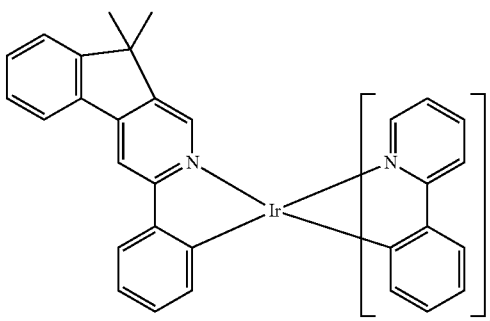
Compound 41
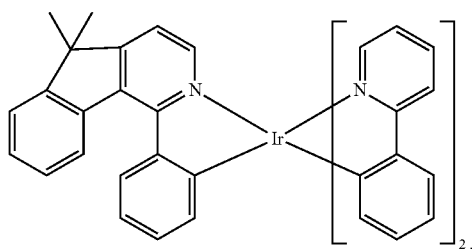
Compound 42
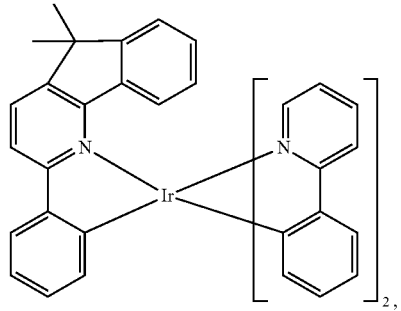
Compound 43
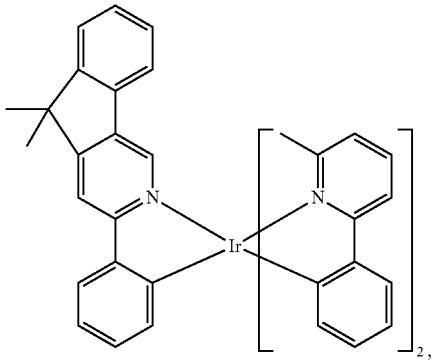

Compound 44
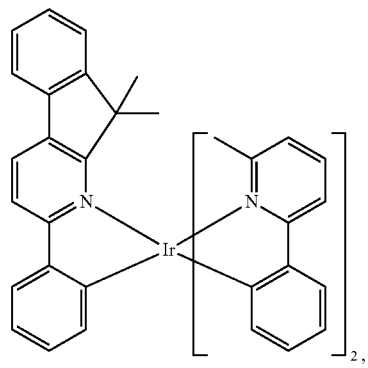
Compound 45
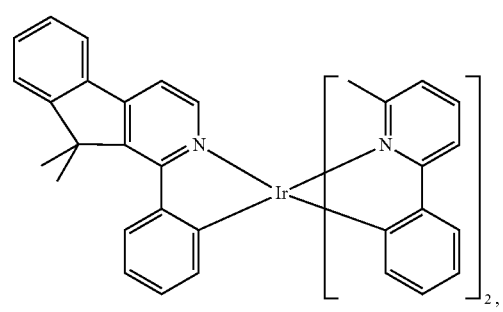
Compound 46
Compound 47
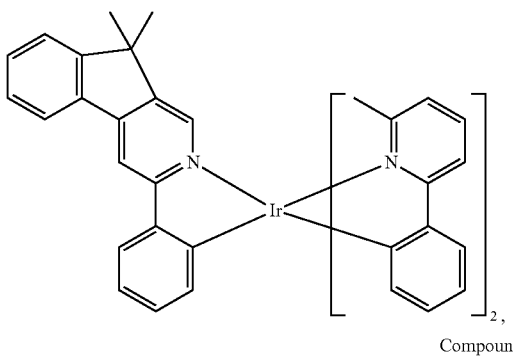
Compound 48
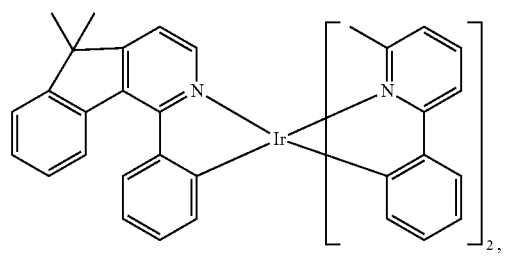
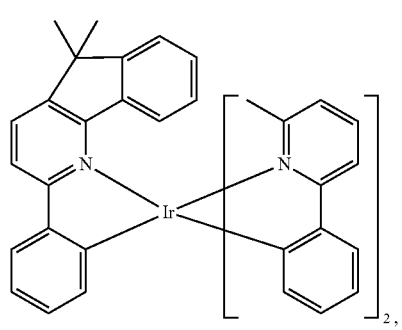
Compound 49
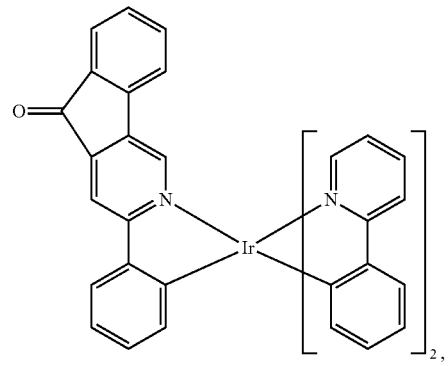
Compound 50
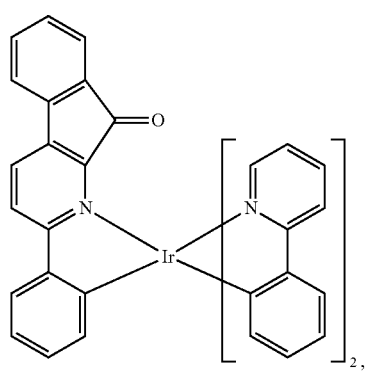
Compound 51
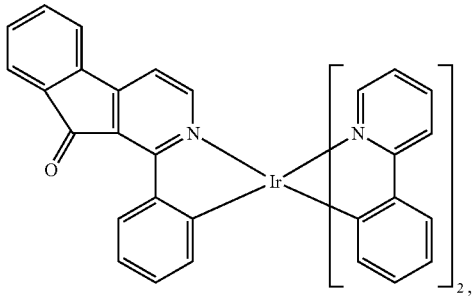
Compound 52

Compound 53
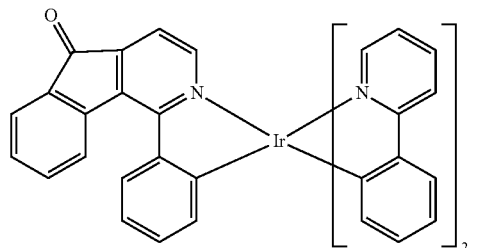
Compound 54
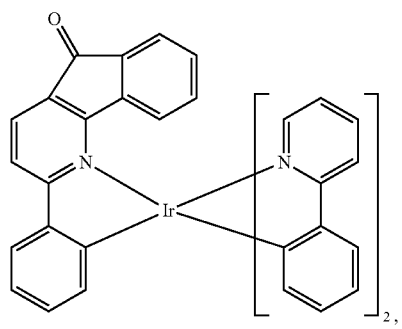
Compound 55
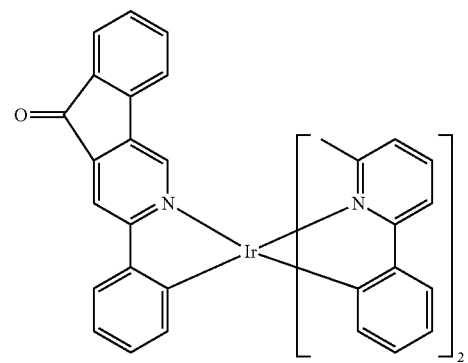
Compound 56
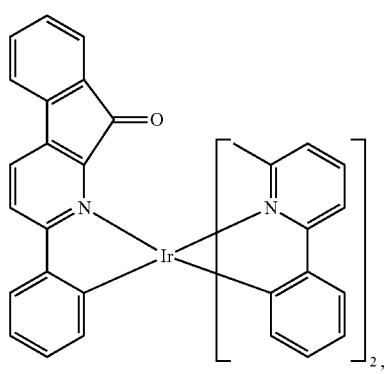
Compound 57
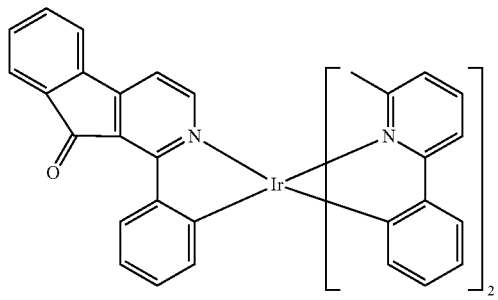
Compound 58
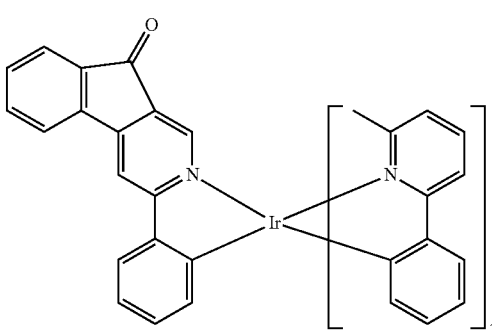
Compound 59
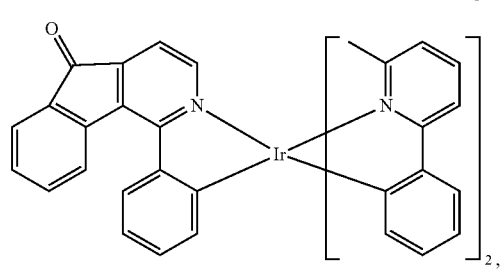
and
Compound 60
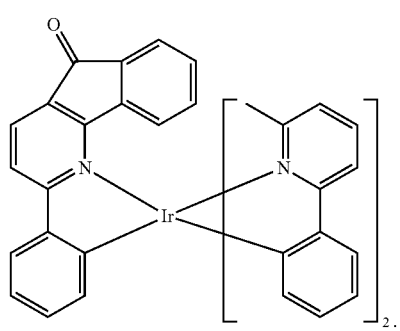
* * * * *